US012019022B2

United States Patent
Guzhva et al.

(10) Patent No.: US 12,019,022 B2
(45) Date of Patent: Jun. 25, 2024

(54) SYSTEMS AND METHODS FOR DISTINGUISHING FERTILE PLANT SPECIMENS FROM STERILE PLANT SPECIMENS

(71) Applicant: Monsanto Technology LLC, St. Louis, MO (US)

(72) Inventors: Dmytro Guzhva, Lethbridge (CA); Maria Cristina Ubach, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 734 days.

(21) Appl. No.: 15/734,934

(22) PCT Filed: Jun. 6, 2019

(86) PCT No.: PCT/US2019/035788
§ 371 (c)(1),
(2) Date: Dec. 3, 2020

(87) PCT Pub. No.: WO2019/236843
PCT Pub. Date: Dec. 12, 2019

(65) Prior Publication Data
US 2021/0295041 A1  Sep. 23, 2021

Related U.S. Application Data

(60) Provisional application No. 62/681,494, filed on Jun. 6, 2018.

(51) Int. Cl.
*G06K 9/00* (2022.01)
*G01C 5/00* (2006.01)
(Continued)

(52) U.S. Cl.
CPC ......... *G01N 21/6486* (2013.01); *G01N 21/31* (2013.01); *G01N 33/0098* (2013.01);
(Continued)

(58) Field of Classification Search
CPC ...... G06K 9/00; A61K 35/12; G01N 3/56961; G01C 5/00
(Continued)

(56) References Cited

U.S. PATENT DOCUMENTS 5,764,819 A    6/1998  Orr et al.
6,052,187 A *  4/2000  Krishnan ............. A01C 21/007
                                                 356/369
(Continued)

FOREIGN PATENT DOCUMENTS

CN    102788796 A    11/2012
CN    103868842 A    6/2014
(Continued)

OTHER PUBLICATIONS

Ben-Zur, R., et al., "Optical Analytical Methods for Detection of Pesticides," 2011, Rev Anal Chem, 30:123-139, 17 pages.
(Continued)

*Primary Examiner* — Seyed H Azarian
(74) *Attorney, Agent, or Firm* — MCBEE MOORE & VANIK IP LLC

(57) ABSTRACT

Analyzing reflections and/or emissions of electromagnetic radiation to distinguish fertile plant specimens from sterile plant specimens. In an aspect, the presence of wavelengths associated with pollen in the electromagnetic radiation reflections and/or emissions indicates a plant specimen is fertile, and the absence of wavelengths associated with pollen in the reflections and/or emissions indicates a plant specimen is sterile. In other aspects, spectral signature differences in the reflections and/or emissions that are (Continued)

indicative of other properties besides pollen (e.g., petal color, etc.) are utilized to distinguish between fertile and sterile plant specimens.

12 Claims, 54 Drawing Sheets

(51) Int. Cl.
    *G01N 21/31*     (2006.01)
    *G01N 21/64*     (2006.01)
    *G01N 33/00*     (2006.01)
    *G06V 10/143*     (2022.01)
    *G06V 20/10*     (2022.01)
    *G06V 20/69*     (2022.01)

(52) U.S. Cl.
    CPC .......... *G06V 10/143* (2022.01); *G06V 20/188* (2022.01); *G06V 20/69* (2022.01); *G06V 20/194* (2022.01)

(58) Field of Classification Search
USPC ....... 382/100, 103, 106, 110, 109, 153, 162, 382/173, 181, 189, 209, 219, 254, 274, 382/276, 286–291, 312, 321; 435/7.1; 536/23.6; 356/369, 3; 703/11
See application file for complete search history.

(56) References Cited

U.S. PATENT DOCUMENTS

| | | | |
|---|---|---|---|
| 6,495,363 B2 | 12/2002 | Bogdanov | |
| 9,495,597 B2 | 11/2016 | Hundley et al. | |
| 2007/0061912 A1* | 3/2007 | Bisht | C12N 15/8289 536/23.6 |
| 2007/0240242 A1 | 10/2007 | Modiano et al. | |
| 2011/0125477 A1* | 5/2011 | Lightner | G05B 17/02 703/11 |
| 2014/0115730 A1* | 4/2014 | Cope | G01N 33/56961 435/7.1 |
| 2014/0285673 A1* | 9/2014 | Hundley | G06V 10/143 382/103 |
| 2017/0238488 A1* | 8/2017 | Bangera | G16C 99/00 |
| 2021/0068335 A1* | 3/2021 | Noivirt-Brik | G06N 20/00 |

FOREIGN PATENT DOCUMENTS

| | | |
|---|---|---|
| CN | 104931470 A | 9/2015 |
| JP | 2013050406 A | 3/2013 |
| WO | 2015105831 A1 | 7/2015 |
| WO | 2018112318 A1 | 6/2018 |
| WO | 20180202891 A1 | 11/2018 |

OTHER PUBLICATIONS

Davis, R.W., et al., "Multiplex Fluorometric Assessment of Nutrient Limitation as a Strategy for Enhanced Lipid Enrichment and Harvesting of Neochloris Oleoabundans," 2012, Biotechnol Bioeng, 109/10:2503-2512. Abstract only.

Ellingsen, P., et al., "Spectral Correlation Analysis of Amyloid β Plaque Inhomogeneity from Double Staining Experiments," 2013, J Biomed Optics, 18/10:101313-1 to 101313-6, 7 pages.

Mo, C., et al., "Detecting Drought Stress in Soybean Plants Using Hyperspectral Fluorescence Imaging," 2015, J Biosystems Eng., 40/4:335-344, 10 pages.

Mo, C., et al., "Multispectral Fluorescence Imaging Technique for Discrimination of Cucumber Seed Viability," 2015, ASABE, 58/4:959-968, 2 pages. Abstract.

Van Benthem, M. H., et al., "PARAFAC Modeling of Three-Way Hyperspectral Images: Engogenous Fluorophores as Helth Biomarkers in Aquatic Species," 2011, Chemometrics and Intelligent Laboratory Systems, 106/1:115-124, Abstract only.

Vermaas, W.F.J., et al., "In vivo Hyperspectral Confocal Fluorescence Imaging to Deermine Pigment Localization and Distribution in Cyanobacterial Cells," 2008, PNAS, 105/10:4050-4055, 6 pages.

International Preliminary Report on Patentability issued in PCT/US2019/035788, dated Dec. 8, 2020, 8 pages.

International Search Report and Written Opinion issued in PCT/US2019/35788, dated Sep. 19, 2019, 10 pages.

* cited by examiner

Sterile Anthers with infertile pollen

SYSTEMS AND METHODS FOR DISTINGUISHING FERTILE PLANT SPECIMENS FROM STERILE PLANT SPECIMENS

TECHNICAL FIELD

Aspects of the present disclosure generally relate to distinguishing fertile plant specimens from sterile plant specimens, and more particularly to systems and methods for analyzing reflections and/or emissions of electromagnetic radiation to distinguish fertile plant specimens from sterile plant specimens.

BACKGROUND

In agricultural contexts, roguing comprises identifying and removing plants with undesirable characteristics (i.e., "rogues"). For example, it may be desirable to identify and remove male plants from locations where only female plants are desired. Conventional techniques of identifying and removing male plants are labor intensive and error-prone.

For example, roguing requires that each plant be carefully examined to determine whether relatively small plant parts are present or absent. In some species, sterile and fertile anthers are reliably distinguishable by manual methods only upon very close inspection, such as only if it can be confirmed that pollen is not present on the anther, which often requires a magnifying glass or other tool. This conventional inspection technique is relatively slow, requiring several seconds per plant at least. For instance, if a field has 10,000 plants and each plant takes five seconds to inspect, it would take over 13 hours to inspect the field, not counting the time to walk between plants and the like.

Moreover, humans are not reliable at identifying plants with undesirable characteristics and thus manual techniques of roguing are highly error-prone. For example, in plants like canola, whose flowers are small, the very high levels of accuracy required for commercial breeding pipelines necessitates specialized skills that only a small number of people have. Accordingly, commercial breeding pipelines are limited by the availability of these highly specialized people.

Furthermore, environmental and genetic specifics of the roguing conditions further contribute to the problem. For instance, roguing during mid-day is not as effective as roguing during the morning or afternoon due to the glare of the Sun.

SUMMARY

Aspects of the systems and methods described herein include analyzing reflections and/or emissions of electromagnetic radiation to distinguish fertile plant specimens from sterile plant specimens. In an aspect, the presence of wavelengths associated with pollen in the electromagnetic radiation reflections and/or emissions indicates a plant specimen is fertile, and the absence of wavelengths associated with pollen in the reflections and/or emissions indicates a plant specimen is sterile. In other aspects, spectral signature differences in the reflections and/or emissions that are indicative of other properties besides pollen (e.g., petal color, etc.) are utilized to distinguish between fertile and sterile plant specimens.

In an aspect, a method of distinguishing fertile plant specimens from sterile plant specimens includes receiving and/or capturing electromagnetic radiation reflected and/or emitted by a plant specimen. A hyperspectral imaging analysis is performed on the received and/or captured electromagnetic radiation to identify the presence or absence of pollen on the plant specimen. When the analysis identifies that pollen is absent from the plant specimen, an indication that the plant specimen is sterile is outputted. When the analysis identifies the presence of pollen on the plant specimen, an indication that the plant specimen is fertile is outputted.

In another aspect, a method includes receiving electromagnetic radiation reflected and/or emitted by a plant specimen and performing hyperspectral imaging analysis on it to identify spectral signatures having a wavelength in a range of about 510 nanometers to about 650 nanometers. The method outputs an indication that the plant specimen is sterile when the analysis does not identify the spectral signatures, and outputs an indication that the plant specimen is fertile when the analysis identifies the spectral signatures.

In yet another aspect, a method of analyzing a plant generally comprises receiving electromagnetic radiation reflected and/or emitted by a plant specimen; and performing an analysis on the received electromagnetic radiation to identify the presence or absence of pollen on the plant specimen based on whether the received electromagnetic radiation includes the one or more wavelengths associated with pollen.

In another aspect, a system generally comprises an optical instrument; a processor, wherein the processor is communicatively coupled to the optical instrument; a computer-readable memory device, wherein the computer-readable memory device is communicatively coupled to the optical instrument and the processor; and an image analysis application, wherein the image analysis application comprises processor-executable instructions stored on the computer-readable memory device, wherein the instructions, when executed by the processor, configure the image analysis application to: receive, via the optical instrument, electromagnetic radiation reflected and/or emitted by a plant specimen; analyze the received electromagnetic radiation via one or more hyperspectral imaging techniques to determine whether the plant specimen includes pollen on whether the received electromagnetic radiation includes the one or more wavelengths associated with pollen.

In other aspects, methods and systems are provided.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Aspects of the systems and methods described herein are configured for analyzing reflections and/or emissions of electromagnetic radiation to distinguish fertile plant specimens from sterile plant specimens. In an aspect, the systems and methods described herein are configured for detecting viable pollen using certain wavelengths of electromagnetic radiation (e.g., light inside and outside of the visible spectrum, etc.). In another aspect, the systems and methods described herein are configured for detecting spectral signature differences between fertile and sterile plant specimens regardless of pollen/anthers. Although particular embodiments are described herein, one of ordinary skill in the art will understand that any manner of filter, camera, sensor, and/or other device (e.g., smartphone with a light source, smartphone without light source, glasses, goggles, etc.) that enhances the ability to detect and/or visualize the differences in wavelengths emitted by plant specimens, pollen, flowers, and/or inflorescences may be utilized. Beneficially, the systems and methods described herein provide a simple, accurate, and high-throughput determination of whether a plant is producing pollen. In an embodiment, the systems and methods may be incorporated into at least semi-automated systems and methods of roguing plants or flowers in locations including, but not limited to, growth chambers, greenhouses, and fields by workers holding the device and/or by unmanned vehicles including, but not limited to, drones, rovers, robotic arms, tractors, and movable or fixed setups. In another embodiment, the systems and methods may be incorporated into fully automated systems and methods of roguing plants. In an embodiment, a plant specimen as used herein includes a whole plant or a part of a plant such as, but not limited to, tassel, flower, anther, and/or pollen, generated naturally and/or in vitro.

Figure 1A:
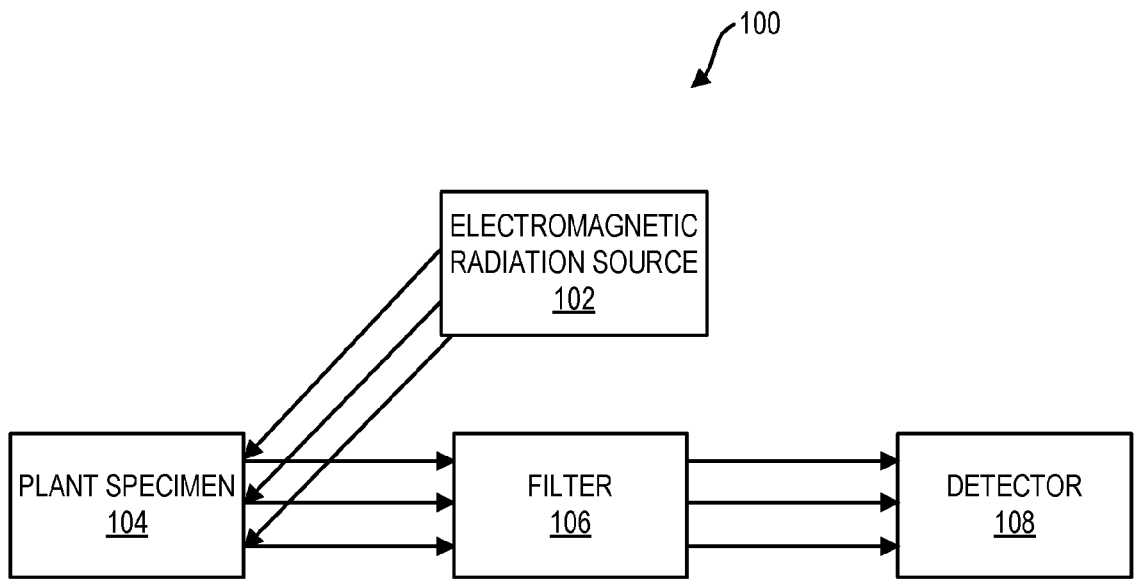
FIGS. 1A and 1B illustrate an exemplary imaging system in accordance with an embodiment.
Figure 1B:
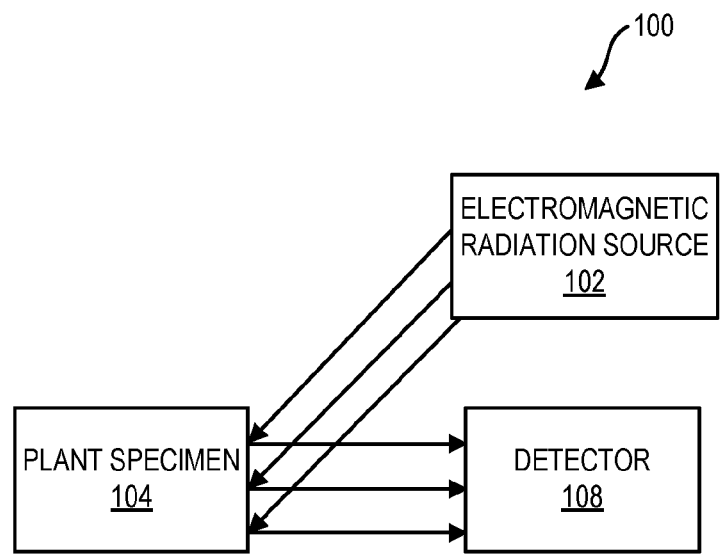

Referring now to FIGS. 1A and 1B, exemplary imaging systems and methods, generally indicated at 100, within which embodiments of the disclosure may be incorporated are illustrated. The imaging system 100 includes an electromagnetic radiation source 102 and a detector 108. In one or more embodiments, imaging system 100 includes at least one filter 106 located between a plant specimen 104 and the detector 108, as illustrated in FIG. 1A. The electromagnetic radiation source 102 is configured to generate electromagnetic radiation and irradiate the plant specimen 104 with the radiation. The electromagnetic radiation source 102 may be substantially any source capable of generating wavelengths reflected and/or emitted by a plant tissue or plant specimen, including but not limited to pollen, anther, flower, or tassel, as further described herein. Exemplary electromagnetic radiation sources include, but are not limited to, natural sources (e.g., the Sun, the Moon, etc.) and artificial sources (e.g., LED grow lights, fluorescent lights, LED ring on a smartphone, lasers, etc.).

The plant specimen 104 reflects and/or emits at least a portion of the electromagnetic radiation. For example, the plant specimen 104 may include chlorophyll that absorbs electromagnetic radiation in the red (e.g., 620-750 nm) and blue (e.g., 450-495 nm) regions of the visible light spectrum and reflects and/or emits electromagnetic radiation in the green (e.g., 495-570 nm) region of the visible light spectrum. Furthermore, the plant specimen 104 may include pollen that reflects and/or emits at least a portion of the electromagnetic radiation. The electromagnetic radiation reflected and/or emitted by pollen may be referred to as "pollen-associated wavelengths" (PAWs) (e.g., 515-525 nm, 580-590 nm, etc.) and provide a marker revealing the presence of pollen on the anthers plant specimen 104, thus indicating the plant specimen as being male-fertile.

Depending on the excitation light source, the device or software, and the plant species, the wavelength range will shift to the left or the right. In an embodiment, the "marker" is captured at 450 nm and/or 510 nm instead of 530 nm or 550 nm. In another embodiment, emissions detected below 590 nm are associated with the presence/absence of pollen. The table below provides exemplary wavebands for exemplary applications.

TABLE 1

Exemplary wavelength ranges using laser excitation at 488 nm and emission detected at 500 nm-800 nm using hyperspectral fluorescence.

| Application | Waveband-1 | Waveband-2 | Narrow Waveband-1 | Narrow Waveband-2 | Additional |
|---|---|---|---|---|---|
| Corn fertile/sterile tassel | 530-580 nm | 570-655 nm | 540-560 nm (550 nm) | 590-630 nm (610 nm) | 690 nm (Chi-b) |
| Canola fertile/sterile flower | 512-529 nm | 570-590 nm | 515-525 nm (520 nm) | 580-590 (585 nm) | 730-780 nm (Chi-a) |
| Corn pollen (live/dead) | 520-570 nm | 600-660 nm | 550-565 nm (550 nm) | 610-640 nm (630 nm) | N/A |

The filter 106 is configured to dampen or block non-PAWs within the electromagnetic radiation reflected and/or emitted by plant specimen 104 such that only or mainly PAWs reach the detector 108. The filter 106 may be any type of transparent and/or translucent material or object that selectively transmits PAWs to the detector 108. For example, filter 106 may be a lens, goggle apparatus (e.g., ski goggles, etc.), external filter, internal filter part of a device such as a smartphone, and the like. Although embodiments described herein utilize one filter 106, one of ordinary skill in the art will understand that embodiments utilizing a plurality of filters 106 are within the scope of the present disclosure.

The detector 108 is configured to detect the electromagnetic radiation reflected and/or emitted by plant specimen 104. Exemplary detectors include, but are not limited to, electronic devices, digital cameras (e.g., mobile device cameras, etc.), spectrometers, hyperspectral imagers, the human eye, and the like. In an embodiment, detector 108 detects only or mainly PAWs that are selectively transmitted by filter 106. In another embodiment, detector 108 detects both PAWs and non-PAWs reflected and/or emitted by plant specimen 104 (e.g., in the absence of filter 106) and manipulates the PAW and non-PAW signals to generate spectra and/or images highlighting (e.g., visually indicating) the location of pollen on plant specimen 104. Thus, detector 108 includes devices that register, quantify, and/or visualize the presence of PAWs and/or devices and systems configured to provide a spatial representation of surfaces/locations of plant specimen 104 associated with PAWs and surfaces/locations of plant specimen 104 not associated with PAWs.

The techniques described herein are not limited to those that function in certain regions of the electromagnetic spectrum, nor are they limited to imaging systems that provide two-dimensional or three-dimensional images representing the locations of PAWs relative to non-PAWs. The techniques can also be used with a wide range of spectrometric devices, systems, and methods, including but not limited to, hyperspectral fluorescence (e.g., detect all emitted wavelengths, from ultraviolet (UV) to visible up to near-infrared (NIR)), hyperspectral reflectance, multispectral (e.g., detect wavebands of interest), filter-based (e.g., detect a few spectra of interest), digital cameras, smartphones, hand-held spectrometer units, and the like. Broadly, these devices are optical instruments.

Figure 2:
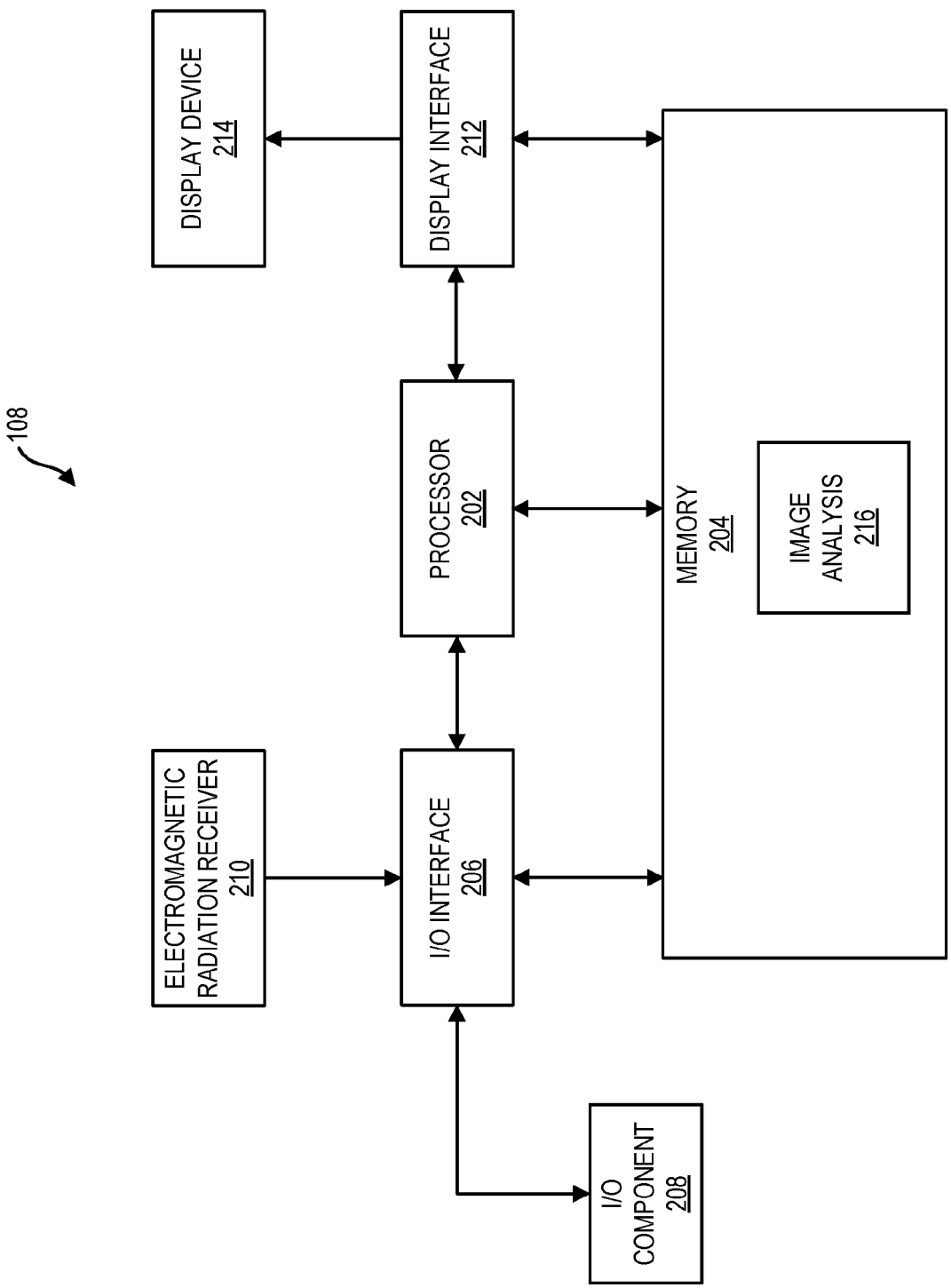
FIG. 2 illustrates an exemplary computing device architecture within which aspects of the disclosure may be implemented according to an embodiment.

FIG. 2 illustrates an exemplary architecture of an embodiment of the detector 108 (e.g., mobile computing device, tablet computing device, desktop computing device, smartphone, smart watch, smart bracelet, etc.) programmed to provide aspects of the systems and processes described herein via a software environment. In this embodiment, the detector 108 includes a processor 202, a memory 204, an input/output (I/O) interface 206 that interfaces with an I/O component 208 and an electromagnetic radiation receiver 210 (e.g., a camera, etc.), and a display interface 212 that interfaces with a display device 214. The memory 204 includes an image analysis application 216 embodied in processor-executable instructions for executing by processor 202. In this manner, the detector 108 comprises a special-purpose computing device for capturing electromagnetic radiation and performing automated image analysis to highlight (e.g., visually indicate) PAWs, in contrast to non-PAWS, reflected and/or emitted by plant specimen 104 in accordance with an aspect of the disclosure.

The processor 202, memory 204, I/O interface 206, and display interface 212 are communicatively coupled and/or electrically coupled to each other. The I/O interface 206 is communicatively and/or electrically coupled to the I/O component 208 and the electromagnetic radiation receiver 210. The processor 202 is adapted to execute processor-executable instructions stored in the memory 204 for capturing images and performing automated image analysis. The I/O interface 206 of FIG. 2 provides a physical data connection between the computing device 108 and I/O component 208 and electromagnetic radiation receiver 210. In an embodiment, I/O interface 206 is a network interface card (NIC) or modem and I/O component 208 is a telecommunications connection (e.g., Internet, Wi-Fi, etc.). Additionally or alternatively, I/O component 208 may be electromagnetic radiation source 102 (e.g., an artificial source) and/or a robotic appendage configured to be manipulated to remove plant specimens from a growing area. The display interface 212 provides a physical data connection between detector 108 and display device 214. In an embodiment, display device 214 is a touchscreen of a smartphone, tablet computing device, or the like. Additionally or alternatively, display device 214 may be a computer monitor, a goggle apparatus, or the like. In an embodiment, detector 108 includes a global position system (GPS) receiver. In another embodiment, detector 108 comprises a virtual reality headset apparatus.

Hyperspectral Fluorescence Imaging of Canola Example

Figure 3:
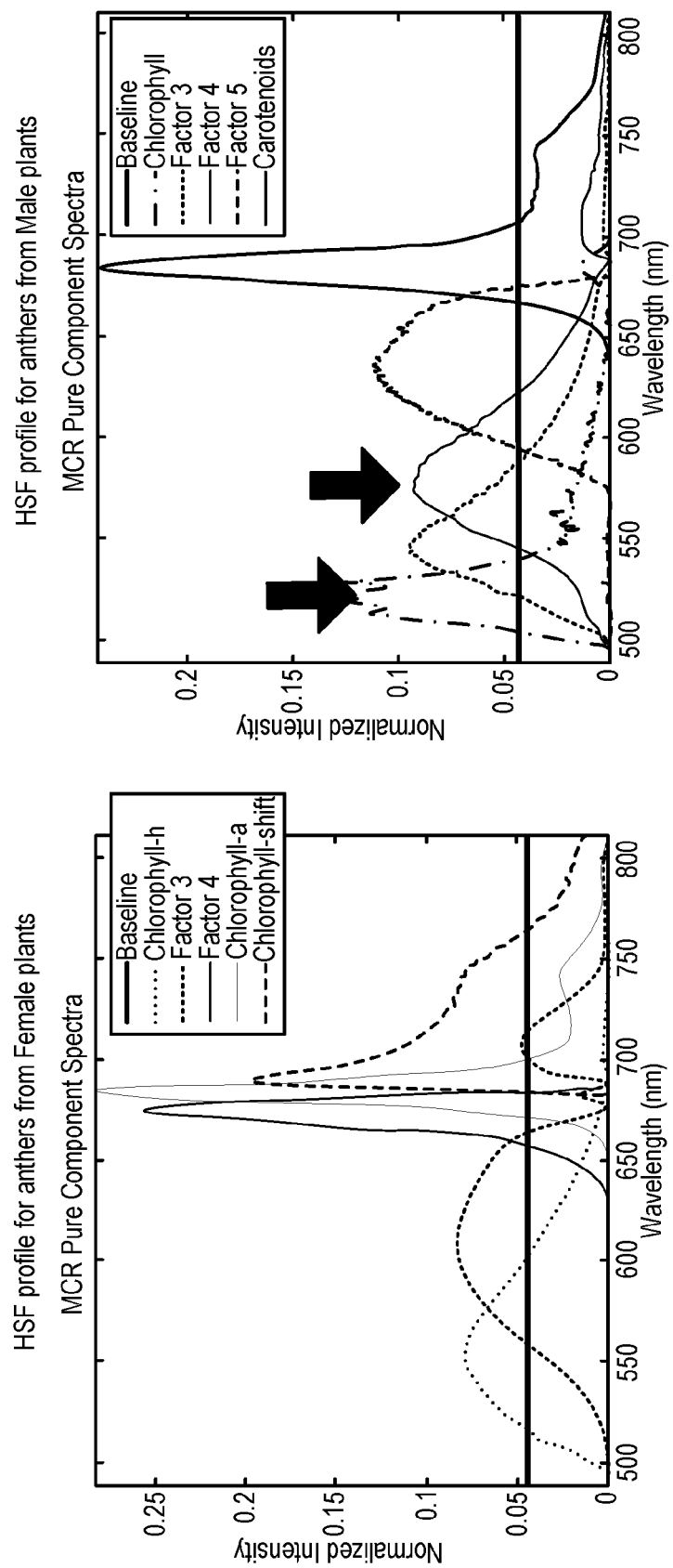
FIG. 3 illustrates a spectral signature output of a hyperspectral fluorescence analysis of pollen on canola plants in accordance with an embodiment.

FIG. 3 illustrates profiles of spectral components of electromagnetic radiation emitted by a female canola plant and a male canola plant comprising plant specimens 104 and detected by detector 108 during a hyperspectral fluorescence experiment (HSF) of system 100. The experiment reveals the presence of two pure spectral components present only in anthers from male plants emitting between 500 nm and 680 nm, with maximum peaks around 515-525 nm and 580-590 nm. In other words, the HSF analysis revealed two spectral components associated with fertile male anthers that were not present in sterile female anthers. In this embodiment, detector 108 comprised a spectrometer and an iXon Andor detector. One of ordinary skill in the art will understand that other detectors configured for portable, handheld, non-destructive analysis of plant specimens may be used (e.g., Jaz spectrometer available from Ocean Optics, Inc., etc.).

The profiles illustrated in FIG. 3, generated by the exemplary imaging system and method in FIG. 1B, reveal the different spectral signatures of female plants without pollen (left graph) as compared to male plants that contain pollen (right graph). The colors are not necessarily associated with the same spectral components in the two graphs (e.g., the red (Factor 3) and blue (Factor 4) spectral profiles in the female graph are equivalent, respectively, to the red (Factor 3) and purple (Factor 5) in the male graph). The two arrows in the graph of profiles for anthers from male plants (right graph) point to peaks (e.g., at about 520 nm and about 585 nm), which correspond to the spectral signature associated with PAWs, that are not present in the graph of profiles for anthers from female plants (left graph). As illustrated in the graph of profiles for anthers from male plants (right graph) in FIG. 3, the two spectral components are weak relative to the emission signal from chlorophyll pigments. For example, the peaks of profiles for anthers from female plants are less than a threshold value (e.g., 0.05 normalized intensity). In an embodiment, filter 106 (FIG. 1A) is utilized to block or decrease the chlorophyll signal reaching detector 108. For example, filter 106 may include, but is not limited to, filters that preferentially allow the detection of wavebands of interest, such as 515-525 nm and 580-590 nm, and block or limit the detection of non-pollen-specific wavebands.

In an embodiment, a detector 108 tuned to detect the different spectral signatures is pointed at a flower to signal whether the spectral signature of pollen is present above a certain threshold. This technique provides a way to determine whether a flower/anther contains pollen (e.g., fertile, male line) or does not contain pollen (e.g., infertile, female flower). In an embodiment, the detector comprises or is connected to a computing device (e.g., processor 202, etc.) configured to execute software that improves the detection and/or assists in imaging the spatial location of the PAW source (e.g., pollen).

UV-Excitation of Canola Example

Figure 4:
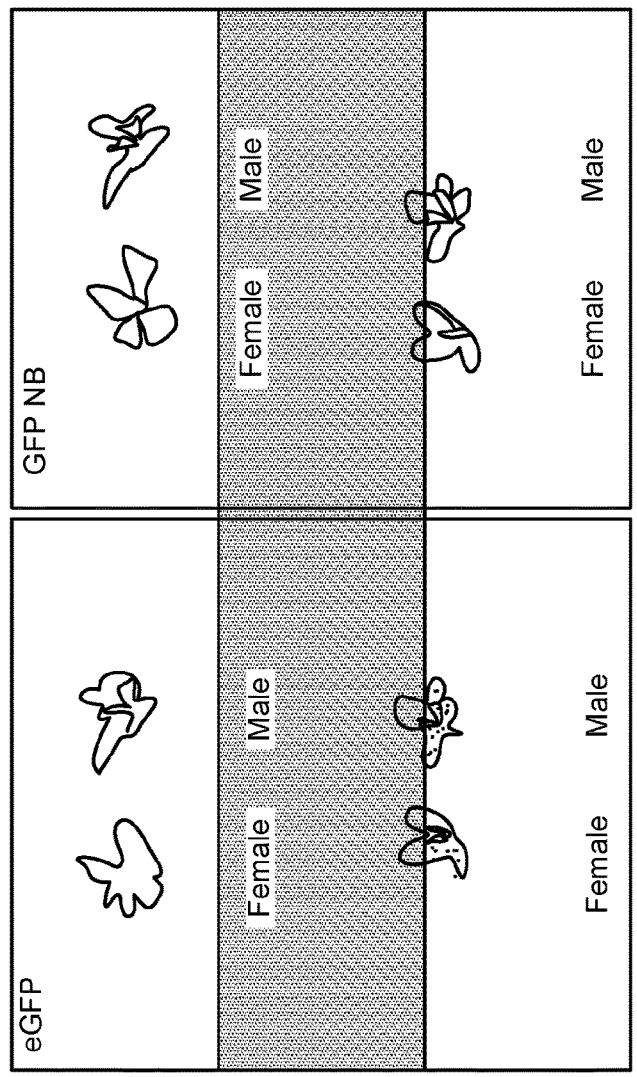
FIG. 4 illustrates images of canola plants and pollen irradiated by ultraviolet electromagnetic radiation in accordance with an embodiment.
Figure 4:
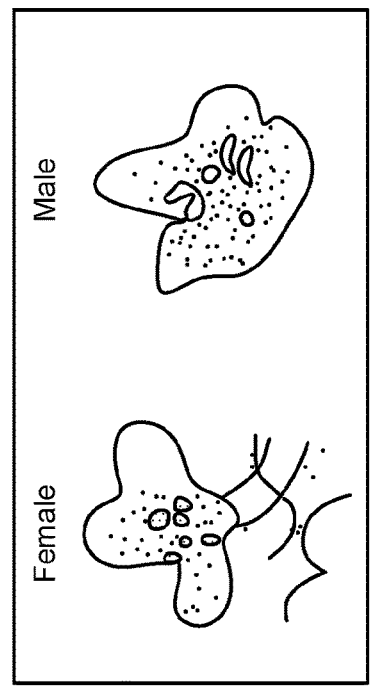

FIG. 4 illustrates images of electromagnetic radiation emitted by a female canola plant and a male canola plant comprising plant specimens 104, transmitted through filter 106, and detected by detector 108 during ultraviolet (UV) excitation of the plant specimens. In this embodiment, light source 102 comprised an X-Cite® 120 S fluorescence illuminator (e.g., 120 Watt metal halide lamp with a broad excitation spectra from ~300 nm to ~750 nm) available from Excelitas Technologies Corp. and a PentaFluar S vertical illuminator available from Carl Zeiss Microscopy GmbH. The PentaFluar illuminator included barrier filters for/or equivalent to DAPI, green fluorescent protein (GFP), TRIC, and "none" on the light path before reaching the plant specimens. The filter 106 comprised a pair of Bolle® brand ski goggles with red/orange lenses available from Bushnell Corp. The detector 108 comprised an SP-510 UZ digital camera available from Olympus Corp., a D100 digital SLR camera available from Nikon Corp., or a camera of an iPhone 5 mobile computing device available from Apple Inc.

Post-Detection Software Processing

Aspects of the present disclosure include collecting electromagnetic radiation (e.g., light) reflected and/or emitted by or emitted from a surface of plant specimen 104 with detector 108 and utilizing software (e.g., image analysis application 216 executing on processor 202, etc.) to digitally preferentially highlight (e.g., visually indicate) PAWs in contrast to non-PAWs. In an embodiment, an internal "Fade" filter of a smartphone (e.g., iPhone 5 available from Apple, Inc.) was utilized. In another embodiment, commercial software (e.g., available from Carl Zeiss Microscopy GmbH) that controls the detector 108 was used to adjust gain and exposure of the digital image that generated a false coloring for the specimens with pollen (e.g., purple-blueish or pink in FIG. 5 and FIG. 6). In such aspects, filter 106 between the plant specimen 104 and detector 108 is not necessary.

Figure 5:
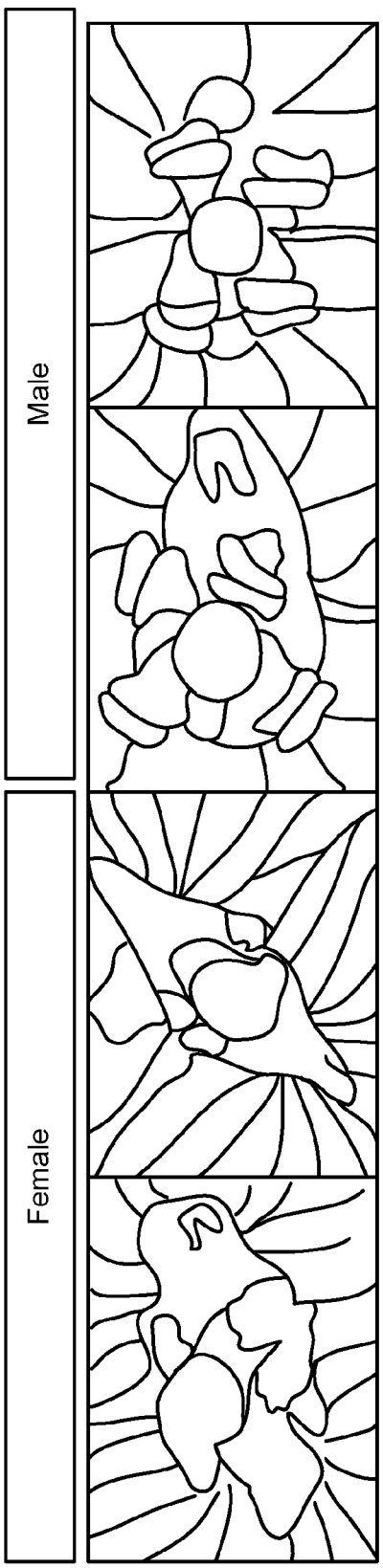
FIGS. 5 and 6 illustrate images of canola plants in which wavelengths associated with pollen are highlighted in accordance with an embodiment.

FIG. 5 illustrates images of electromagnetic radiation reflected and/or emitted by a female canola plant and a male canola plant comprising plant specimens 104 and detected by detector 108. In this embodiment, detector 108 comprised a camera (e.g., digital camera available from Carl Zeiss Microscopy GmbH) connected to a computing device. The camera captured the images and a software application (e.g., comprising image analysis application 216, a "fade" software application, etc.) was utilized to distinguish anthers containing pollen (e.g., male, two right images) from anthers lacking pollen (e.g., female, two left images) in the resulting images by manipulating image acquisition and collection parameters such as but not limited to gain and exposure.

Digitally-Manipulated White Light of Canola Example

Figure 6:
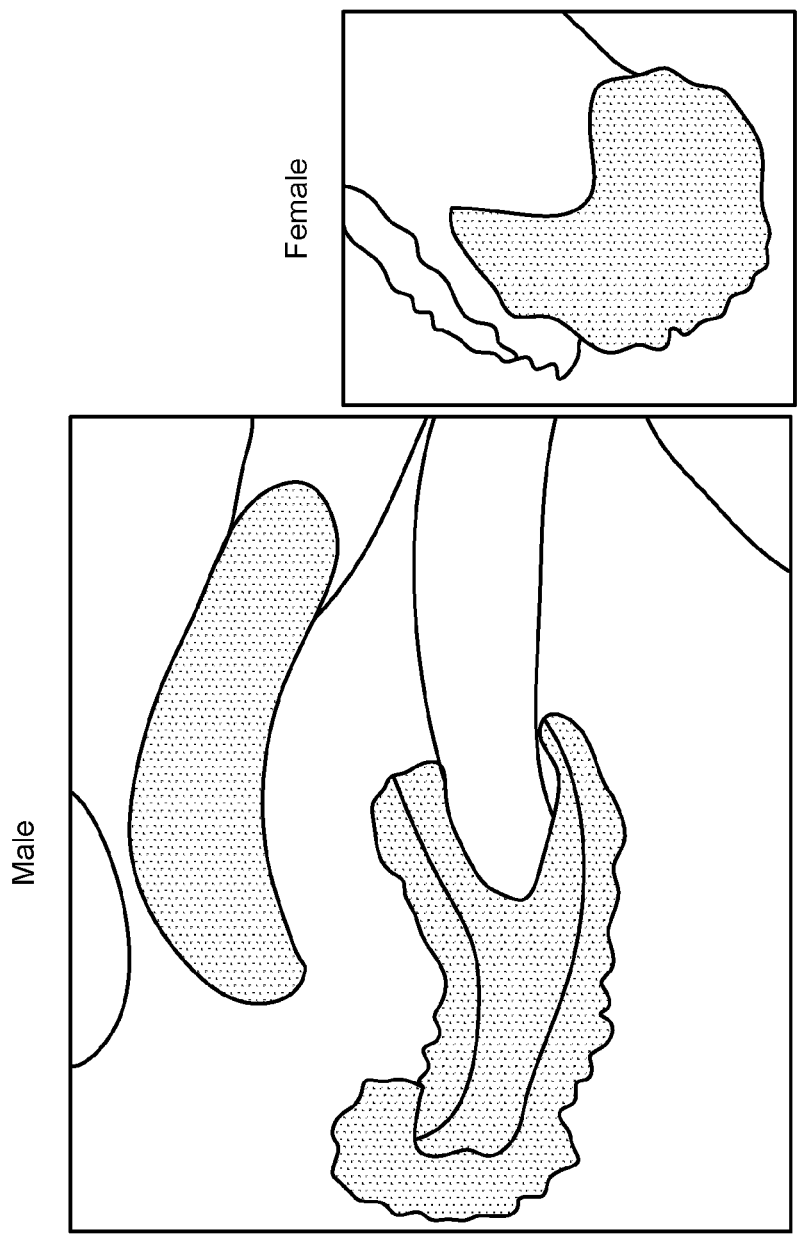

FIG. 6 illustrates images of electromagnetic radiation reflected and/or emitted by a female canola plant and a male canola plant comprising plant specimens 104 that have been manipulated by software to highlight (e.g., visually indicate) PAW signals. In this example, the plant specimens were irradiated with white light and the reflected and/or emitted wavelengths were captured and converted into a digital file (e.g., acquired with a digital microscope connected to a stereo microscope, which saved the information as an image-type file, such as JPEG). In this embodiment, electromagnetic radiation source 102 comprised a Fiber-Lite PL-800 fiber optic illuminator (e.g., 150 Watt quartz halogen lamp) available from Dolan-Jenner Industries (Setra Systems, Inc.) configured to produce a continuous spectrum of light from near ultraviolet to deep into the infrared region, which comprised a SteREO Discovery.V8 microscope available from Carl Zeiss Microscopy GmbH. The filter 106 comprised a PentaFluar S filter wheel imaging for epifluorescence from 400 nm to 720 nm. The detector 108 comprised an AxioCam HR digital high-resolution camera and AxioVision software available from Carl Zeiss Microscopy GmbH that comprised the SteREO Discovery.V8 microscope. The detector 108 utilized software (e.g., image analysis application 216 executing on processor 202, etc.) to manipulate the image to highlight (e.g., visually indicate) PAW signals. In this embodiment, the natural color of sterile flowers was established as a control (e.g., white balance), which results in the artificial coloring of pollen when present. Following alteration of the images by the software, male plants can be identified by the naked eye on a digital monitor or display.

RGB Imaging of Canola Example

Figure 7:
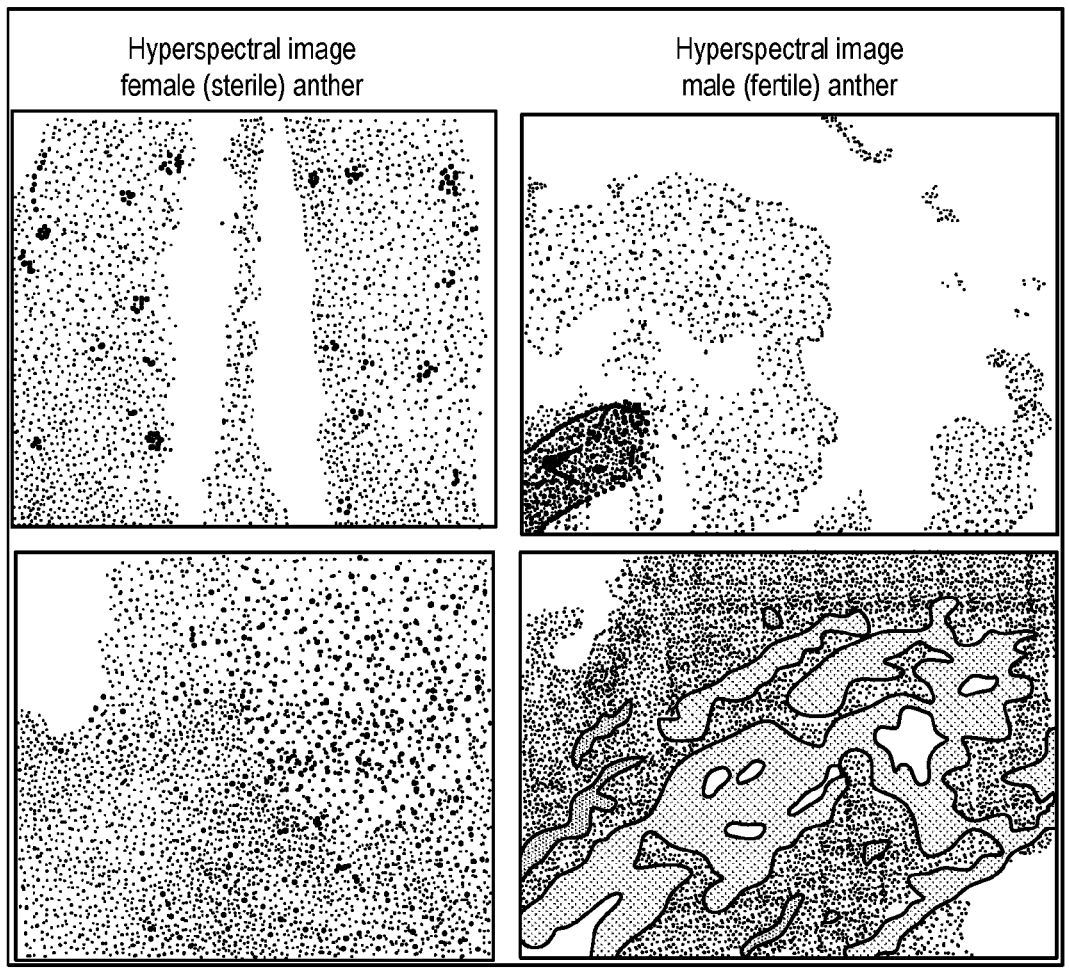
FIG. 7 illustrates images of canola plants in which spectral signatures of pollen and non-pollen surfaces are assigned red, green, and blue colors in accordance with an embodiment.

FIG. 7 illustrates images of electromagnetic radiation reflected and/or emitted by a female canola plant and a male canola plant comprising plant specimens 104 that have had red, green, blue (RGB) colors assigned to each of the spectral components of interest. The plant specimens 104 were irradiated by electromagnetic radiation source 102 and the electromagnetic radiation reflected and/or emitted by the plant specimens 104 was detected by detector 108. In this example, the detector 108 comprised a spectrometer and an iXon Andor detector to capture all the electromagnetic radiation emitted by the specimen. The raw hyperspectral data set, comprising in this case a spatial and spectra data cube, was ran through a multivariate curve resolution (MCR) software to identify the pure spectral components present in the data set. A user and/or a software GUI/script assigns red, green, and blue colors to one or more spectral components of interest and generates RGB images showing the presence/absence of PAWs. In this example, the software assigned all pure spectral components identified for female anthers the color RED and assigned the two pure spectral components present only in male anthers (e.g., the spectral components highlighted by the arrows in FIG. 3) the color GREEN. The images in FIG. 7 show the clear spectral differences between female (sterile) and male (fertile) anthers/heterotic lines. One of ordinary skill in the art will understand that other software packages, available commercially or otherwise, based on approaches other than multivariate curve resolution analysis can be utilized to analyze this type of data and generate similar results (e.g., from analysis methods used in remote sensing, field imaging, spectroscopy, or chemometrics, which can include principal component analysis or classical least squares among others).

Hyperspectral Fluorescence Analysis and Quantification of Canola Example

Figure 8:
FIG. 8 illustrates images of a hyperspectral fluorescence analysis and pollen concentration map of canola plants in accordance with an embodiment.
Figure 8:
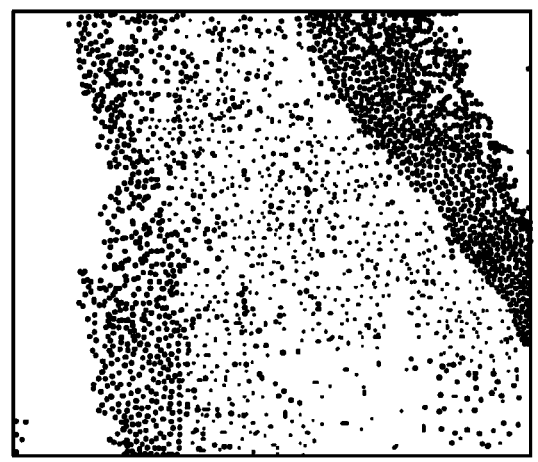
Figure 8:
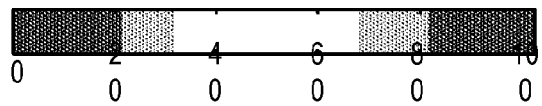

FIG. 8 illustrates an image of hyperspectral fluorescence (HSF) analysis and a concentration map of pollen. A male canola plant comprising plant specimen 104 was irradiated by electromagnetic radiation source 102 and the electromagnetic radiation reflected and/or emitted by the plant specimen was detected by detector 108, which comprised a spectrometer and an iXon Andor detector. The raw data set acquired was then analyzed using software developed by Sandia National Laboratories for Monsanto Company named rapidMCR, based on Sandia's imageMCR, which identifies and quantitates all pure spectral components present in a specimen, from wavelengths emitted between 500 to 800 nm, using multivariate curve resolution analysis. The software analyzed the detected reflections and/or emissions and generated the left image in FIG. 8, including specific spectral signatures for the presence of pollen (e.g., in green), which enables identification of male (fertile) lines from female (sterile) lines. Moreover, the software generated, based on the analysis, the right image which quantifies the amount of pollen present per anther, flower, inflorescence, and/or plant (i.e., the concentration of pollen). In this example, the detector 108 comprised a high performance hyperspectral microscope (e.g., imager) coupled with a multivariate curve resolution software (e.g., data processing and image analysis software).

One of ordinary skill in the art will understand that the detector 108 may be upgraded and/or altered, including, but not limited to, better detectors, CMOS or others, better spectrometers, different operating systems (e.g., iOS, etc.), filters, lenses, mirrors, galvanometer motors, different excitation sources, point scan or line scan imaging options, different or improved processing and analysis algorithms, and analysis tools and methods. One of ordinary skill in the art will further understand that filters (e.g., filter 106) may optionally be utilized that block or decrease the strong chlorophyll signal reaching detector 108 (e.g., sensor, detector, camera, spectrometer, etc.) and the use of narrow to very-narrow wavebands can optimize the detection of these pure spectral components in field conditions, for example.

Hyperspectral Fluorescence Imaging of Maize Examples

Although techniques described herein have described detecting pollen on canola, one of ordinary skill in the art will understand that the systems and methods described herein may be utilized to detect the presence of PAWs for other crops. As described in the exemplary embodiment below, the systems and methods described herein can detect the presence of maize (corn) PAWs and distinguish male fertile (i.e., "male") corn from male sterile (i.e., "female") corn heterotic groups utilizing a variety of filters and optical, spectrometric, and/or imaging devices.

Hyperspectral fluorescence spectroscopy reveals a spectral signature for corn pollen between ~500 nm and ~800 nm, which is especially prominent between ~525 nm and ~680 nm. Using techniques similar to those described herein for canola, the systems and methods described herein are able to image the presence of pollen in three-dimensional space utilizing the above spectral signature.

In another example, 15 fertile and cytoplasmic male sterility (CMS) tassels were harvested from each of 3 corn inbred lines. The samples are referred to as "GA", "GA-CMS1", "HI", "HI-CMS5", "94AF", and "94AF-CMS2" herein. Hyperspectral fluorescence (HSF) imaging was performed on the samples about 24 hours after harvesting. The HSF was performed at low magnification (2 mm) and pollen grains at high resolution (50 µm×50 µm×1 µm) (90 samples×5 regions×1 resolution×1 trace×4 MCR analysis) (2 pollen samples×3 inbred lines×5 traces×2 MCR analysis). Experimental details for image acquisition were as follows: 210×210 spatial resolution, 512 wavelengths, objective 2×, field of view 500 micrometers, objective 20×, field of view 50 micrometers, X step 2.4, Y step 2.4, Z step 1, Z-mode Z-sections, exposure time 0.24 milliseconds, gain 80, optical density zero, 488 nm sapphire laser at 45% power on the controller. Dark scans were acquired periodically, with no filter on the beam path. Instrument calibrations were performed at the beginning of each imaging session, controlling for light reaching the stage, light reaching the detector and beam alignment using optical density 2.5, gain 80, and 0.24 milliseconds exposure time. Calibration data, including image darks, were used by data processing and image analysis software (e.g., rapidMCR software) on the auto-processing step for removing instrument background noise, axis alignment corrections among images and a like. Each sample data set were auto-processed combined using Despike Threshold value 10, a compression of 0 or 4, with a spatial mask (Sigma 3) which was later removed for some images. Following auto-processing, the resulting raw data cubes were batch processed using analysis type Full MCR (multivariate curve resolution) without spectral guesses. Output files (e.g., Excel output files) were automatically generated showing the number of factors/or pure spectral components discovered by MCR analysis, displaying the mean intensity (counts), median and variance for each factor/or pure spectral component, per trace, per image or combined images, for each large sample auto-processed data set. A summary showing the average intensity values/counts for each factor/or pure spectral component found for each large sample data set was also generated. The detector sensitivity was 4 photons to generate 1 count. Plots were also automatically generated with information on Eigen values, PCA results, convergence criterion, MCR results, Concentration correlations, MCR concentration maps, Residuals PCA scores and loads, and Percent Variance. RGB images were generated from the MCR results by attributing a color (red, green, or blue) to a factor or groups of factors/pure spectral components. Concentration maps for each factor/or pure spectral component present in a sample were generated using a similar approach, being blue tones associated with lower concentration values and orange and red colors with higher concentration values or intensities.

Figure 9A:
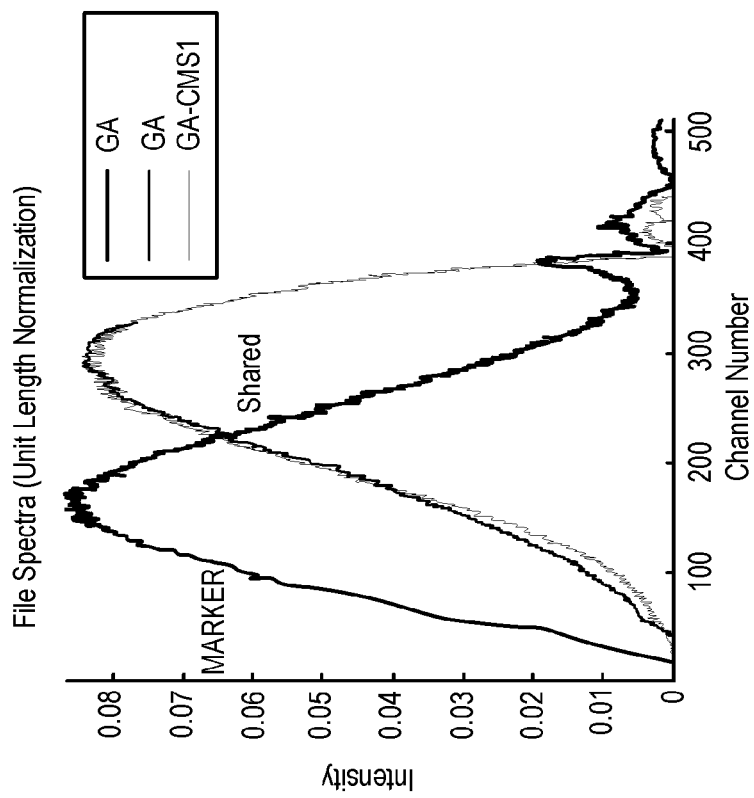
FIGS. 9A-B illustrate spectral signature outputs of maize plants in accordance with an embodiment.
Figure 9A:
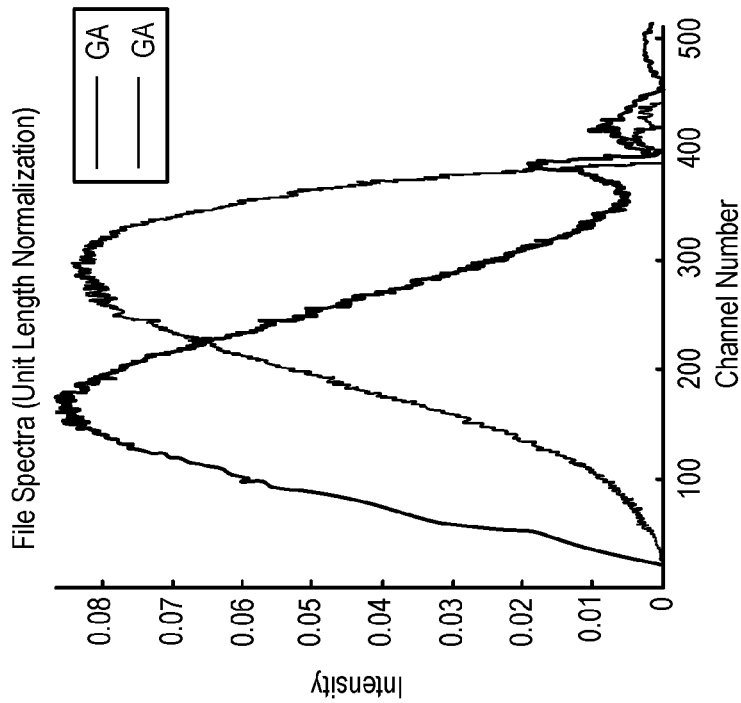
Figure 9B:
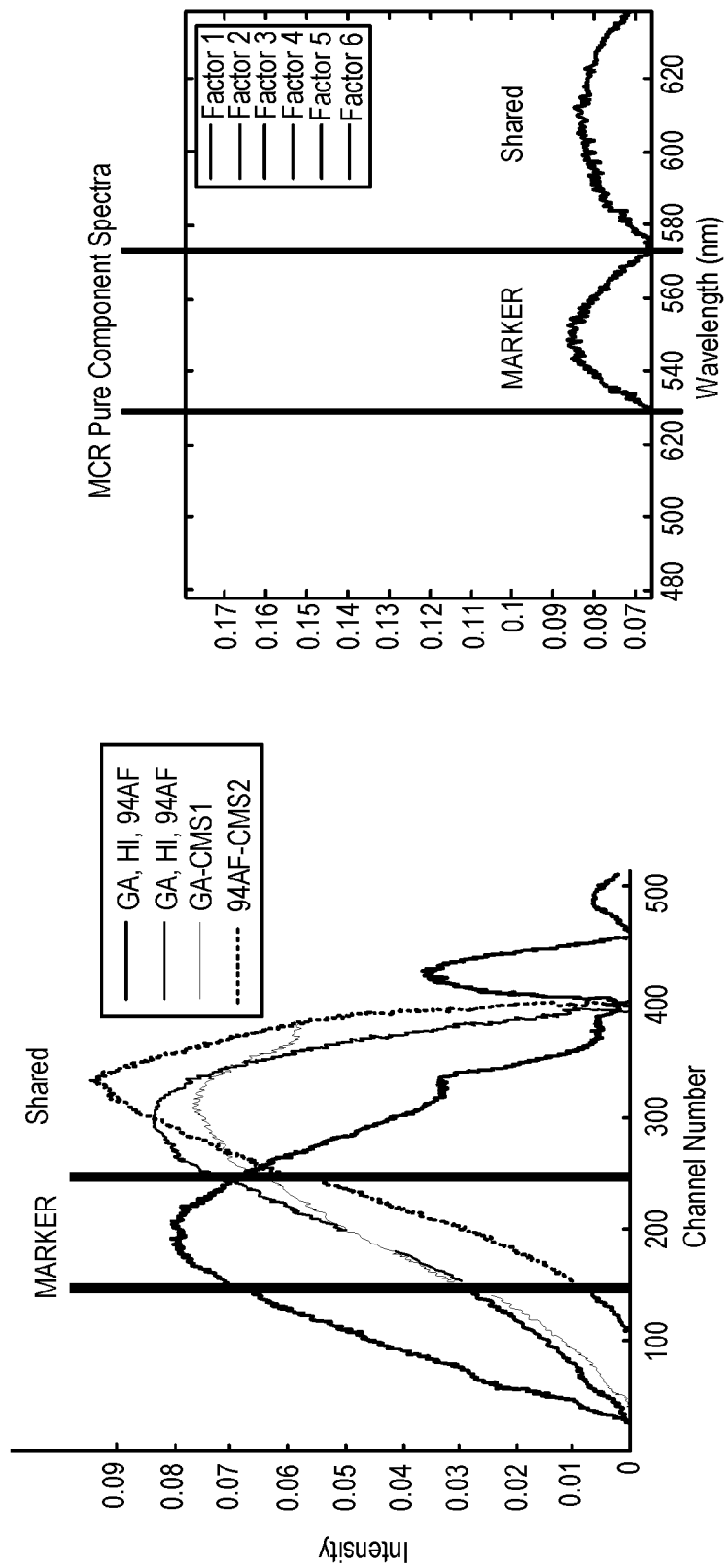

As illustrated by FIG. 9A, a spectral library software tool confirms that fertile tassels consistent show a spectrum (e.g., gray) at about 530 nm to about 580 nm, indicated as "MARKER" in FIG. 9A. This spectrum (e.g., marker) is absent in all CMS plants. As illustrated by FIG. 9B, the spectra shared by fertile and CMS tassels can shift a few nanometers in different samples, but never overlaps with the MARKER spectrum. According to the example, the presence of the MARKER spectrum and the "Shared" spectrum indicates a fertile tassel, the presence of only the "Shared" spectrum indicates a CMS tassel (e.g., CMS1 and CMS2), and the absence of the MARKER spectrum and the Shared spectrum indicates a CMS tassel (e.g., CMS5). Table 2 provides a characterization of the shared spectrum and MARKER spectrum.

TABLE 2 based on a 488 nm excitation using the HSF system

| Spectral specifications | Shared spectrum | Marker spectrum |
| --- | --- | --- |
| Wavelength region in VIS | ~500 nm to ~690 nm | ~500 nm to ~690 nm |
| Wavelength region above noise | ~540 nm to ~670 nm | ~515 nm to ~590 nm |
| Wide waveband | ~570 nm to ~655 nm | ~530 nm to ~580 nm |
| Narrow waveband | ~590 nm to ~630 nm | ~540 nm to ~560 nm |

Pollen-Independent Techniques

Additionally or alternatively, the systems and methods described herein may utilize spectral signature differences indicative of other plant properties besides pollen to distinguish between male and female plant specimens 104. For example, regardless of pollen/anthers, the petals of canola flowers have different spectral signatures and/or reflectance properties (e.g., based on color, etc.) depending on whether they are of male or female germplasm.

Figure 10:
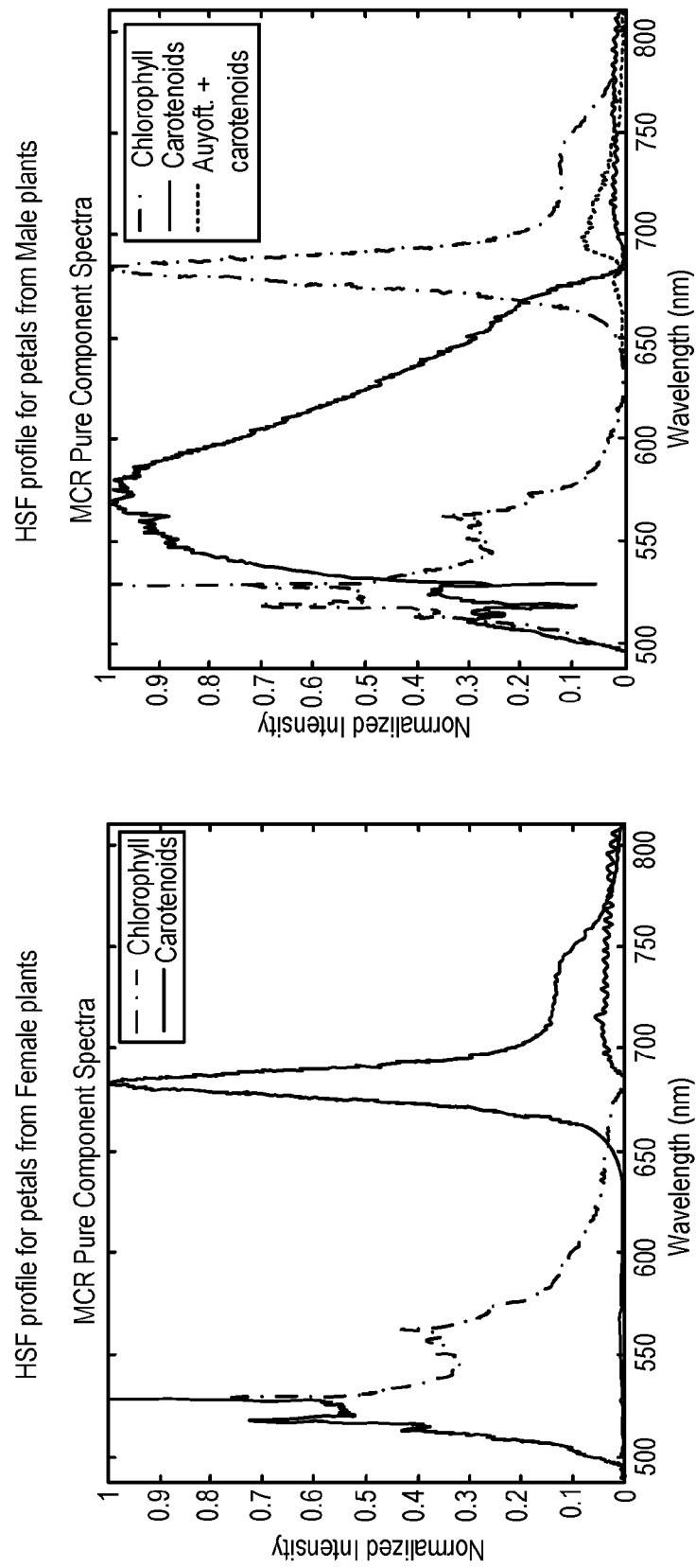
FIG. 10 illustrates a spectral signature output of a hyperspectral fluorescence analysis of canola plant petals in accordance with an embodiment.

As illustrated in FIG. 10 by the profiles of spectral components of electromagnetic radiation reflected and/or emitted by a female canola plant and a male canola plant comprising plant specimens 104 and detected by detector 108 during a hyperspectral fluorescence experiment of system 100, the presence of spectral component specific to petals of male flowers is emitted between 500 nm and 680 nm, with a stronger signal around 530-650 nm. Accordingly, the systems and methods described herein may utilize any filter capable of enhancing the wavelengths of the spectral component specific to petals of male flowers (e.g., about 530 nm to about 650 nm, etc.) to distinguish the organs of female plant lines from the organs of male plant lines, regardless of the presence of pollen.

In an embodiment, analytical tools (e.g., portable or handheld computing devices, etc.) detect the secondary metabolites responsible for the differences in spectral signatures. Moreover, by assigning different RGB colors to the spectral component of interest (e.g., "Autofl+carotenoids" in FIG. 10) and to the two other spectral components common to both male and female lines (e.g., "Chlorophyll" and "Carotenoids" in FIG. 10), systems and methods described herein can image (e.g., detect, identify, analyze, etc.) and distinguish the organs of male plants from the organs of female plants.

In an embodiment, the systems and methods described herein optimize the detection of wavelengths of the spectral component specific to petals of male flowers (e.g., about 530 nm to about 650 nm) in field conditions by utilizing filter 106 to block or decrease the strong chlorophyll signal reaching detector 108 (e.g., sensor, detector, camera, spectrometer, etc.). In another embodiment, the systems and methods described herein optimize the detection of wavelengths of the spectral component specific to petals of male flowers (e.g., about 530 nm to about 650 nm) in field conditions by utilizing processing and analysis software (e.g., image analysis application 216 executing on processor 202, smartphone digital camera capabilities, etc.) to detect a narrow to very-narrow waveband. Moreover, image processing and analysis algorithms and software can further improve the output. Aspects of the present disclosure further enhance the distinction between the organs of male plants and the organs of female plants by physical pre-detection filtering (e.g., filter 106) and/or other types of software (e.g., image analysis application 216 executing on processor 202, etc.) that better capture the surface texture and pigmentation differences. By associating the germplasm of a plant with its flower color, aspects of the present disclosure are, in effect, genotyping the plant. Exemplary filters include, but are not limited to, Semrock EdgeBasic BLP01-647R, free plastic, plexiglass-like filters available from Chroma, internal smartphone (e.g., iPhone) filters, and FSQ-BG38 available from Newport, and the like.

Images of electromagnetic radiation reflected and/or emitted by a female plant specimen 104 and a male plant specimen 104 that have had RGB colors assigned to each of the spectral components of interest can also be obtained by the present invention. In this embodiment, the plant specimens 104 were irradiated by electromagnetic radiation source 102 and the electromagnetic radiation reflected and/or emitted by the plant specimens 104 was detected by detector 108. In this example, the detector 108 (e.g., image analysis application 216 executing on processor 202, etc.) assigned the two pure spectral components common to both female and male petals ("Chlorophyll" and "Carotenoids") the color RED and assigned the pure spectral component present only in male petals (e.g., "Autofl+carotenoids") the color GREEN. The images showed the clear spectral differences between female flowers and male flowers of these heterotic groups using hyperspectral image analysis.

Images of HSF analysis and concentration maps of a marker component can also be obtained. In this embodiment, a male plant specimen 104 was irradiated by electromagnetic radiation source 102 and the electromagnetic radiation reflected and/or emitted by the plant specimen was detected by detector 108. The detector 108 (e.g., comprising a spectrometer, iXon Andor detector, and imageMCR analysis software) performed an HSF analysis of the detected reflections and/or emissions and generated the hyperspectral images on the left in FIG. 13 including presence of a pure spectral component (in green) only identified in petals of male (fertile) lines. Moreover, the detector 108 generated, based on the analysis, concentration maps that represent the distribution of the petals of male flowers at different concentrations.

Images of electromagnetic radiation reflected and/or emitted by a female canola plant and a male canola plant comprising plant specimens 104 and detected by detector 108 can also be obtained. In this embodiment, detector 108 comprised a digital camera available from Carl Zeiss Microscopy GmbH. Visible light reflected and/or emitted off the petals of the plant specimens was captured by the computing device controlling the image acquisition device, which executed a software application to enhance the differences between male and female plant specimens such that they are visually distinguished. The petals of the male plant specimen are more vibrantly yellow than the petals of the female plant specimen. Also, the pollen present in the anthers is artificially colored showing in this embodiment a pink color. One of ordinary skill in the art will understand that other devices, such as but not limited to digital cameras and smartphones, are capable of achieving the same visual results.

Images of another example in which electromagnetic radiation was reflected and/or emitted by female plants and male plants comprising plant specimens 104 and detected by detector 108 are also described herein. In this embodiment, detector 108 comprised a camera on an iPhone 5 mobile computing device. The plants in were photographed in a greenhouse under natural light (e.g., the Sun comprised electromagnetic radiation source 102) and in a growth chamber under grow lamps (e.g., the growth lamps comprised electromagnetic radiation source 102). The petals of the male plants are more vibrantly yellow than the petals of the female plant specimens. Thus, in certain embodiments, the detector 108 can comprise a smartphone (e.g., iPhone) and the user can manipulate the filter settings on the device to determine which filter(s) highlights the anthers. These images can then be used to differentiate male fertile from male sterile anthers (i.e., plants used as "females" only) in the manner described above.

Figure 11:
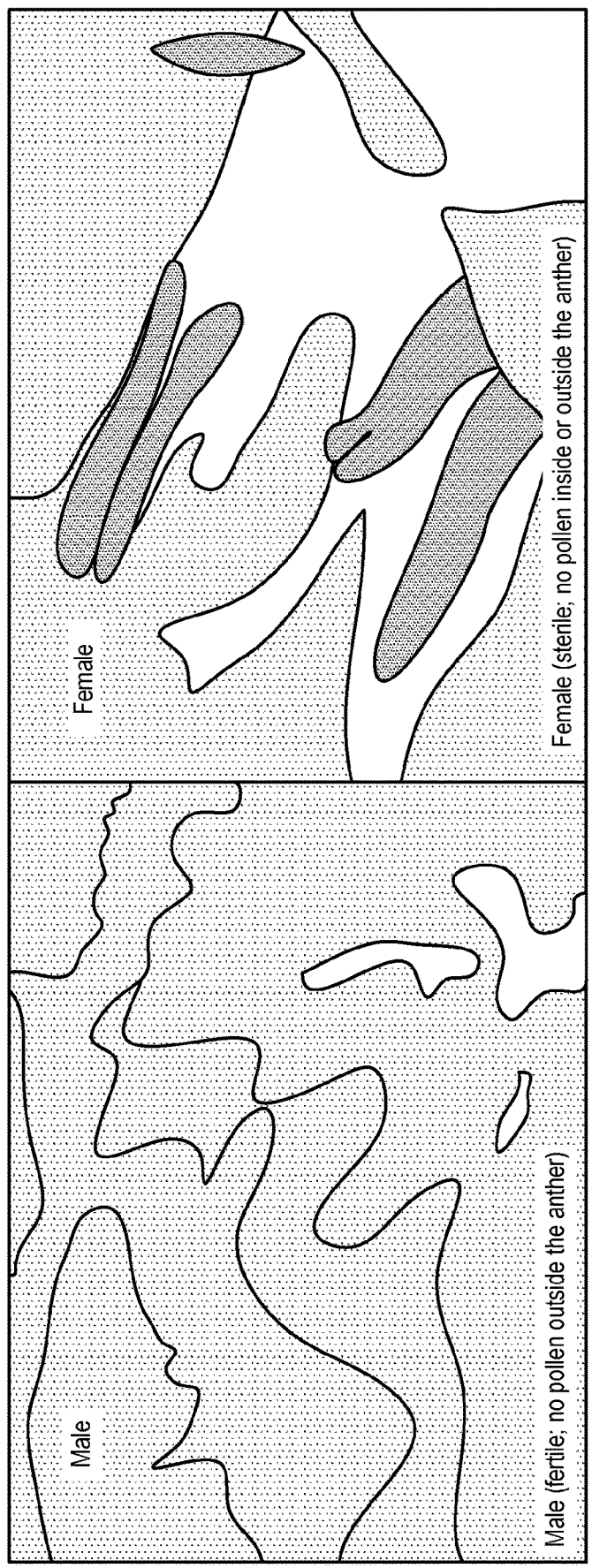
FIG. 11 illustrates images of canola plants irradiated by ultraviolet electromagnetic radiation in accordance with an embodiment.

FIG. 11 illustrates images of an example in which ultra-violet electromagnetic radiation was reflected and/or emitted by a female plant specimen 104 and a male plant specimen 104 and detected by detector 108. In this embodiment, electromagnetic radiation source 102 comprised an X-Cite® 120 S fluorescence illuminator available from Excelitas Technologies Corp. In this embodiment, the systems and methods herein are able to distinguish differences in the light emitted from male anthers/flowers from the light emitted from female anthers/flowers in the absence of pollen by utilizing the ultra-violet excitation, one or more filters 106 in the path of the emitted visible light, and detector 108 (e.g., a digital camera, mobile computing device, etc.) to visualize the image. In this embodiment, filter 106 comprised an excitation bandpass filter 470/40 and an emission filter 525/50. Notably, anthers from male (fertile) flowers without pollen under the conditions in this embodiment can still be distinguished from anthers of female (sterile) flowers without pollen due to the absence of fluorescence signal within the wavelength range selected for this purpose.

Reach Extender

Figure 12A:
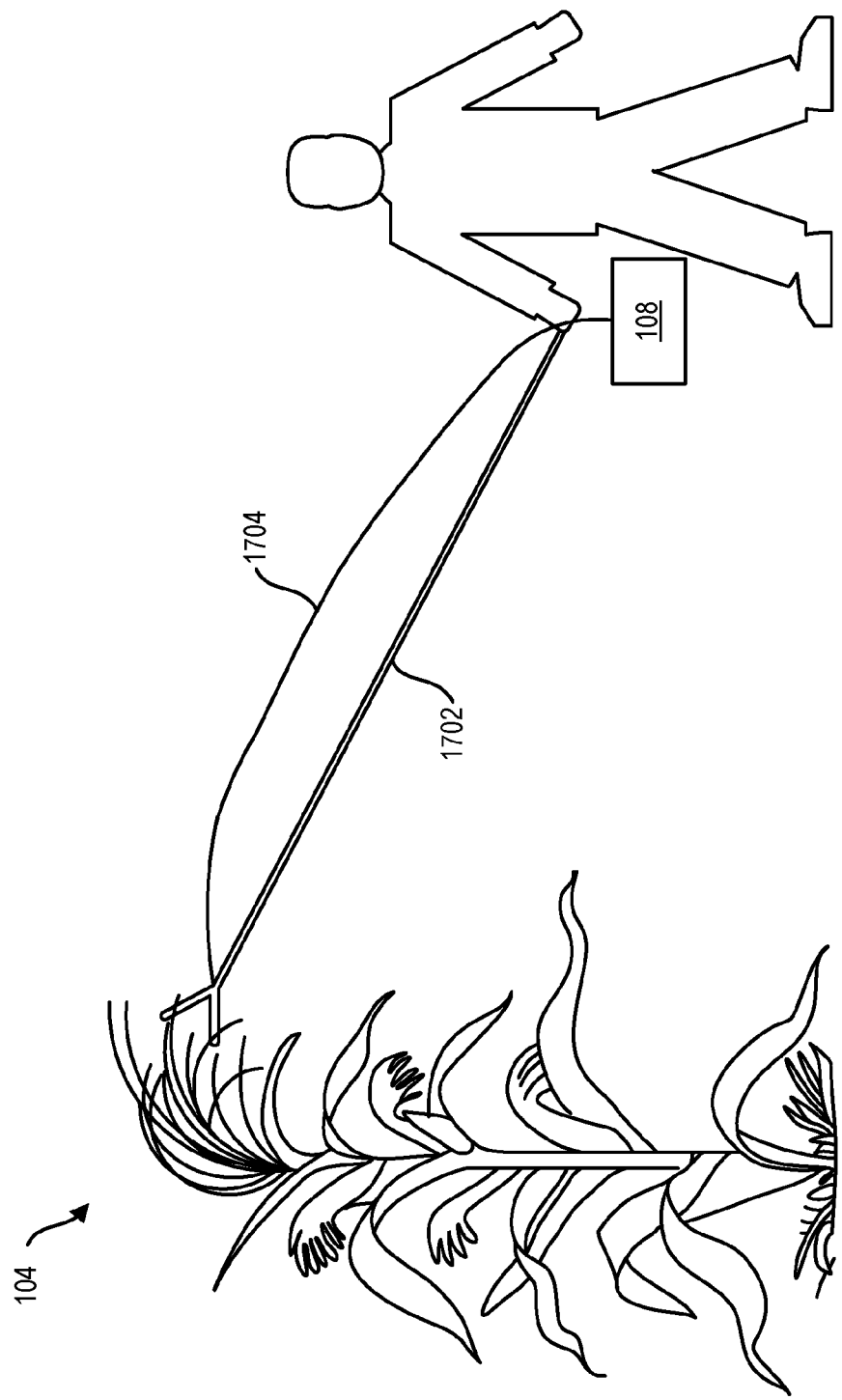
FIGS. 12A-B illustrate another exemplary imaging system in accordance with an embodiment.

FIG. 12 illustrates an exemplary reach extender system within which embodiments of the disclosure may be incorporated. The reach extender system includes a reach extender (e.g., grabber arm, "helping hand") 1702 and an optical fiber 1704 extending from a jaw end of reach extender 1702 to detector 108 (e.g., a spectrometer, etc.).

Figure 17:
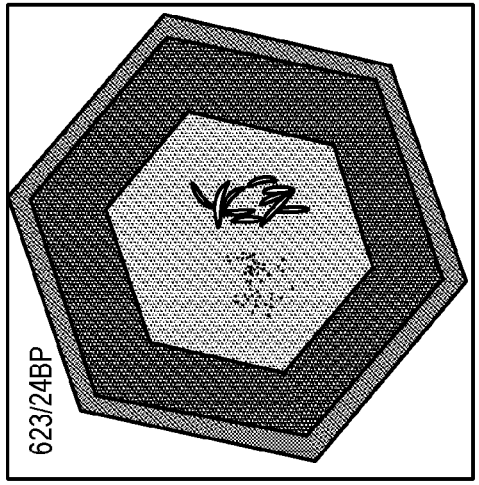
Figure 17:
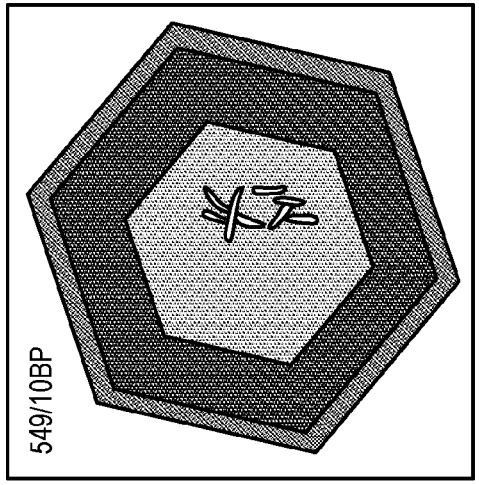
Figure 17:
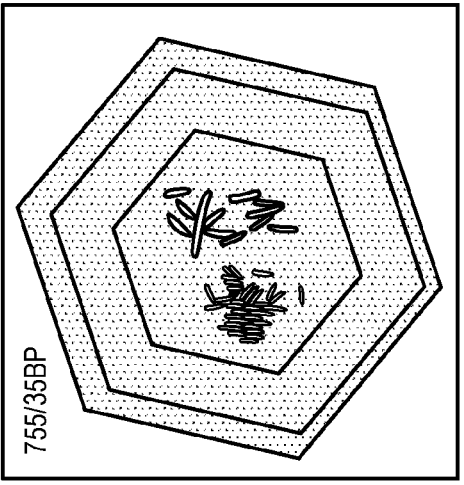
Figure 17:
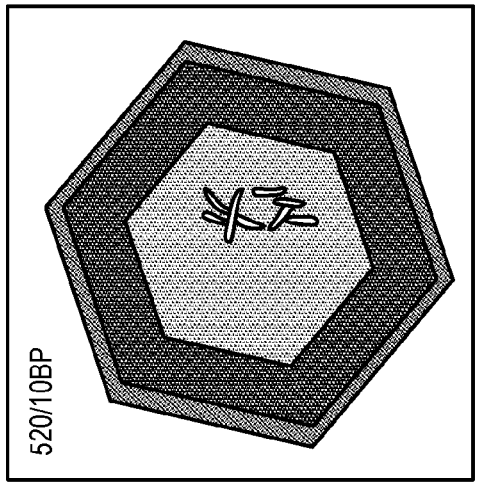
Figure 17:
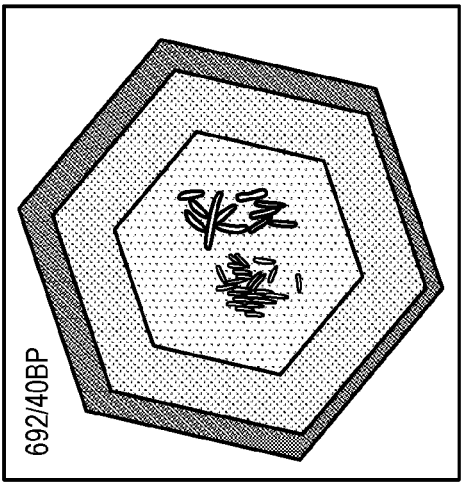

In an embodiment, reach extender 1702 comprises a handheld mechanical tool configured to increase the range of a person's reach when grabbing objects. In an aspect, reach extender 1702 comprises a pole portion comprised of metal and/or plastic having a length of about three feet, a handle at one end and a pair of jaws (e.g., a clamp) at the other end. The handle includes a trigger that, when activated, closes the jaws, such as via a lever-and-spring system within the pole. In an embodiment, an end of optical fiber 1704 is integrated into a pad of a jaw of reach extender 1702. Although a human is illustrated in FIG. 17, one of ordinary skill in the art will understand that the reach extender system may be utilized with unmanned vehicles including, but not limited to, drones, rovers, robotic arms, tractors, and movable or fixed setups, and the like.

Additional Results

Figure 13:
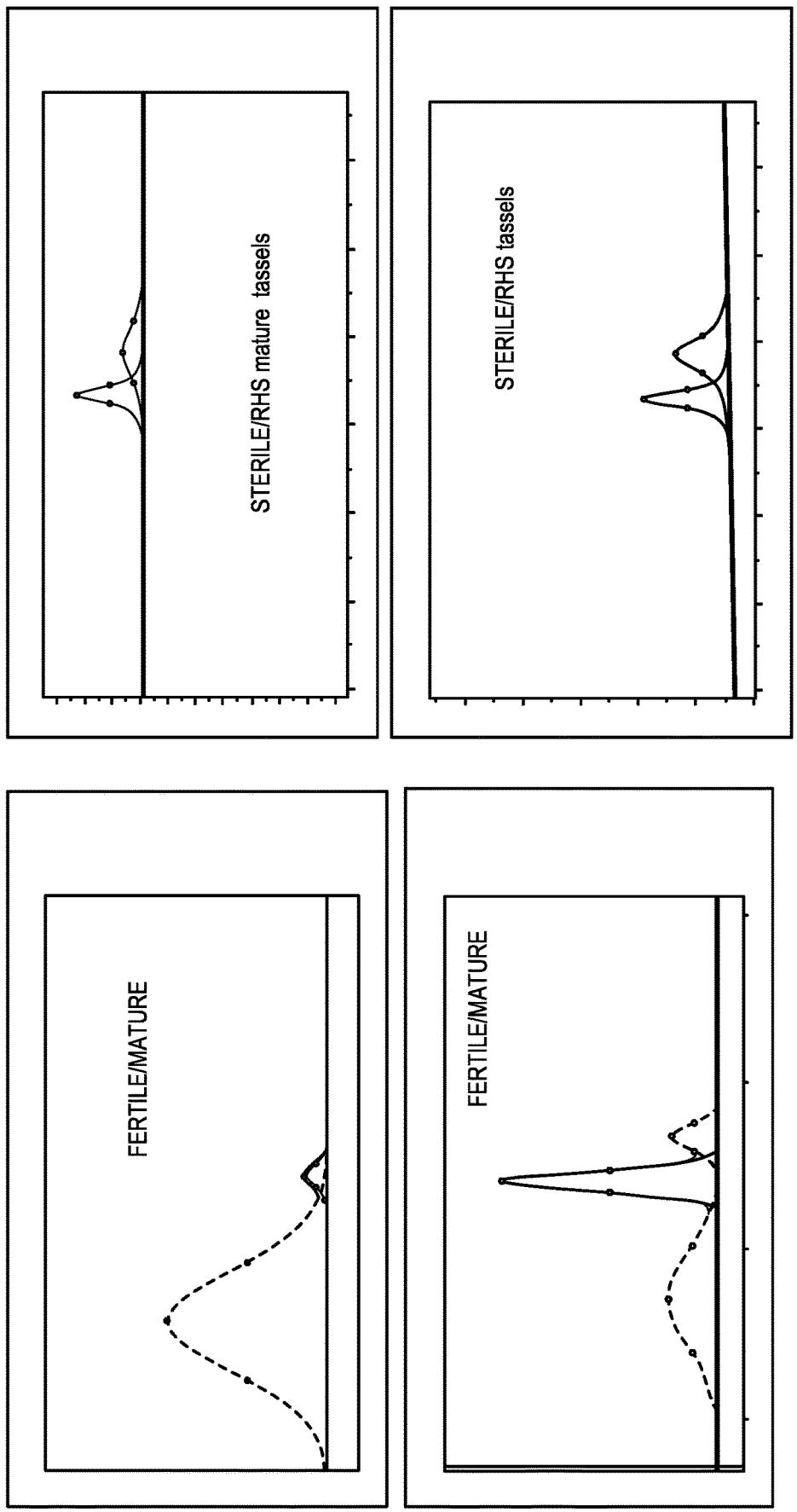
FIGS. 13-18 illustrate results obtained via the systems and methods described herein.

FIG. 13 illustrates profiles of data acquired by a spectrometer with a 405 nanometer LED for corn tassels that are fertile and corn tassels belonging to the roundup hybridization system (RHS) group. The spectra of electromagnetic radiation acquired by the spectrometer were deconvoluted by GRAMS/AI.

Figure 14:
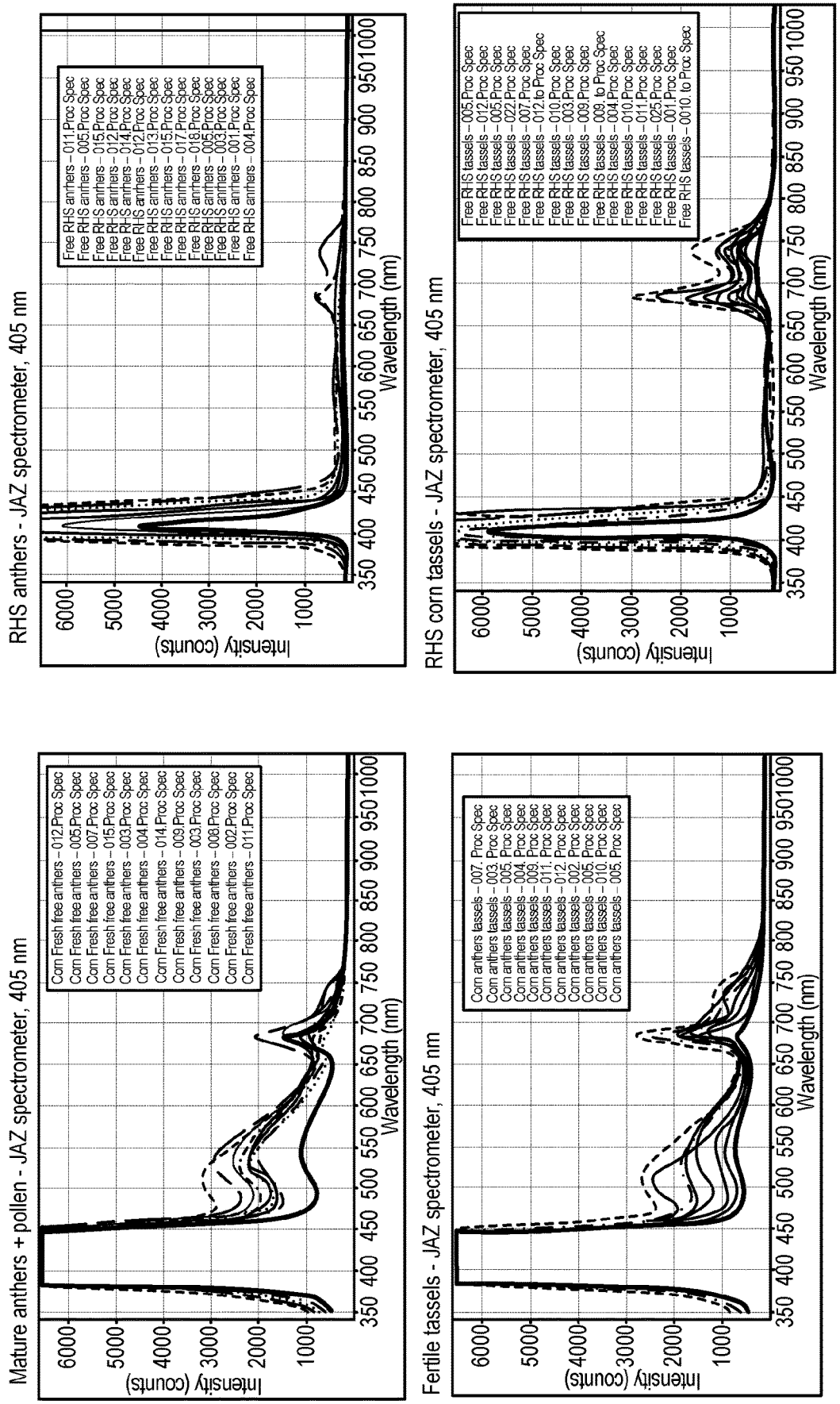

FIG. 14 illustrates raw data acquired by a Jaz spectrometer. In this manner, results are available with a handheld spectrometer in the field without the need for specialized laboratory equipment or data processing in accordance with an aspect of the disclosure.

Figure 15:
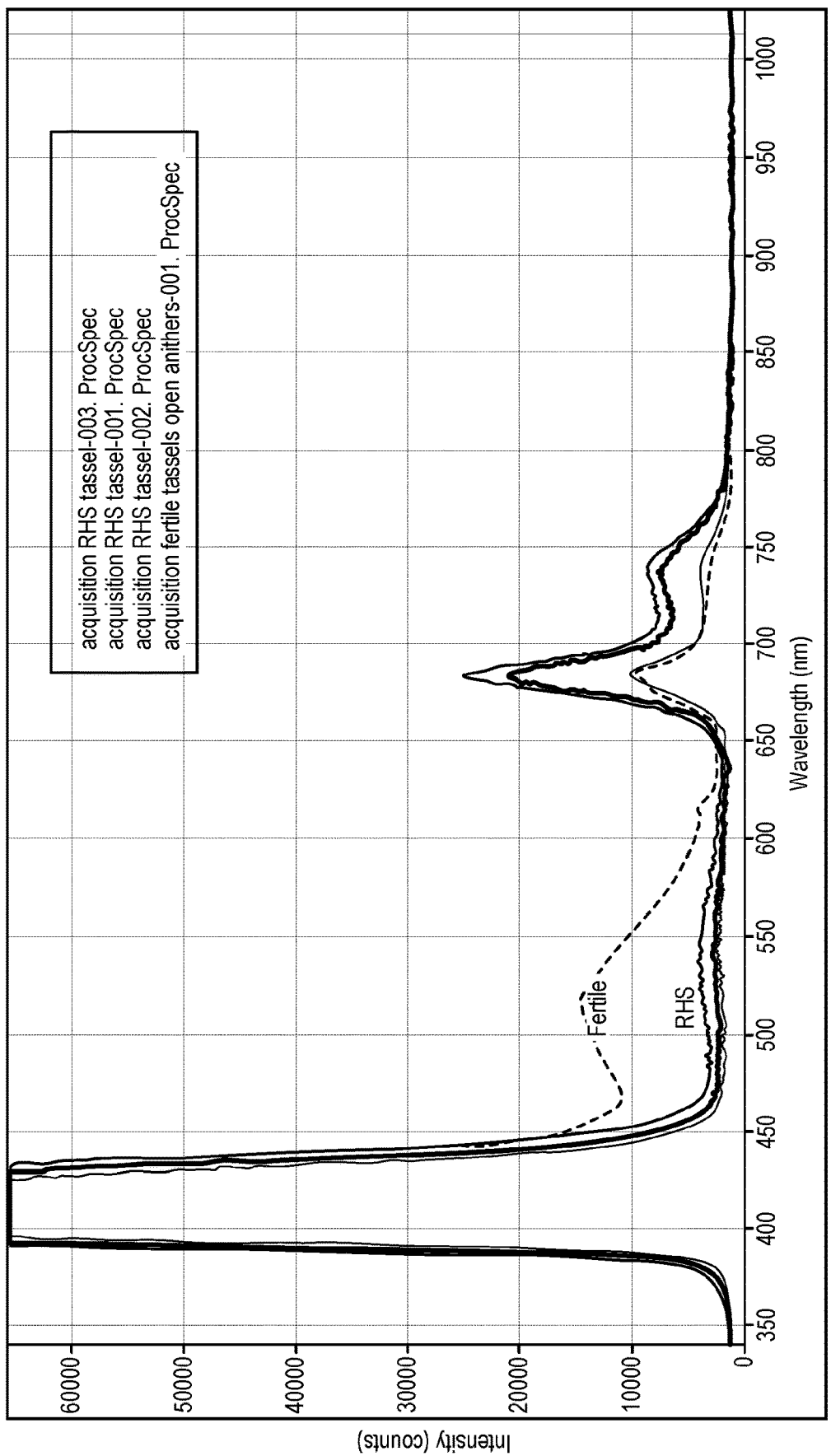

FIG. 15 illustrates profiles of data acquired by a spectrometer with a 405 nanometer LED for corn tassels that are fertile and corn tassels belonging to the RHS group. In this embodiment, a user held the optical probe and the distance to the plant specimen was not constant.

Figure 16:
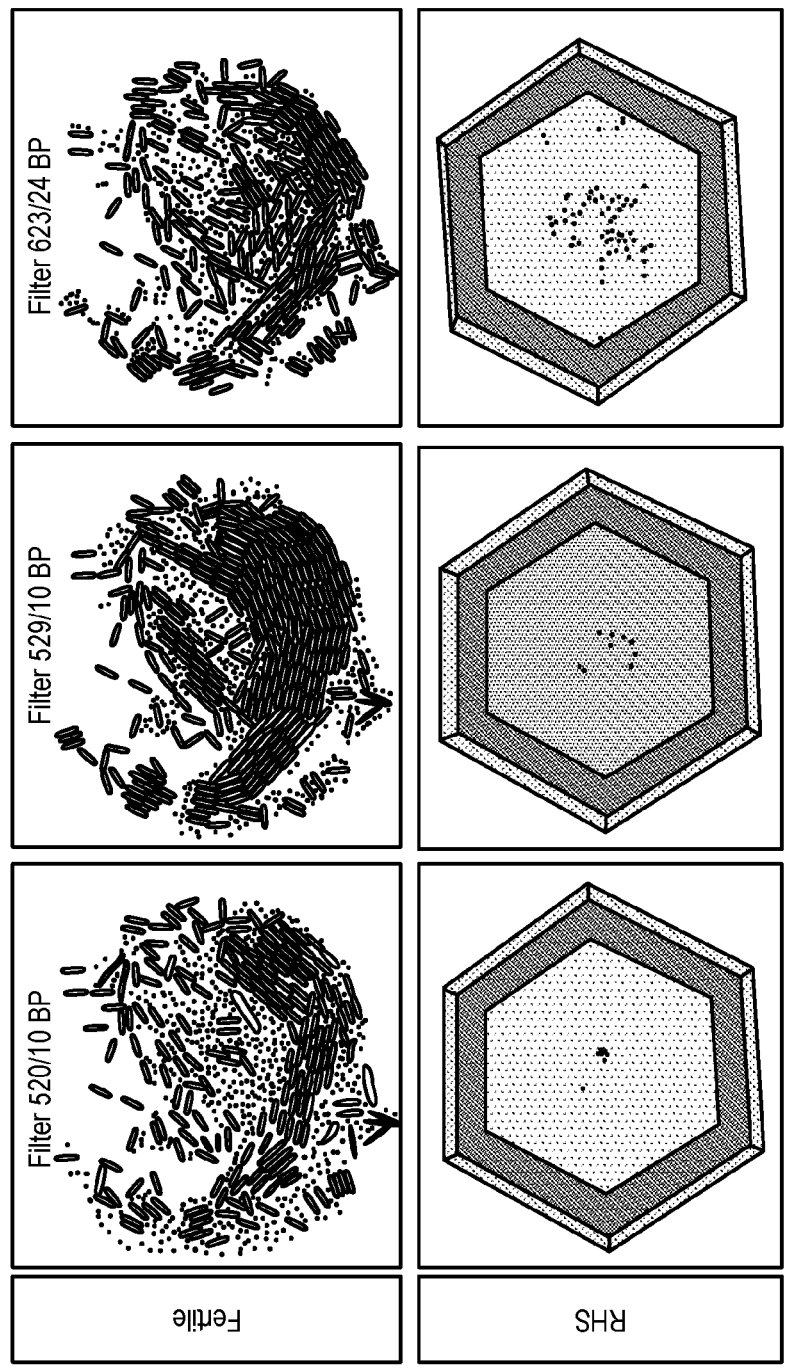

FIG. 16 illustrates data acquired for corn tassels that are fertile and corn tassels belonging to the RHS group utilizing a 520/10 BP filter, a 549/10 BP filter, and a 623/24 BP filter that illustrates the range of wavelength shift.

FIG. 17 illustrates data acquired for sterile and fertile corn anthers at 460 nanometers with a wavelength range of about 510 nanometers to about 790 nanometers. In this manner, one of ordinary skill in the art will understand that the range of wavelengths is dependent upon the specimen developmental stage, excitation source, and/or device/system.

Figure 18:
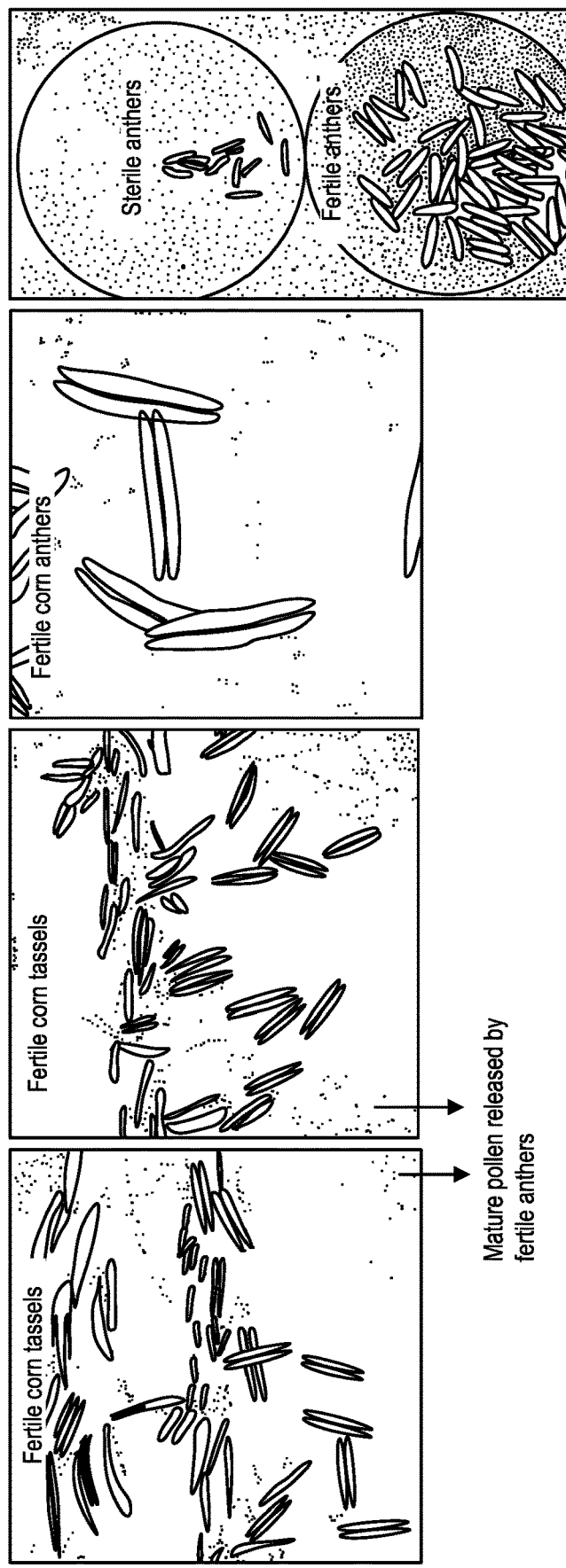
Figure 19A:
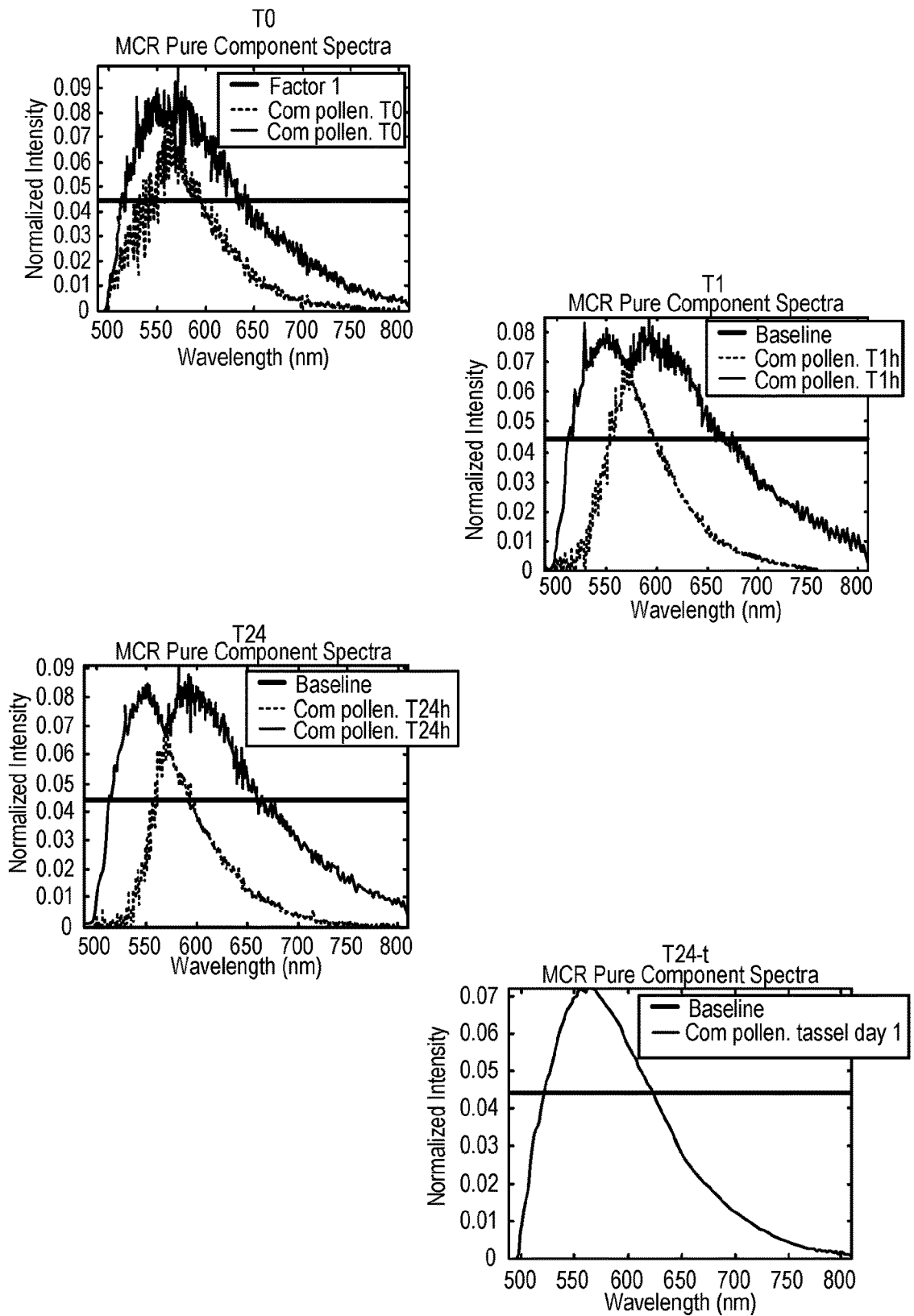
FIG. 19A illustrates spectral data at T0, T1, T24, and T24-t of corn pollen.
Figure 19B:
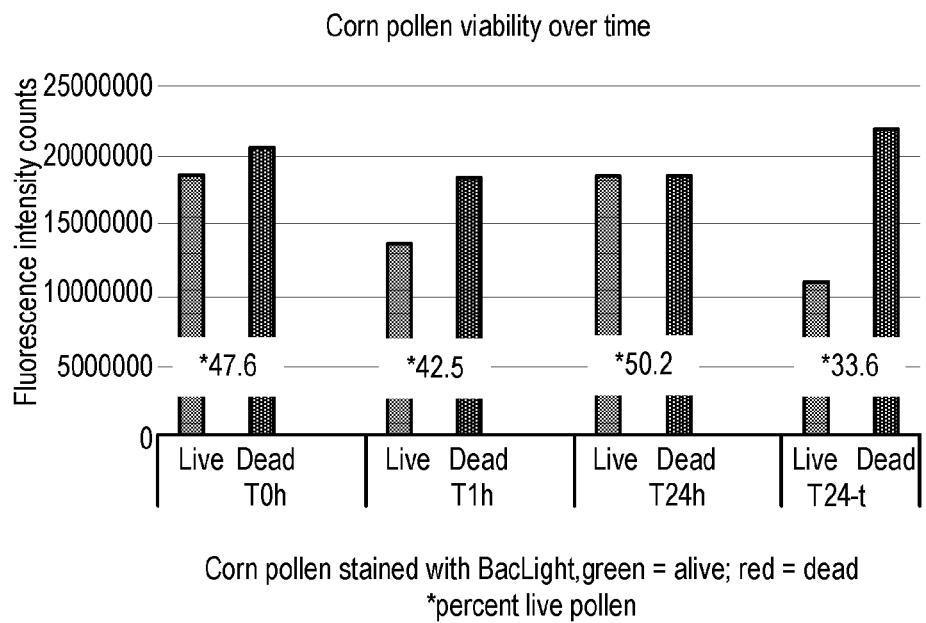
FIG. 19B illustrates a chart of corn pollen viability over time.
Figure 19C:
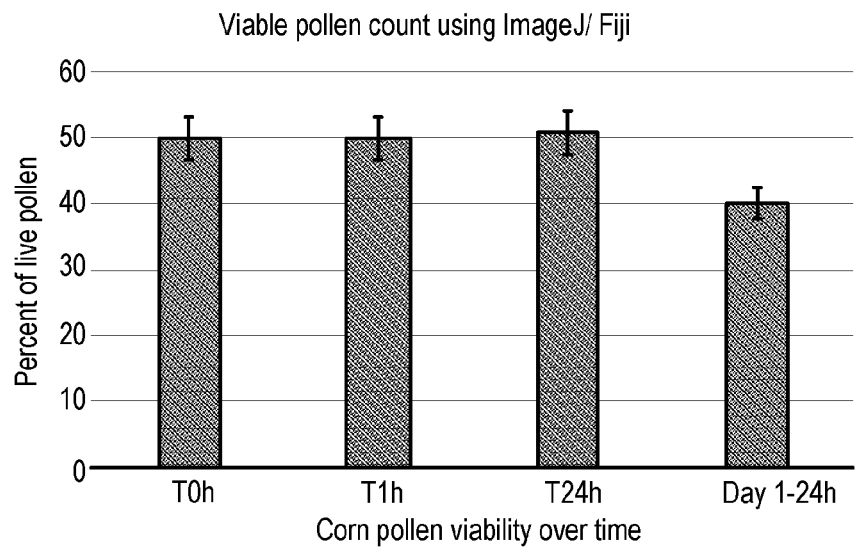
FIG. 19C illustrates a chart of viable pollen count using IMAGE)/FIJI.
Figure 19D:
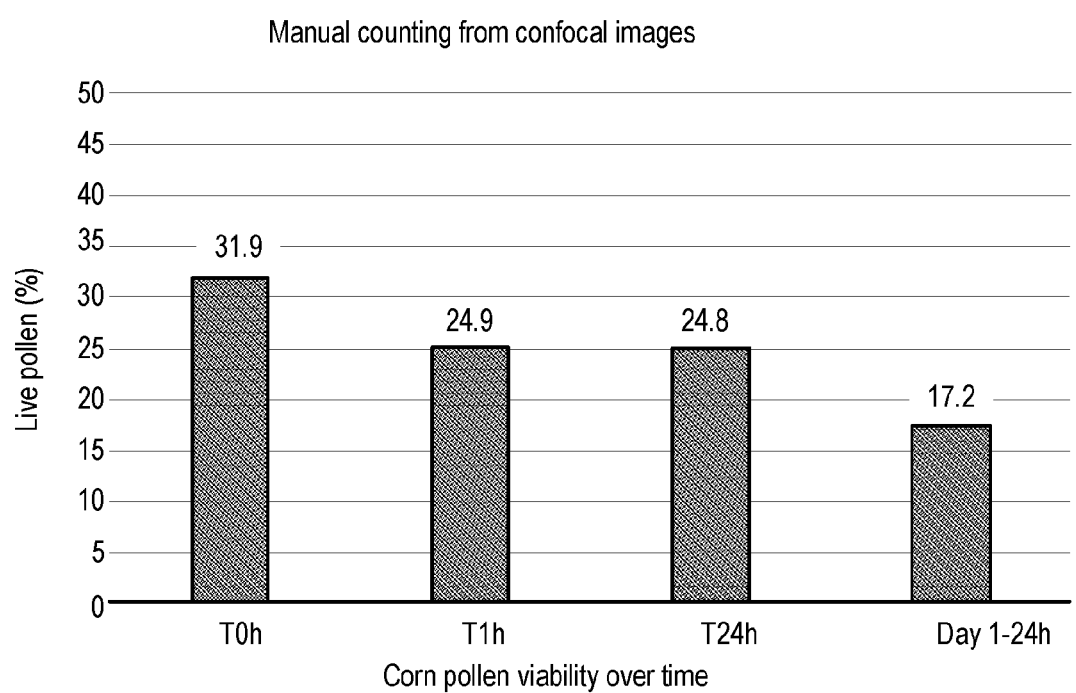
FIG. 19D illustrates a chart of viable pollen count using manual counting from confocal images.

FIG. 18 illustrates that aspects of the present disclosure are able to acquire acceptable data despite the presence of a bright light. The bright light in this instance was a ceiling light, but one of ordinary skill in the art will understand that sunlight may be the bright light in field conditions.

Exemplary Applications

An application common to both pollen detection and pollen-independent (e.g., petal differentiating, etc.) techniques described herein includes, but is not limited to, high-throughput roguing or plant selection or elimination for vegetable seed production in open or closed environments, such as greenhouses and the like. For example, detector 108 (and optionally filter 106) may comprise a goggle-like device worn by a human operator performing roguing and the techniques described herein for distinguishing male from female plants may enable the human operator to more efficiently perform the roguing. Optionally, the goggle-like device or an electronic camera connected to an electronic display may include an artificial electromagnetic radiation source 102. For example, users could take advantage of lower nighttime temperatures to rogue with the use of detector 108 (and optionally filter 106 and/or electromagnetic radiation source 102) comprising a goggle-like apparatus (e.g., similar to "night vision" goggles, electronic displays, a smartphone, an imaging device with or without an external light source, or a hand-held modular spectrometer, etc.). In another example, detector 108 (and optionally filter 106 and/or electromagnetic radiation source 102) confer "insect vision" via a display, lens, glasses, and/or other graphical human interface to the user for aiding in visualizing pollen and/or petal color differences, for example.

As another example, filter 106 and/or detector 108 may comprise automated, high-throughput systems configured to pass through, over, or adjacent to an area where crops are growing, including unmanned vehicles (e.g., rovers), mobile setups, and/or mobile robotic arms suspended in a greenhouse over a canopy of plants, for example. Exemplary automated systems within which filter 106 and/or detector 108 may be incorporated include a plant stand counter as described in U.S. Pat. No. 9,495,597, which is hereby incorporated by reference in its entirety, and an apparatus for in-field data collection and sampling as described in U.S. patent application Ser. No. 15/502,548, which is hereby incorporated by reference in its entirety. The automated, high-throughput devices (e.g., mobile platforms, vehicles, rovers, drones, etc.) move through a growing area and, utilizing the techniques described herein, detect and remove fertile or sterile plants from locations where they are not desired (i.e., roguing). As further described herein, this detection may be performed by determining which plants produce pollen (i.e., by detecting pollen on the anthers, petals, stigmas, tassels, or other flower parts), determining which plants have male-specific features or female-specific features (i.e., morphological features, reflected and/or emitted wavelengths or metabolites associated with male versus female flowers and/or leaves), and the like.

In another embodiment, the pollen detection techniques described herein are utilized to identify plants displaying cytoplasmic male sterility (CMS), genetic male sterility (GMS), and/or belonging to the roundup hybridization system (RHS) group. In yet another embodiment, the pollen detection techniques described herein are utilized to track pollen flow to ensure isolation of female flowers from pollen and/or prevent pollination, for example. In another embodiment, the pollen detection techniques described herein are utilized to verify pollen-free growing environments for plant species, such as dioecious species (e.g., *cannabis*, date palms, hops, etc.). Other applications in which the pollen detection techniques described herein may be utilized include, but are not limited to, forensics, sterile techniques, air quality, pollinator research, pollination efficiency, medical research of release of pollen as an allergen, entomology, and the like (e.g., any application in which one desires to know how much pollen is present at a given location).

In another embodiment, the pollen detection techniques described herein are utilized for indoor high-density cotton breeding applications, such as those described in U.S. Provisional Patent Application Ser. No. 62/435,209, filed Dec. 16, 2016, and PCT Patent Application Ser. No. PCTUS2017066623. The ability to cross cotton indoors is beneficial because it is insect-pollinated, which makes it very difficult to control pollination outdoors. Moving operations indoors eliminates the insects and improves the ability to control hybridization and the genetic purity of a pipeline. The methods and systems described herein are able to be utilized to monitor pollen those indoor facilities, helping breeders control and/or prevent the flow of pollen between plants.

One of ordinary skill in the art will understand that the pollen detection techniques described herein are able to be utilized across all plant industries including, but not limited to, horticulture, floriculture, herbs, spices, and the like. The systems and methods described herein are able to be utilized to find spectral signatures related to pollen in any crop.

The pollen detection techniques described herein enable at least: the ability to monitor and track the release, flow, distribution, and/or survival of pollen over time; the ability to quantify the proportion of viable pollen vs. non-viable pollen in a population; and the ability to quantify the proportion of sterile vs. fertile pollen in a population. Table 3 summarizes the classes of pollen status that the pollen detection techniques described herein are capable of distinguishing.

TABLE 3

|  | sterile | fertile |
| --- | --- | --- |
| viable | alive but never capable of fertilization | alive and capable of fertilization |
| non-viable | dead now and never capable of fertilization | dead now, but previously capable of fertilization |

In an exemplary embodiment, the methods and systems described herein can be utilized to characterize the release of pollen from a particular type of plant (e.g., to characterize the rate of pollen production from a particular inbred line). In another exemplary embodiment, a detector as described herein can be arranged to determine when pollen is first released from the flower of a plant (e.g., the tassel of a corn plant) at the start of the day and the systems and methods described herein can be used to quantify the pollen production by that plant over a period of time (e.g., several hours, etc.) to determine the total amount of pollen produced by the plant. Furthermore, by periodically or continuously determining the amount of pollen a plant produces, the systems, methods, and techniques described herein can estimate the times of day when that plant tends to produce most of its pollen. This pollen production characterization can be scored and associated with particular genotypes in much the same way that other traits are scored and used as a basis for selection by plant breeders to develop improved plants.

Additionally or alternatively, the data generated by the systems, methods, and techniques described herein can be used to develop models that improve the efficiency of activities related to pollination. These improvements include, but are not limited to, developing models that more accurately associate Growing Degree Units (GDU) with pollination-related activities and management (e.g., the best time to perform pollination activities such as manual and/or automated pollinations, exposure to insect pollinators, etc.).

Furthermore, because the systems, methods, and techniques described herein enable the efficient quantification of viable pollen vs. non-viable pollen, the systems, methods, and techniques can be used to characterize the survivability of pollen produced by a particular genotype. The survivability characterization can be used to manage pollination-related activities in a breeding program (e.g., performing pollinations at the ideal point in time when the greatest amount of variable pollen is present).

Moreover, the systems, methods, and techniques described herein can be used to determine the quantity of pollen that is sterile vs. fertile. Similarly to scoring and selecting plants based on the amount of pollen they produce, or the proportion of viable pollen they produce using techniques described herein, the systems, methods, and techniques described herein can be used to score and select plants based on the proportion of fertile vs. sterile pollen they produce.

Computing Environment

In addition to the embodiments described above, embodiments of the present disclosure may comprise a special purpose computer including a variety of computer hardware, as described in greater detail below.

Embodiments within the scope of the present disclosure also include computer-readable media for carrying or having computer-executable instructions or data structures stored thereon. Such computer-readable media can be any available media that can be accessed by a special purpose computer and comprises computer storage media and communication media. By way of example, and not limitation, computer storage media include both volatile and nonvolatile, removable and non-removable media implemented in any method or technology for storage of information such as computer readable instructions, data structures, program modules or other data. Computer storage media are non-transitory and include, but are not limited to, random access memory (RAM), read only memory (ROM), electrically erasable programmable ROM (EEPROM), compact disk ROM (CD-ROM), digital versatile disks (DVD), or other optical disk storage, solid state drives (SSDs), magnetic cassettes, magnetic tape, magnetic disk storage, or other magnetic storage devices, or any other medium that can be used to carry or store desired non-transitory information in the form of computer-executable instructions or data structures and that can be accessed by a computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which aspects of the disclosure may be implemented. Although not required, aspects of the disclosure will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Aspects of the disclosure may also be practiced in distributed computing environments where tasks are performed by local and remote processing devices that are linked (either by hardwired links, wireless links, or by a combination of hardwired or wireless links) through a communications network (e.g., Pipeline Pilot, GitHub, Amazon Web Services (AWS), Domino, etc.). In a distributed computing environment, program modules may be located in both local and remote memory storage devices.

An exemplary system for implementing aspects of the disclosure includes a special purpose computing device in the form of a conventional computer, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory computer storage media, including nonvolatile and volatile memory types. A basic input/output system (BIOS), containing the basic routines that help transfer information between elements within the computer, such as during start-up, may be stored in ROM. Further, the computer may include any device (e.g., computer, laptop, tablet, PDA, cell phone, mobile phone, a smart television, and the like) that is capable of receiving or transmitting an IP address wirelessly to or from the internet.

The computer may also include a magnetic hard disk drive for reading from and writing to a magnetic hard disk, a magnetic disk drive for reading from or writing to a removable magnetic disk, and an optical disk drive for reading from or writing to removable optical disk such as a CD-ROM or other optical media. The magnetic hard disk drive, magnetic disk drive, and optical disk drive are connected to the system bus by a hard disk drive interface, a magnetic disk drive-interface, and an optical drive interface, respectively. The drives and their associated computer-readable media provide nonvolatile storage of computer-executable instructions, data structures, program modules, and other data for the computer. Although the exemplary environment described herein employs a magnetic hard disk, a removable magnetic disk, and a removable optical disk, other types of computer readable media for storing data can be used, including magnetic cassettes, flash memory cards, digital video disks, Bernoulli cartridges, RAMs, ROMs, SSDs, and the like.

Communication media typically embody computer readable instructions, data structures, program modules or other data in a modulated data signal such as a carrier wave or other transport mechanism and includes any information delivery media.

Program code means comprising one or more program modules may be stored on the hard disk, magnetic disk, optical disk, ROM, and/or RAM, including an operating system, one or more application programs, other program modules, and program data. A user may enter commands and information into the computer through a keyboard, pointing device, or other input device, such as a microphone, joy stick, game pad, satellite dish, scanner, imaging device (e.g., camera), or the like. These and other input devices are often connected to the processing unit through a serial port interface coupled to the system bus. Alternatively, the input devices may be connected by other interfaces, such as a parallel port, a game port, or a universal serial bus (USB). A monitor or another display device is also connected to the system bus via an interface, such as video adapter. In addition to the monitor, personal computers typically include other peripheral output devices (not shown), such as speakers and printers.

One or more aspects of the disclosure may be embodied in computer-executable instructions (i.e., software), routines, or functions stored in system memory or nonvolatile memory as application programs, program modules, and/or program data. The software may alternatively be stored remotely, such as on a remote computer with remote application programs (e.g., Pipeline Pilot, GitHub, Amazon Web Services (AWS), Domino, etc.). Generally, program modules include routines, programs, objects, components, data structures, etc. that perform particular tasks or implement particular abstract data types when executed by a processor in a computer or other device. The computer executable instructions may be stored on one or more tangible, non-transitory computer readable media (e.g., hard disk, optical disk, removable storage media, solid state memory, RAM, etc.) and executed by one or more processors or other devices. As will be appreciated by one of skill in the art, the functionality of the program modules may be combined or distributed as desired in various embodiments. In addition, the functionality may be embodied in whole or in part in firmware or hardware equivalents such as integrated circuits, application specific integrated circuits, field programmable gate arrays (FPGA), and the like.

The computer may operate in a networked environment using logical connections to one or more remote computers. The remote computers may each be another personal computer, a tablet, a PDA, a server, a router, a network PC, a peer device, or other common network node, and typically include many or all of the elements described above relative to the computer. The logical connections include a local area network (LAN) and a wide area network (WAN) that are presented here by way of example and not limitation. Such networking environments are commonplace in office-wide or enterprise-wide computer networks, intranets and the Internet.

When used in a LAN networking environment, the computer is connected to the local network through a network interface or adapter. When used in a WAN networking environment, the computer may include a modem, a wireless link, or other means for establishing communications over the wide area network, such as the Internet. The modem, which may be internal or external, is connected to the system bus via the serial port interface. In a networked environment, program modules depicted relative to the computer, or portions thereof, may be stored in the remote memory storage device. It will be appreciated that the network connections shown are exemplary and other means of establishing communications over wide area network may be used.

Preferably, computer-executable instructions are stored in a memory, such as the hard disk drive, and executed by the computer. Advantageously, the computer processor has the capability to perform all operations (e.g., execute computer-executable instructions) in real-time.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

EXAMPLES

The following non-limiting examples are provided to further illustrate embodiments of the present invention.

Example 1: Pollen Collection, Storage, and Staining of Corn

Several fertile corn plants were grown in a growth chamber to flowering, at which point tassels were removed from the plants and transferred to a laboratory and maintained for several hours by placing the stalk in a bottle of water. Pollen was collected from the tassel and samples were either observed immediately or stored in aliquots at either room temperature (RT) or 4° C. The samples stored at RT were placed in plastic dishes and exposed to the open air of the laboratory, while the samples stored at 4° C. were sealed in re-sealable plastic pollen storage chambers with temperature and humidity sensors. At different time points, pollen was collected from the tassels and/or aliquots of pollen were drawn from one or both of the storage conditions, depending on the experiment, then subjected to analysis and observation. T0 aliquots were imaged immediately, while T1, T2, T4, T6, and T24 aliquots were observed after 1, 2, 4, 6, or 24 hours of storage, respectively. T14-days aliquots were observed after 14 days of storage. T24-t aliquots were never subjected to storage but rather collected directly from the maintained tassel at 24 hours. Each sample was imaged at its respective collection time point.

Staining was performed with BACLIGHT (Syto9, green, alive; and PI, red, dead) to determine pollen viability for each group. BACLIGHT (available from ThermoFisher Scientific) was prepared fresh from one pipette of each component mixed in 20 mL of double-deionized water. The stain was mixed with the pollen directly on confocal Petri dishes in the dark at room temperature for 20 minutes and then observed.

Imaging was performed using a ZEISS LSM700 confocal microscope using the following settings: 488 nm laser (green channel, alive), power 0.98%, 1 AU, and 555 nm laser (red channel, dead), power 0.98%, 1 AU, 2.5× objective.

Images were processed using ZEN (BLUE EDITION) software and/or analyzed with multivariate curve resolution (MCR) alogrithms using IMAGEMCR and RAPIDMCR software packages. IMAGE)/FIJI software was used to count and determine percent of viable pollen (live/dead pollen). Results were confirmed by visually counting green and red fluorescence cells from confocal images.

Pollen RGB images were also generated based on the pure spectral components detected.

Example 2: Detecting Viable Corn Pollen Vs. Non-Viable Corn Pollen

This Example demonstrates that hyperspectral confocal fluorescence (HSF) microscopy can reveal spectral profiles that can be used to detect and distinguish fertile corn plants and/or pollen vs. sterile plants and/or pollen.

Surprisingly, all analyses conducted demonstrated that the percent live pollen of the RT-stored aliquots is more than that of the pollen collected and imaged directly from the maintained tassel at 24 hours. In the ZEN analysis, the RT-stored pollen remained at about 50% live or slightly lower regardless of the time point, while the pollen collected from the tassel at 24 hours was considerably lower (T0=47.5%, T1=42.5%, T24=50.2%, T24-t=33.6%). Viable pollen counting using the IMAGE)/FIJI software produced a similar pattern (T0=T1=T24=50%, T24-t=40%) as did the manual counting from confocal images (T0=31.9%, T1=24.9%, T24=24.8%, T24-t=17.2%).

FIGS. 19A-D reveal how the HSF microscopy methods disclosed herein detected the same pattern of pollen viability over time, including the surprising loss of viability observed from the T24-t sample.

These results also demonstrate that that it is possible to use a threshold level of fluorescence produced by HSF microscopy to score whether pollen samples contain at least a certain amount of live pollen. Although the spectral profiles for samples containing approximately 50% viable pollen are very similar in the 500-800 nm range, there is a dramatic change in the spectral signature in that range of the sample containing the lowest amount of viable pollen (T24-t). The loss of a threshold-level spectral component in the wavelength band between about 515 nm and 630 nm for the T24-t sample is directly associated with its dramatically lower pollen viability confirmed through staining and counting.

These results confirm others that have been reported herein that live versus dead corn pollen can be distinguished at the cellular level by their spectral signatures.

Example 3: Differentiating Viable Corn Pollen Vs. Corn Anthers

This Example demonstrates that macro-hyperspectral imaging can reveal spectral profiles that can be used to detect and distinguish pollen vs. anthers.

Tassels of flowering corn lines Mo6 and Mob were harvested and their stalks placed in water to prevent dehydration. Tassels were mechanically shaken into a paper bag to separate anthers and pollen from the tassels and then the pollen and anthers were mechanically separated from one another and placed in separate wells of a hyperspectral imaging plate. Samples of the anthers were mechanically split open with a needle to expose their interior and verify through fluorescence and bright-field stereo microscopy that no residual pollen was present.

Macro-HSF imaging was performed using 488 nm laser excitation, and 500 to 1000 nm emission recording. Imaging was performed at the macro level with a 0.125× telecentric lens. Data was recorded as hyperspectral cubes and images opened with IMAGEJ software.

Figure 20:
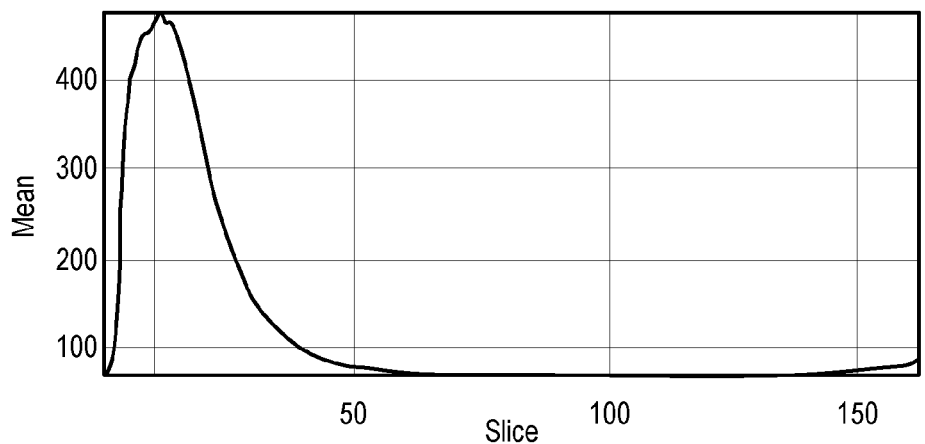
FIG. 20 illustrates spectral data of the auto-fluorescence spectra of isolated corn pollen and corn anthers with pollen.
Figure 20:
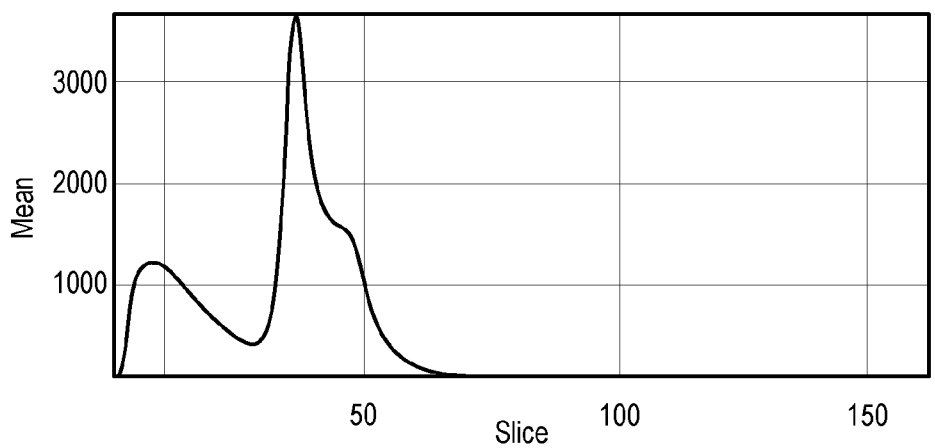

FIG. 20 reveals the raw data of the auto-fluorescence spectra of the isolated pollen and the spectra of anthers with pollen.

As expected, the software used in this experiment was unable to resolve the two spectral components that we observed when we used MCR (e.g. Example 1). However, these results clearly demonstrate that methods that do not rely on microscopy or sophisticated software can be used to detect the presence and/or absence of pollen and or distinguish fertile vs. sterile plants and plant parts. The dramatic differences in the shape of the spectral signature of isolated pollen between about 500 nm and 800 nm is clearly distinguishable from that of anthers without pollen.

Analysis of the pollen only sample reveals only a single band just to the red side of 564 nm with an intensity of about 500 counts. The anthers-only sample, however, reveal a strong band just to the blue side of 564 nm with an intensity of about 1200 counts and a strong chlorophyll emission at about 692 nm. This chlorophyll emission was lacking in the pollen-only sample.

As expected, Mob, which is more fertile, exhibited more intense fluorescence than Mo6, indicating that these methods can be used to distinguish plants with different fertility (e.g. pollen production) by their spectral components.

Example 4: Differentiating Viable Corn Pollen Vs. Non-Viable Corn Pollen

This Example demonstrates that hyperspectral confocal fluorescence (HSF) microscopy can reveal spectral profiles that can be used to detect the presence of viable pollen at very low frequencies.

Two series of pollen aliquots were collected and stored at either 4° C., or at RT, as described in Example 1, then removed from storage and observed at T1, T2, T4, and T24 following the staining and imaging steps described in Example 1.

Figure 21:
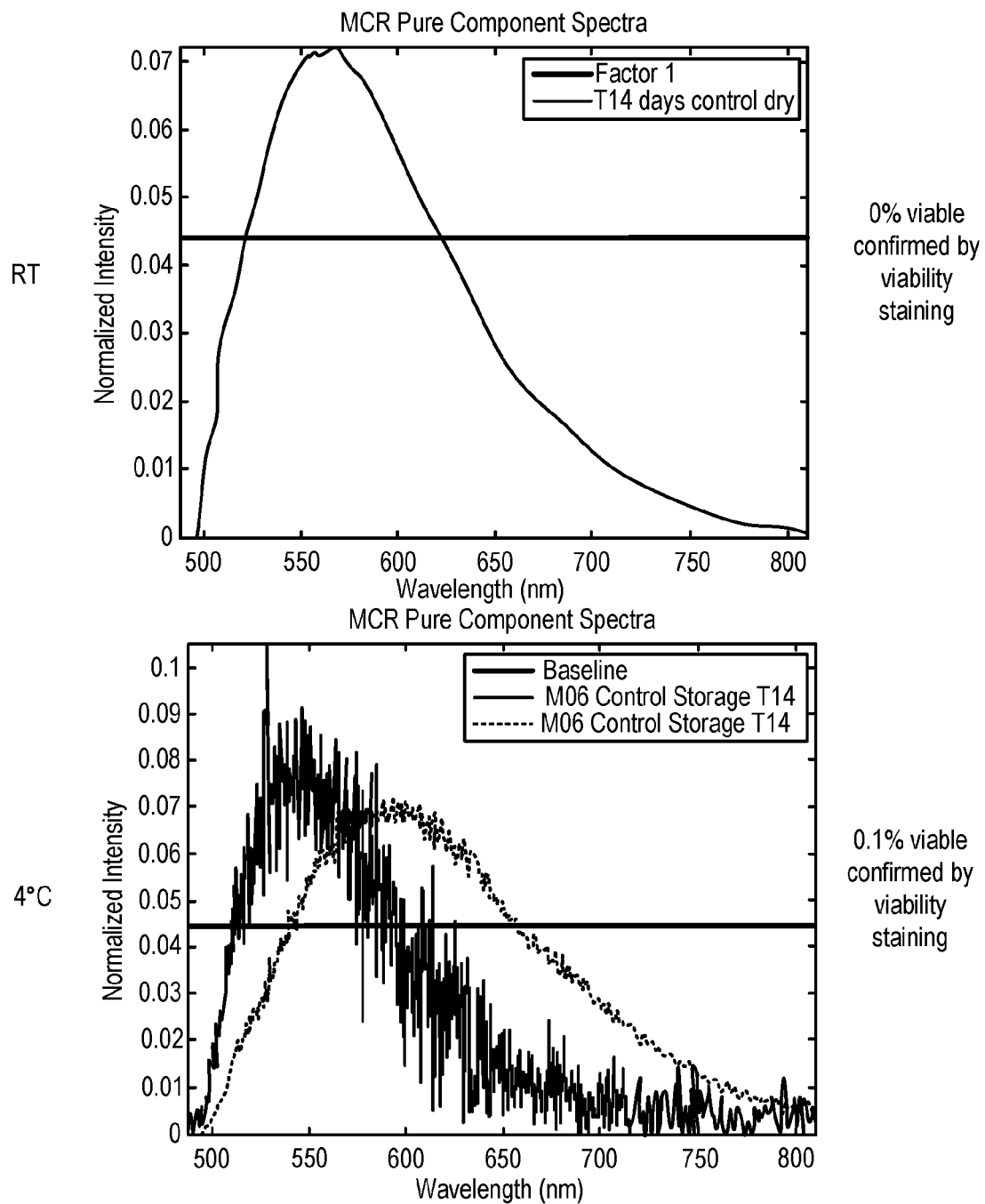
FIG. 21 illustrates spectral data at corn pollen stored at room temperature and 4° C.

Surprisingly, little difference was observed in the spectral profiles of the RT and 4° C. aliquots at any of the time points. Aliquots from both storage conditions exhibited the same general profile as that of the RT aliquot observed at T14-days in FIG. 21, i.e. a single spectral component that extended above the threshold from about 515 nm to about 630 nm, with a peak between about 545 nm and 575 nm, which was associated with a lack of viable pollen in other examples herein.

However, continued exploration of the samples eventually revealed one field of view in the aliquot stored at 4° C. for 14 days that exhibited two spectral components between about 500 nm and 700 nm; one that extended above the threshold from about 515 nm to about 630 nm and another extending above the threshold from about 540 nm to about 670 nm, which was associated with viable pollen in other examples herein.

To confirm the presence of viable pollen detected in the T14-days sample, staining and manual counting via confocal microscopy revealed viable pollen at a very low frequency (0.1%). The lack of any viable pollen in the other aliquots was similarly confirmed by microscopic observations of collapsed and/or senescent pollen grains throughout. Thus, the methods described herein are highly sensitive, capable of detecting the presence of viable pollen even at frequencies at least as low as 0.1%.

Example 5: Differentiating Fertile Corn Pollen vs. Sterile Corn Anthers

This Example demonstrates that HSF microscopy can reveal differences in the spectral signatures of fertile anthers and pollen versus that of sterile anthers.

Fixed, dehiscent anthers were harvested from the tassels of a fertile inbred line and a cytoplasmic male sterile (CMS) inbred line, then fixed in 3.7% formaldehyde. After approximately one year, the sterile anthers were hand-sectioned and imaged by HSF microscopy as described in Example 1. The results were compared to the results of HSF microscopy on fresh, fertile anthers with live pollen (FIG. 22).

Figure 22:
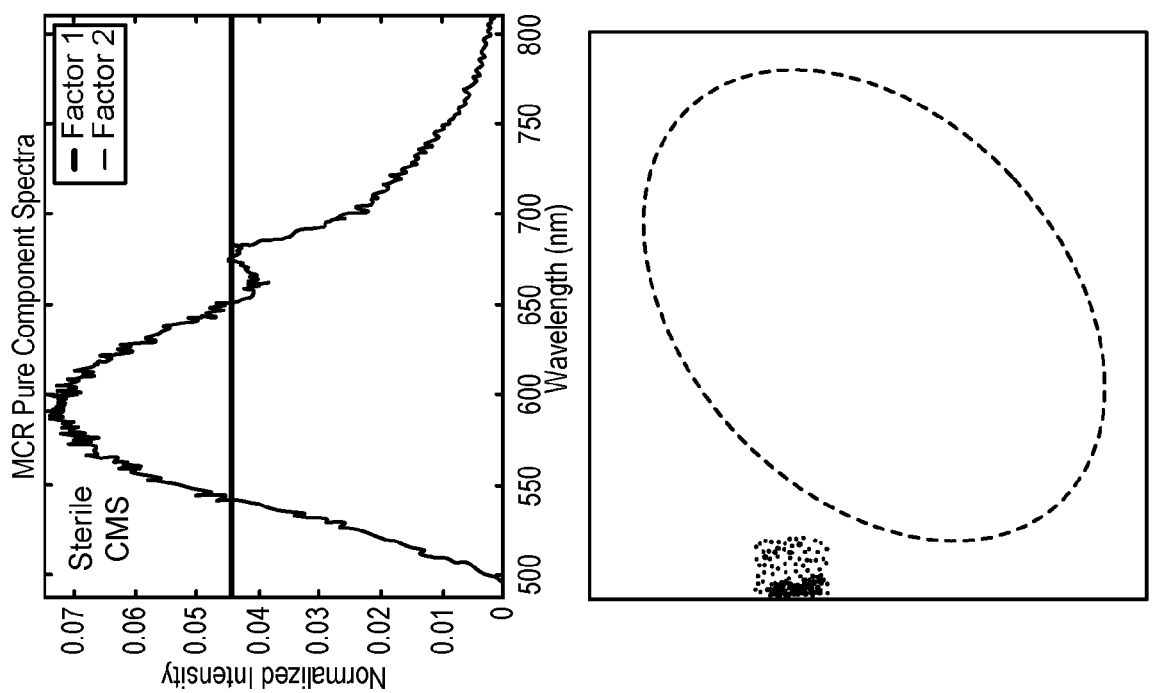
FIG. 22 illustrates spectral data and HSF microscopy on fertile anthers with live pollen compared with sterile anthers.
Figure 22:
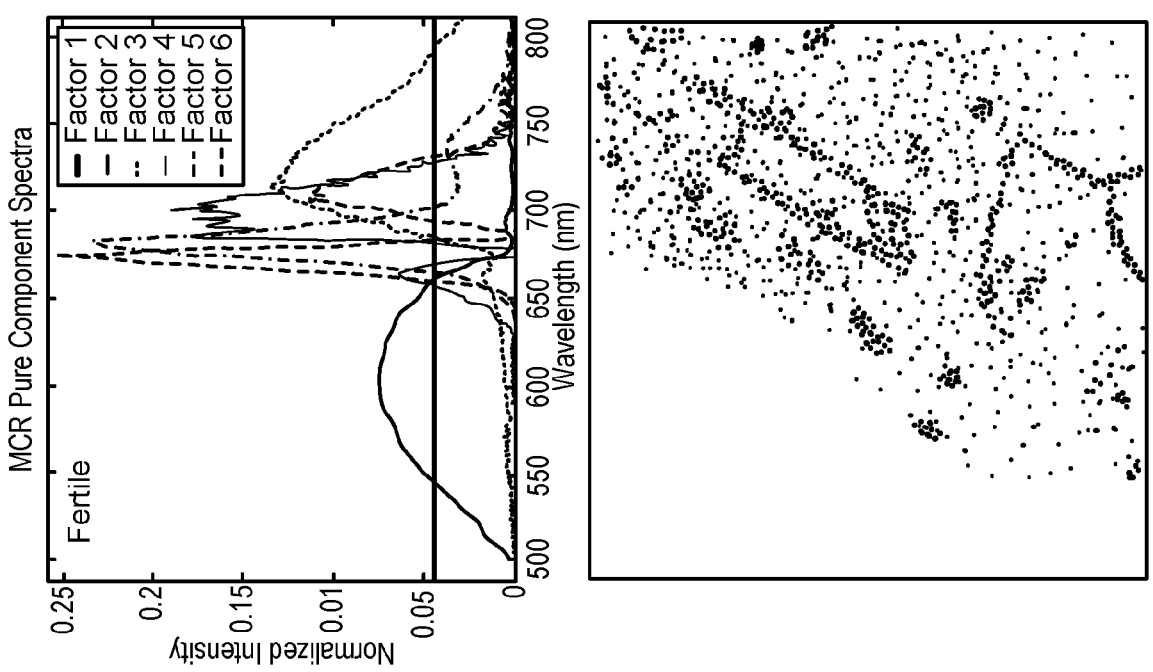

FIG. 22 demonstrates that the methods described herein can be used to reliably distinguish live pollen and fertile anthers from sterile anthers. They also revealed that a wide range of optical and/or imaging techniques and tools can be used to accomplish the objective. Even relatively simple microscopy, without the help of analytical software (e.g. fluorescence stereo microscopy using broad filters) can detect a green emission on immature anthers that is not exhibited by pollen. These results support the idea that the level of auto-fluorescence is dependent on cell wall composition and that the cell wall changes known to occur during anther development, maturation, and senescence could be an important factor in determining the best imaging conditions for a given set of circumstances. For example, due to thinning of anther cell walls as dehiscence approaches, one could reason that certain methods disclosed herein could be more reliable if used around the time of pollen shed, for example, from a few hours or days before dehiscence to a few hours or days afterwards, to reduce errors caused by changing fluorescent patterns in the tissues studied. The timeframes when most species shed pollen, however, will depend on the species, but are widely known in the art.

The table below summarizes the spectral data for corn.

| Specimen features | Wavelength range | Spectral Components |
|---|---|---|
| Anther fertile + pollen | 500 to 650 nm | 2 |
| Fertile pollen | 500 to 650 nm | 2 |
| Anther infertile/or plant | 500 to 780 nm | 3 or more |
| Anther sterile/or plant | 680 to 780 nm | 1 |
| Mature pollen "mutual" | 550 nm ± 30 nm | 1 |
| Live pollen "marker" | 600 nm ± 20 nm | 1 |
| Dead/sterile pollen | 565 nm ± 10 nm | 1 |
| Petal | 510-540 nm; >600 nm | 3 or more |
| Leaf | 500-540 nm; >650 nm | 3 or more |

Example 6: Differentiating Mature Sweet Pepper Flowers vs. Senescent Sweet Peppers Flowers and Flower Parts Using Epi-Fluorescence Imaging and HSF Optical Profiling An OLYMPUS SZX16 stereo microscope and an XCYTE XLED1 light source and four different emission filters (fluorescein isothiocyanate (FITC), tetramethylrhodamine (TRITC), chlorophyll (CHL), and 4',6-diamidino-2-phenylindole (DAPI)) were used to image flowers from four pepper plants that were heterozygous or homozygous for the presence of a single-nucleotide polymorphism (SNP) marker. Two of the plants (#4 and #6) were mature and two were senescing (#5 and #7).

The same flowers imaged and observed with epi-fluorescence microscopy were also subjected to hyperspectral fluorescence profiling using an OCEAN OPTICS handheld JAZ unit (and a probe provided by manufacturer).

Figure 23:
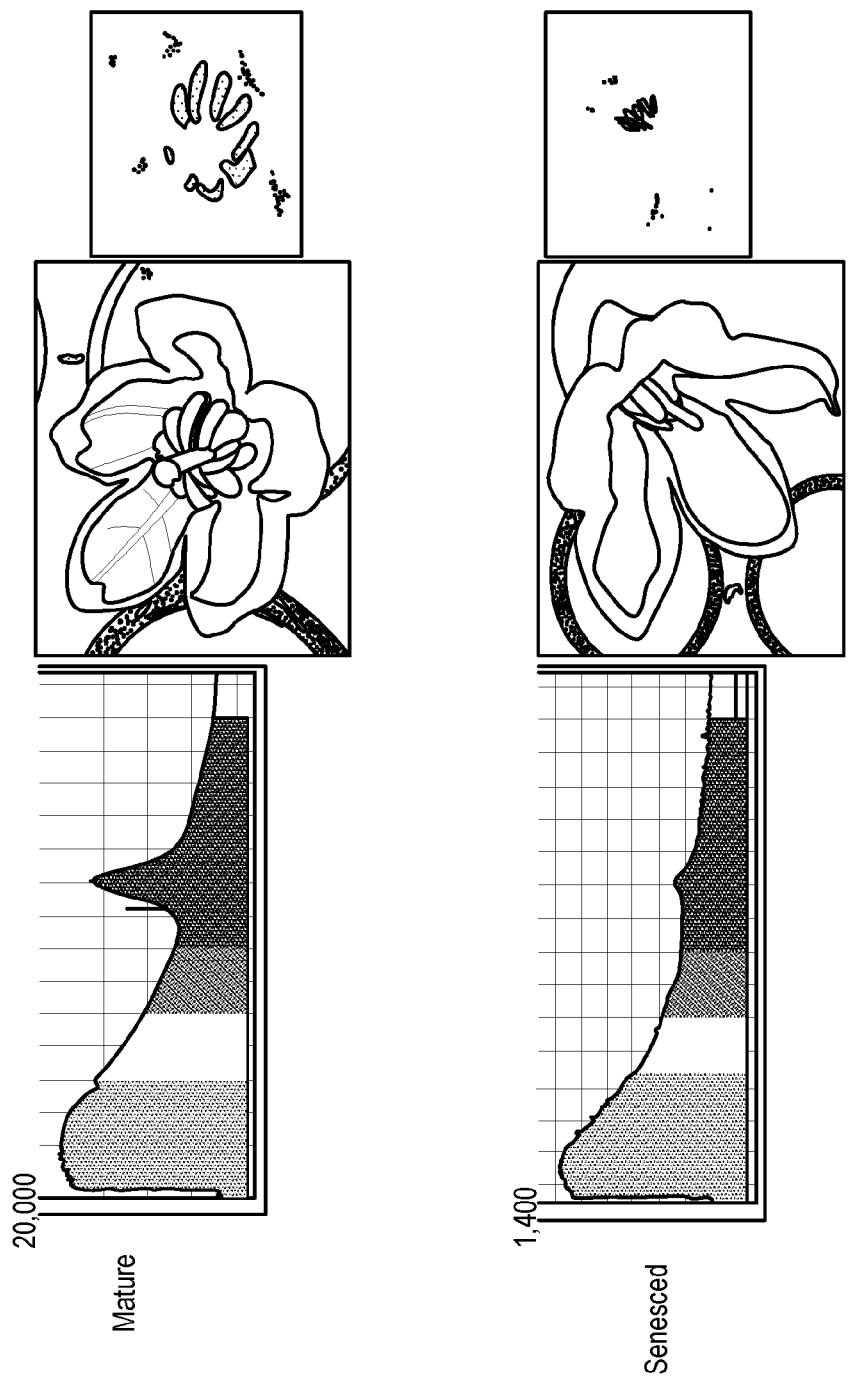
FIG. 23 illustrates spectral data and microscopic epi-fluorescence images of mature sweet pepper flowers and senescent sweet pepper flowers.

Microscopic epi-fluorescence images and spectral analyses revealed clear differences between mature flowers versus the senescent, detected both by epi-fluorescence imaging and HSF optical profiling (FIG. 23).

The FITC and TRITC filters worked best for highlighting the location of anthers. The CHL filter worked best for distinguishing the stigma and highlighted the location of petals as well. The DAPI filter was the best at highlighting the petals, but not very useful at revealing the location of other flower parts. Anthers of senescent flowers exhibited weak or no fluorescence in the green or red. Thus, one can clearly use the methods disclosed herein with a wide range of filters and, obviously, different filters will be better at imaging certain flower parts. Furthermore, these results reveal that the methods disclosed herein can be used to differentiate flowers based on their maturation, e.g. from young (pollen about to be released) through the end of pollen shed. Depending on the species, this window could last hours, days, perhaps even weeks.

As expected, the pollen-associated spectral signals of the mature flowers were greater than that of the senesced flowers, demonstrating how these methods could be used to track the shed/death of pollen and the loss of flower fertility over time. Mature pepper anthers emit fluorescence peaks between 500 and 650 nm with the shape of the peaks depending on the light source used for excitation.

The results also revealed that the methods disclosed herein can be used without software or complicated microscopy to detect the presence of fertile pollen and/or distinguish fertile plants from sterile plants. The auto-fluorescence differences within the visual range of the electromagnetic spectrum that we detected opens the use of the new methods disclosed herein to be combined with a broad range of sensing technologies and image/optical processing methods. One of ordinary skill in the art should easily anticipate combining the teachings herein with methods of comparing the ratios of intensities observed at different wavelengths from pollen and/or flower parts to detect viability, fertility, and track flower maturity and/or development, among other applications.

Example 7: Distinguishing Fertile Sweet Pepper Flowers vs. Sterile Sweet Pepper Flowers Using Epi-Fluorescence Imaging and HSF Microscopy Generation of Plant Parts:

A population of six different types of sweet pepper seeds were cultivated hydroponically using an AEROGARDEN and the manufacturer's instructions. The six plants were heterozygous for genetic male sterility (GMS), and should have segregated in a 1:1 ratio. 63, 69, 76, and 83 days after planting (DAP), flowers were collected, and their petals, anthers, and pollen observed following the protocols described herein.

Whenever possible, pollen viability and/or the fertility/sterility of anther samples analyzed in experiments described herein were confirmed by staining and confocal microscopy. Additionally, samples were subjected to scanning electron microscopy to further confirm the fertility status that was assigned to the tissues studied and, perhaps, account for the differences in spectral profiles disclosed herein. Wax crystals were found on both types of anthers, although more of it appeared on the sterile samples. The presence of mature pollen in dehiscent and fertile anthers was confirmed, as well as, a lack of pollen in dehiscent and sterile anthers (which also appeared to produce more wax crystals in/around the openings in the anthers). These data quality control checks also revealed that not all anthers of the "fertile" sweet pepper plants studied here produced the same amount of pollen. As expected, anthers could be found on plants traditionally considered "fertile" that appeared to produce very little pollen. SEM and confocal microscopy also revealed that some "sterile" anthers could have variable amounts of infertile pollen. Thus, users of this innovation are reminded that the more samples analyzed (e.g. multiple anthers, flowers, plants, etc.) the more confidence a user can have in the results. Those of ordinary skills in the art will understand that a single anther is often not an appropriate sample size to represent the entire population of all anthers in a flower, much less an entire plant.

Epi-Fluorescence Imaging Results:

The proportion of live pollen is proportional to the fluorescence intensity. Fluorescence intensity can be used to distinguish fertile vs. sterile anthers/flowers and can be used to predict fertilization success and/or fruit production.

Pepper fruit began to develop in December and the number of fruit each plant produced was recorded. Five of the six plants turned out to be fertile, as evidenced by fruit production. Fertile anthers with live pollen showed strong fluorescence with a GFP/FITC filter when excited with UV light at first, and as the pollen was shed and/or died, fluorescence intensity diminished. When the pollen was no longer present, fluorescence was also no longer observed.

Anthers of the sterile plant were immediately distinguishable from the fertile anthers as they produced little or no green fluorescence with the GFP/FITC filer under the same treatment. Fertile anthers with viable fertile pollen showed strong fluorescence using GFP/FITC filters (green), which was weak for sterile anthers with viable infertile pollen (pollen not capable of fertilization) and absent for sterile anthers with no pollen.

Figure 24:
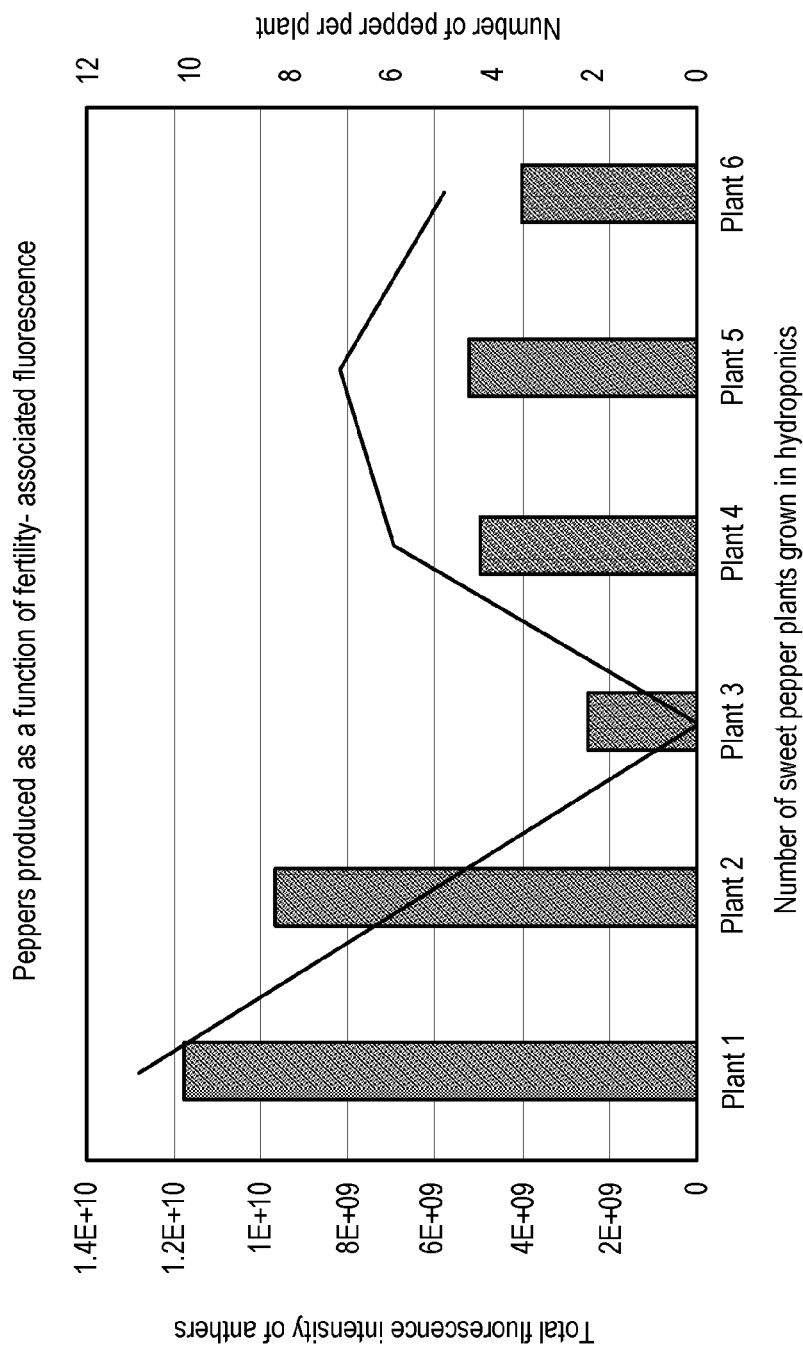
FIG. 24 illustrates a chart of peppers produced as a function of fertility-associated fluorescence.

FIG. 24 reveals how these methods can be used to predict fertility and fruit set. The number of pepper fruits each plant produced (the narrow line measured by the right vertical axis) can be compared to the observed fluorescence intensity for each plant (wide vertical bars measured by the left vertical axis). The rank order of plants based on their fluorescence intensity is identical to the rank order of the plants based on their fruit set (5 was highest, then 2, 6, 4, 6, 3). One of ordinary skill in the art will immediately realize a broad range of embodiments that can make use of this correlation. In certain embodiments, a computer algorithm could be created that makes use of how plant fertility is related to flower fluorescence intensity to automatically detect and distinguish whether an image, spectral profile, and/or other optical information originated from either a fertile plant or a sterile plant. For example, a threshold of fluorescence intensity (e.g. $3 \times 10^9$ for the data in FIG. 24) could be used by the algorithm to identify plants whose flowers exhibit less than the threshold and assign them as sterile; plants above the threshold would be fertile.

The 1:1 correspondence between the rank order of fruit set and fluorescence intensity reveals that these methods are not limited to qualitative differentiation. Automated, high-throughput systems capable of collecting reliable quantitative data related to fertility, fruit set, and/or pollen production using the methods described herein are envisioned. Although the thresholds for different crops, cropping systems, and research conditions will likely be different, the methods described herein can be adapted using routine methods known in the art to determine a threshold that suits a user's specific needs.

Figure 25:
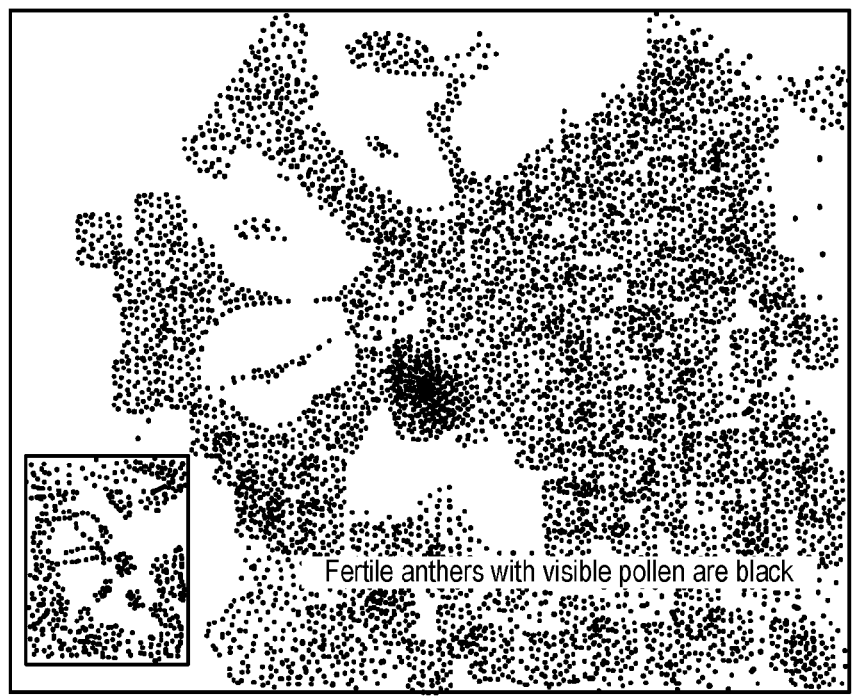
FIG. 25 illustrates images of sterile sweet pepper flowers and fertile sweet pepper flowers observed under UV excitation and a Rhodamine/TRITC (red) filter.
Figure 25:
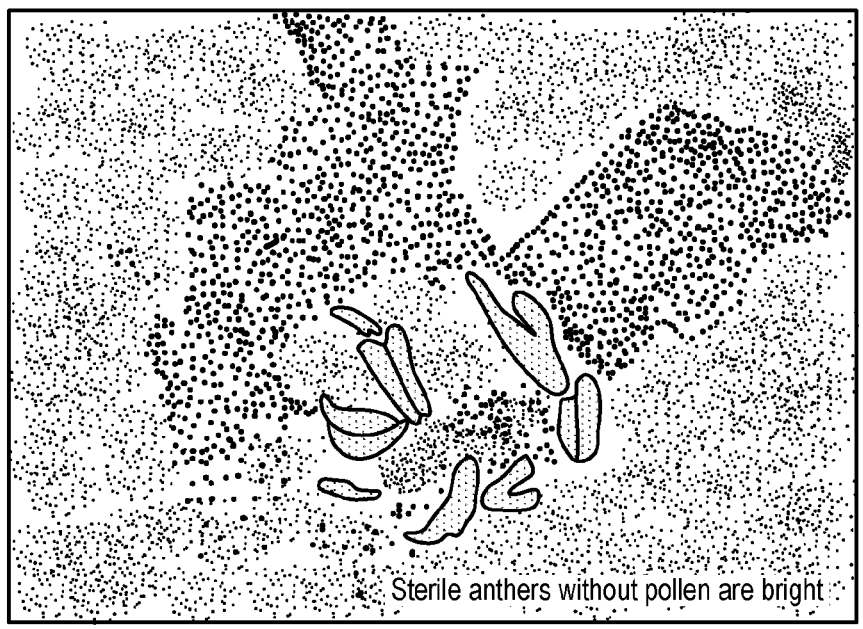

FIG. 25 shows representative images of sterile flowers and fertile flowers observed under UV excitation and a Rhodamine/TRITC (red) filter. Flowers of the sterile plant (#3) or were immediately distinguishable from all the fertile plants when observed under UV excitation and a Rhodamine/TRITC filter; fertile anthers with fertile pollen did not fluoresce, whereas sterile anthers showed fluorescence. Furthermore, the fluorescence observed under Rhodamine increased with presence of infertile pollen. The results of similar experiments conducted on cotton and described elsewhere herein follow a predictable pattern of sterile anther fluorescence vs. fertile anther fluorescence, although the fertile anthers in cotton fluoresced brightly with Rhodamine/TRITC filter, whereas the sterile cotton anthers did not. This reveals that even without MCR analytics software, the methods disclosed herein can be used to accomplish similar results, including a broad range of quantitative and or qualitative data characterizing the status of pollen present, fertility/sterility of plants/plant parts, fruit set, etc. It is anticipated that different filters might work better in different lighting conditions or work better in different species for different flower parts, etc. but that it would not require undue experimentation to determine general parameters suitable for the user's needs.

HSF microscopy can be used to detect spectral profiles specific to fertile pollen and distinguish flowers producing fertile pollen from flowers that are no longer producing fertile pollen.

Figure 26:
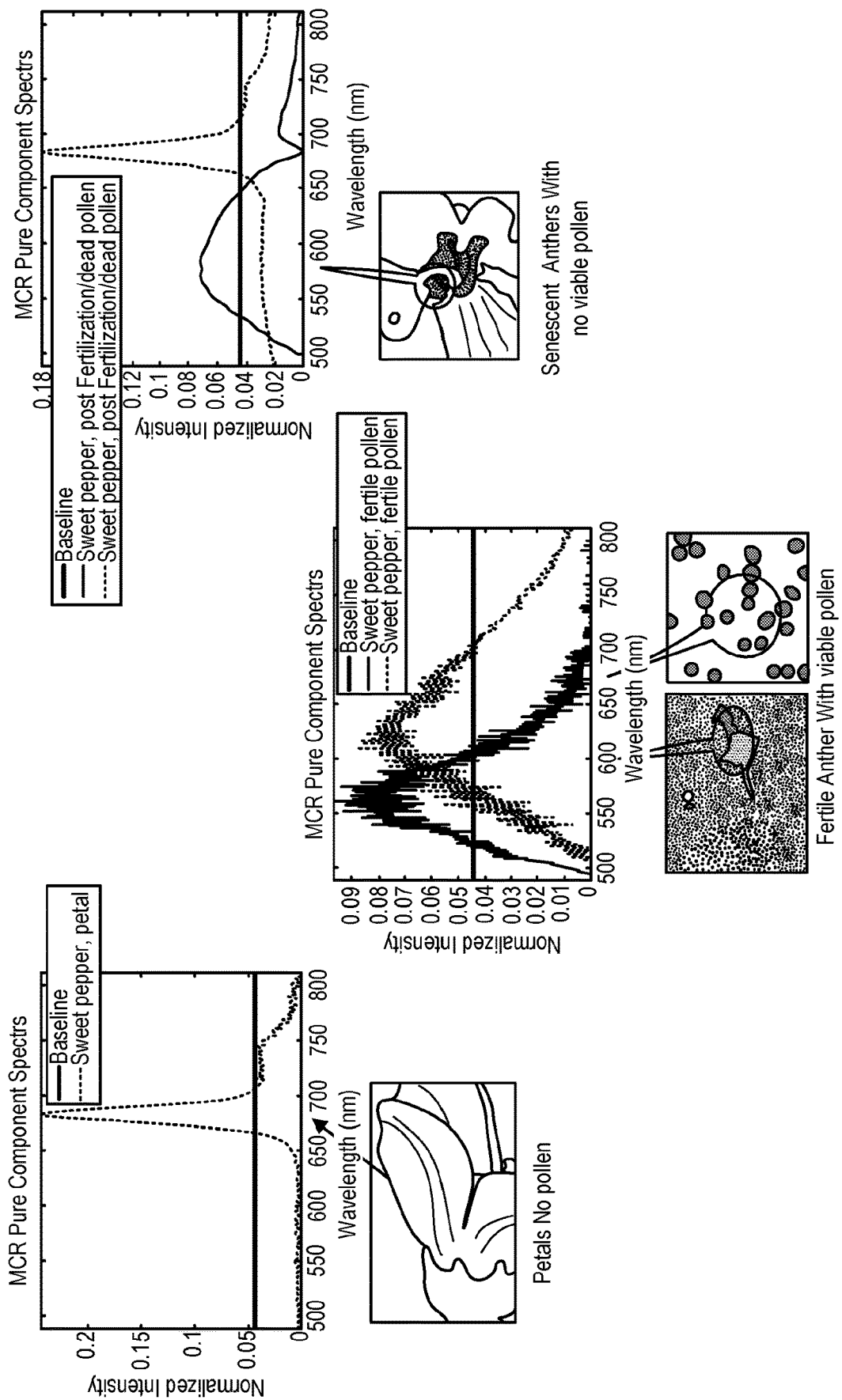
FIG. 26 illustrates spectral data and microscopy images for sweet pepper petals with no pollen, fertile sweet pepper anthers with viable pollen, and senescent sweet pepper anthers with no viable pollen.
Figure 27A:
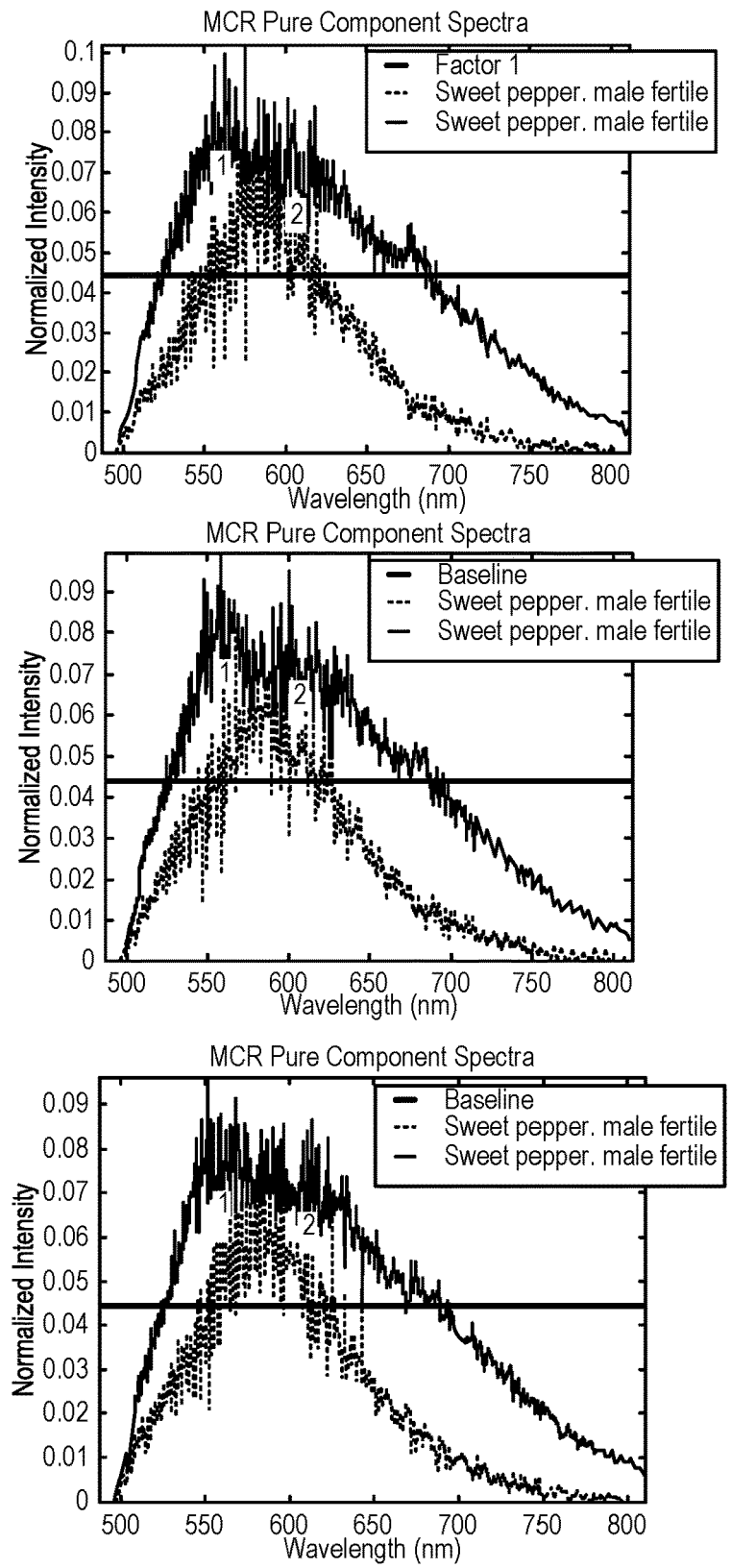
FIG. 27 illustrates spectral images generated from HSF microscopy and MCR analysis of fertile (FIG. 27A) and sterile sweet pepper anthers (FIG. 27B).
Figure 27B:
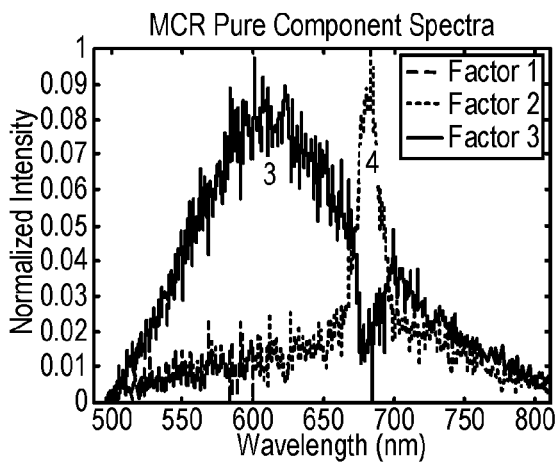
Figure 27B:
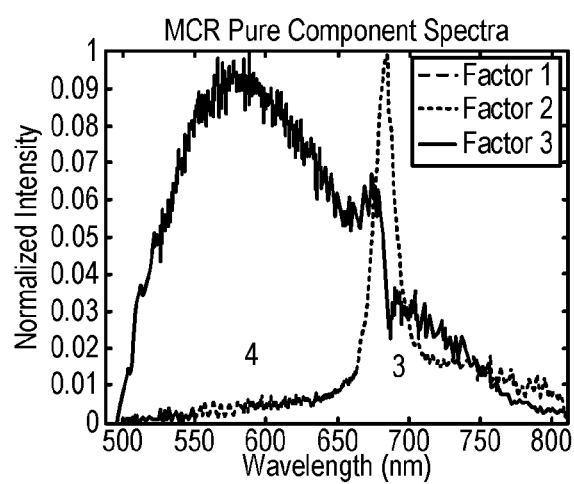
Figure 27B:
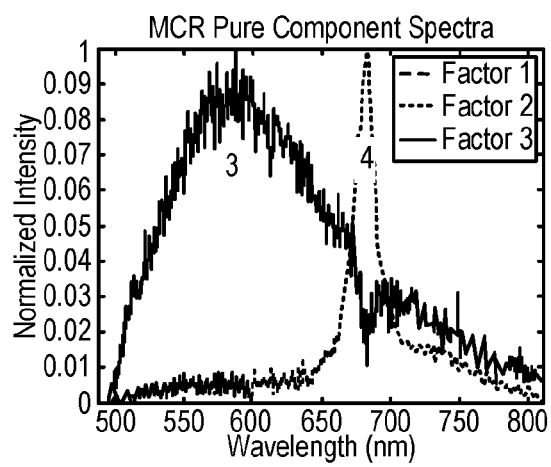
Figure 27B:
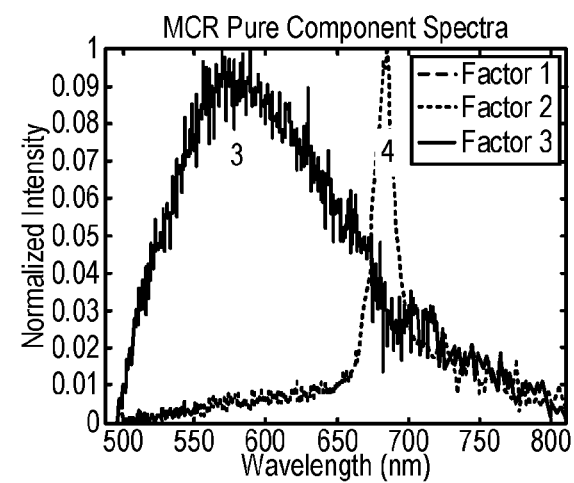

Flowers from the same hydroponic pepper plants that were analyzed in the epi-fluorescent imaging analyses above were also observed using the HSF microscopy protocols described in Example 1. FIG. 26 shows representative images of each of the three types of spectral profiles exhibited by the specimens, demonstrating how the methods disclosed herein can be used to detect the presence of pollen and track the maturation and senescence of pollen production. Intermediate states are also assumed, as the increase/decrease of fluorescence signals disclosed herein correspond to the non-binary nature of pollen production in fertile anthers as they age, decreasing as pollen is shed and/or dies.

The HSF profile of fertile anthers and pollen comprise two spectral peaks between about 500 nm and 700 nm, (although the precise location of the highest emission peaks depend on the light source used for excitation) but lacked the chlorophyll-associated peak between about 680 and 700 nm exhibited by both petals and senescent anthers (empty or containing only dead pollen). The senescent anthers also produced a weak signal between 500 and 650 nm.

These results confirmed that flowers with fertile anthers producing viable pollen can be differentiated from flowers lacking viable pollen, and that the presence of certain spectral signals associated with flower development stages can be used to track flower maturation.

Example 8: Distinguishing Fertile vs. Sterile Sweet Pepper Using Digital Imaging and HSF, Confocal, and Electron Microscopy Generation and Preparation of Plant Parts:

A population of fifteen different types of sweet pepper seeds were cultivated in a growth chamber and the number of fruit each plant produced was recorded. Although the plants were allegedly heterozygous for genetic male sterility (GMS), and should have segregated in a 1:1 ratio, five of the fifteen were identified as sterile by visual examination, microscopy, and 0% fruit set.

Seeds were planted in early November and flowers from all plants were harvested at Dec. 20, 2018, Dec. 27, 2018, Jan. 3, 2019, Jan. 8, 2019, Jan. 10, 2019, Jan. 17, 2019, Jan. 21, 2019, Jan. 22, 2019, Feb. 1, 2019, Feb. 11, 2019, Feb. 13, 2019 and separated in "fertile" and "sterile" samples, depending on the fertility observed of the mother plant from which the sample was taken. At each harvest, the petals, anthers, and pollen of each flower were observed following the protocols described herein.

Imaging was performed on fresh, fixed (3.7% formaldehyde) and frozen (−80° C.) flowers, anthers and pollen, as well as fresh dead pollen and leaves/leaf discs from fertile and sterile sweet pepper plants. To extend flower production, plants were trimmed regularly starting at approximately 2 months after planting (Jan. 7, 2019).

HSF Microscopy Results:

FIG. 27 shows representative spectral signatures generated from the HSF microscopy and MCR analysis. In the 500 nm to 700 nm range, fertile anthers producing viable pollen consistently exhibited spectral profiles that were clearly distinguishable from the profiles exhibited by the sterile anthers with infertile pollen. For example, fertile anthers (represented in FIG. 27A) exhibited a first spectral component that extended above the threshold from about 520 nm to about 620 nm, with a peak between about 550 nm to about 560 nm and a second spectral component from about 550 nm to about 690 nm with a peak between about 555 nm and about 605 nm. On the other hand, the anthers of sterile flowers (represented in FIG. 27B) exhibited a first spectral component that extended above the threshold from about 520 nm to about 680 nm, with a peak between about 570 nm and about 590 nm and a second spectral component from about 670 nm to about 700 nm, with a peak at about 685 nm, which was associated with chlorophyll fluorescence. These features were consistent among flowers from different plants collected on different days, regardless of whether the specimens were fresh, fixed, or frozen. It is anticipated that automated methods (including the use of certain algorithms) to rapidly detect these spectral features can be used to differentiate plants and/or plant parts based on their fertility and/or association with viable pollen production.

Figure 28B:
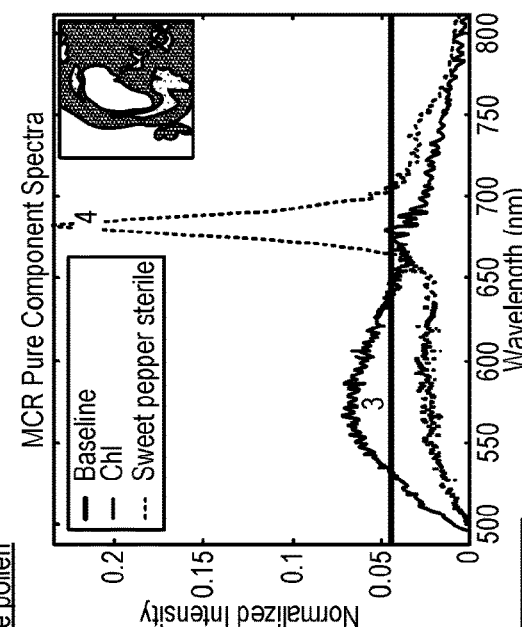
FIGS. 28A-C illustrate representative spectral signatures and microscopic images of sterile sweet pepper anthers.
Figure 28A:
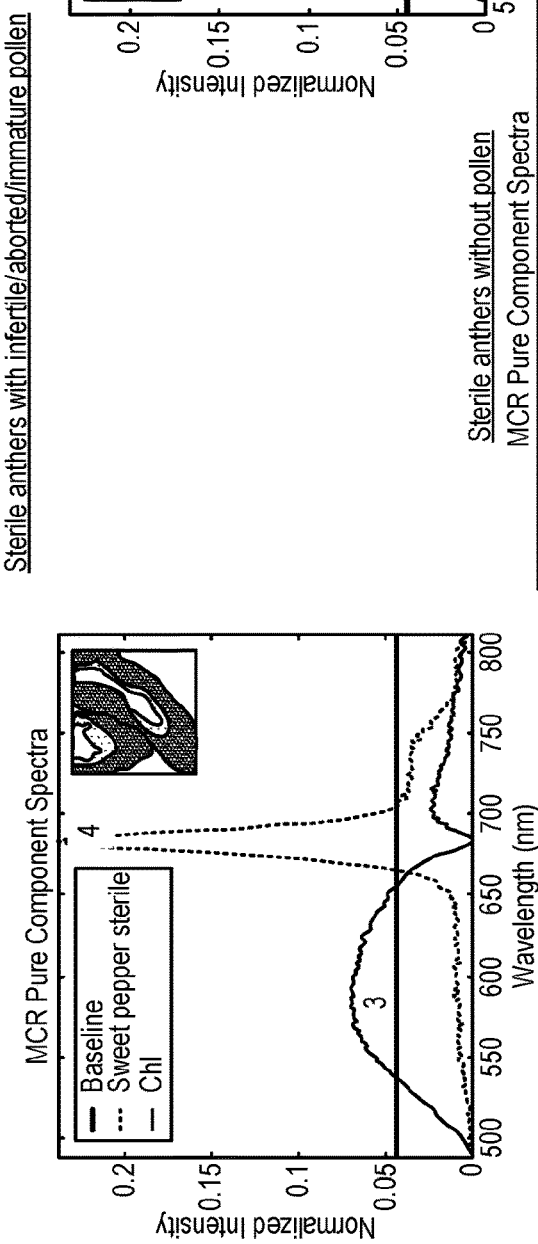
Figure 28C:
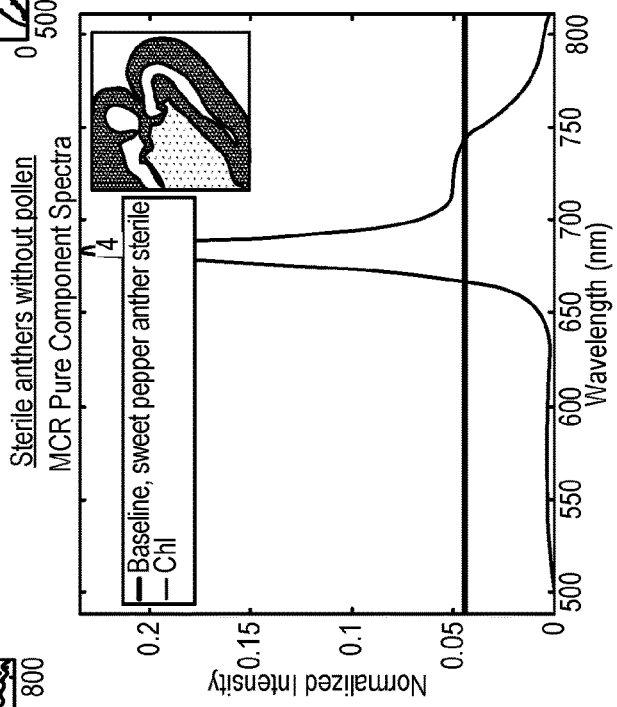

FIGS. 28A-C show representative spectral signatures and microscopic images of the sterile anthers. The microscopy clearly indicated that while some anthers contained immature/aborted pollen, they nevertheless exhibited the two spectral components detected in the sterile anthers with infertile pollen in FIG. 27B. On the other hand, some of the sterile anthers contained no pollen whatsoever. These sterile anthers exhibited no emissions other than the single sharp peak at approximately 685 nm associated with chlorophyll, a spectral signature shared by normally sterile plant parts (e.g. petals, FIG. 26). This surprising result reveals that the methods disclosed herein can be used not only differentiate plants that are fertile and have pollen producing anthers from plants that are sterile, but that it is also possible to determine whether sterility is a result of anthers producing infertile pollen, or because anthers are not producing pollen altogether.

Furthermore, the intensity of the non-chlorophyll-associated spectral component in sterile anthers with infertile pollen (FIG. 28C) exhibited at approximately 575 nm (±25 nm) is directly proportional to the frequency of infertile pollen present in/on the anther. As the amount of infertile pollen present in the anthers decreases, a commensurate decrease in the intensity of that spectral component was also observed, all the way down to zero infertile pollen observed at zero emissions at those wavelengths. This same spectral component corresponds to the auto-fluorescence detected in green channels or by GFP/FTIC filters in other experiments described herein.

The second component in sterile anthers with infertile pollen (labeled 4 in FIG. 27B) corresponds to chlorophyll auto-fluorescence detected in the red channel and/or by TRITC or chlorophyll filters in other experiments described herein.

Figure 29:
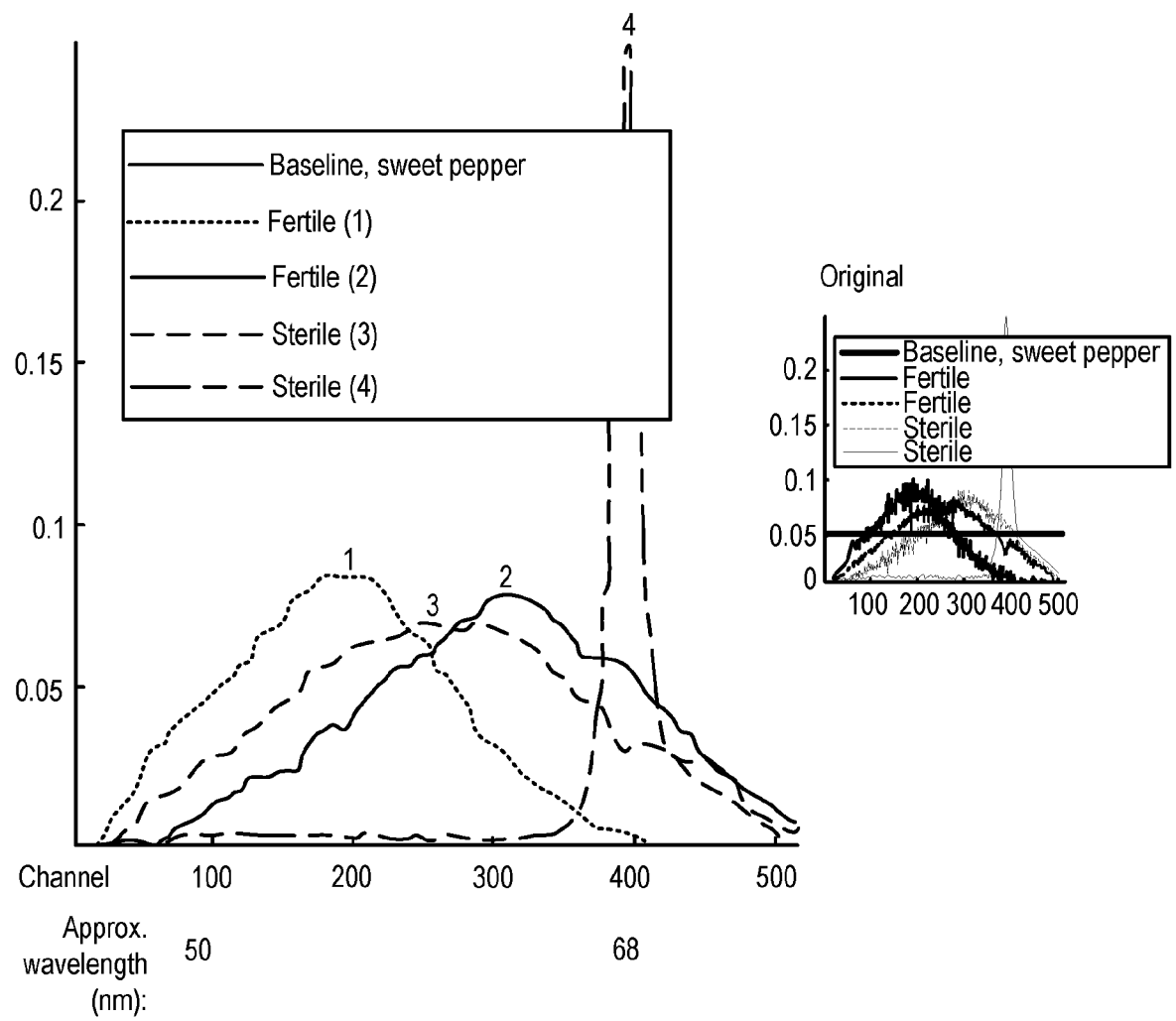
FIG. 29 illustrates a chart including spectral data for both sterile and fertile sweet pepper anthers.
Figures 30A, 30B:
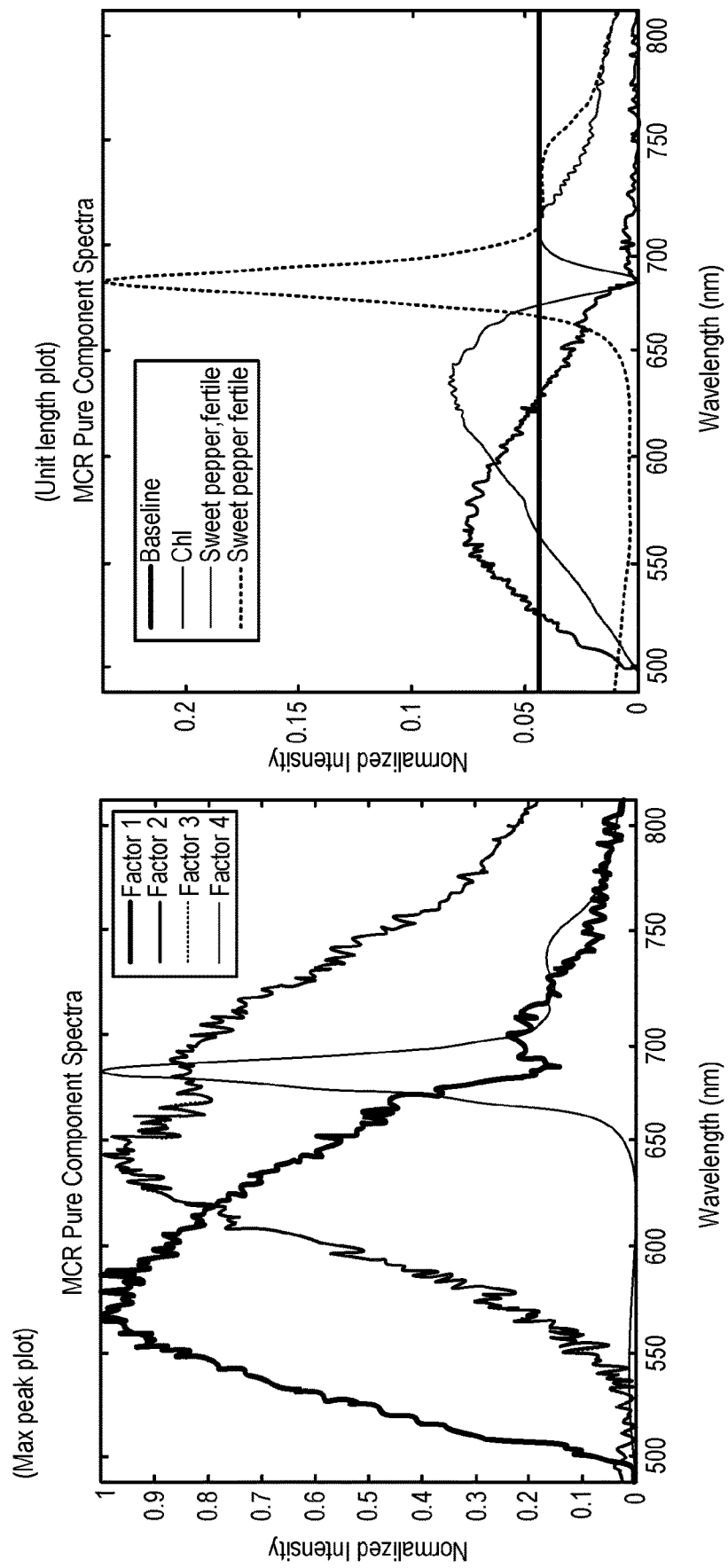
FIGS. 30A-F illustrates representative examples of the differences observed in sweet pepper in the sweet pepper experiments.
Figure 30D:
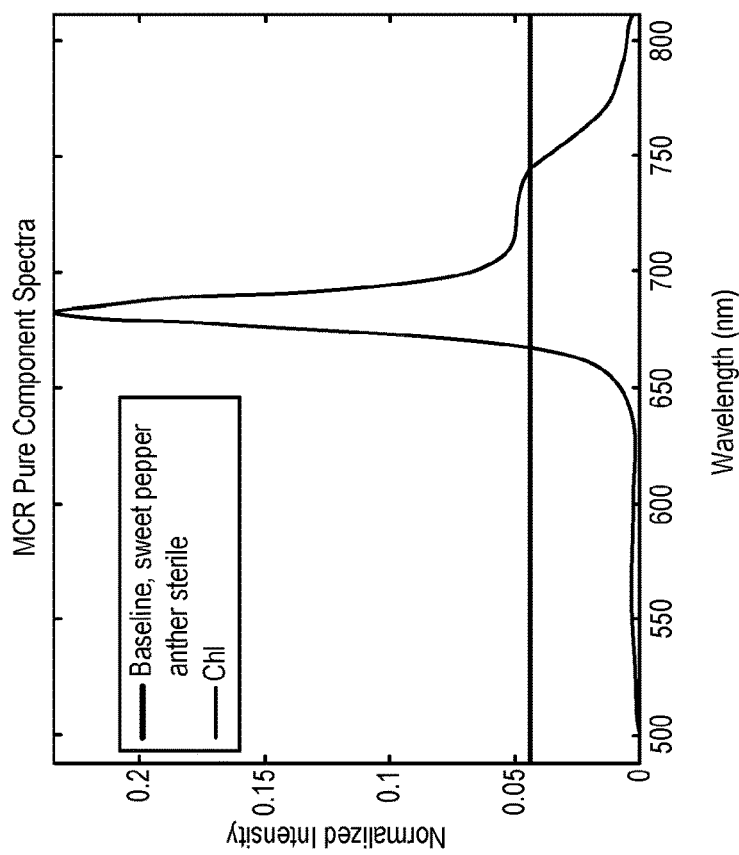
Figure 30C:
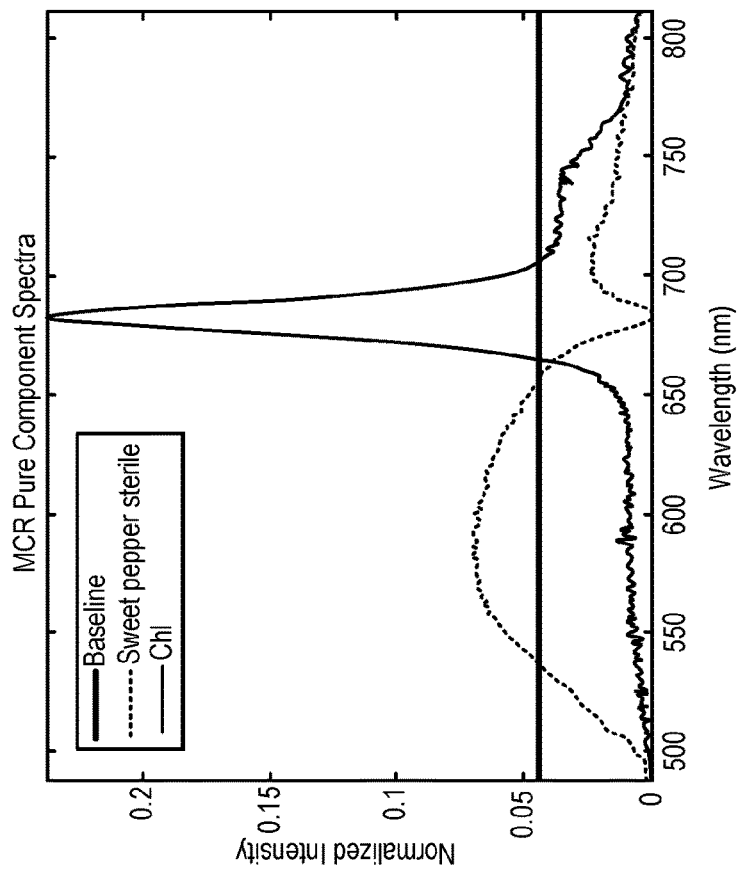
Figure 30F:
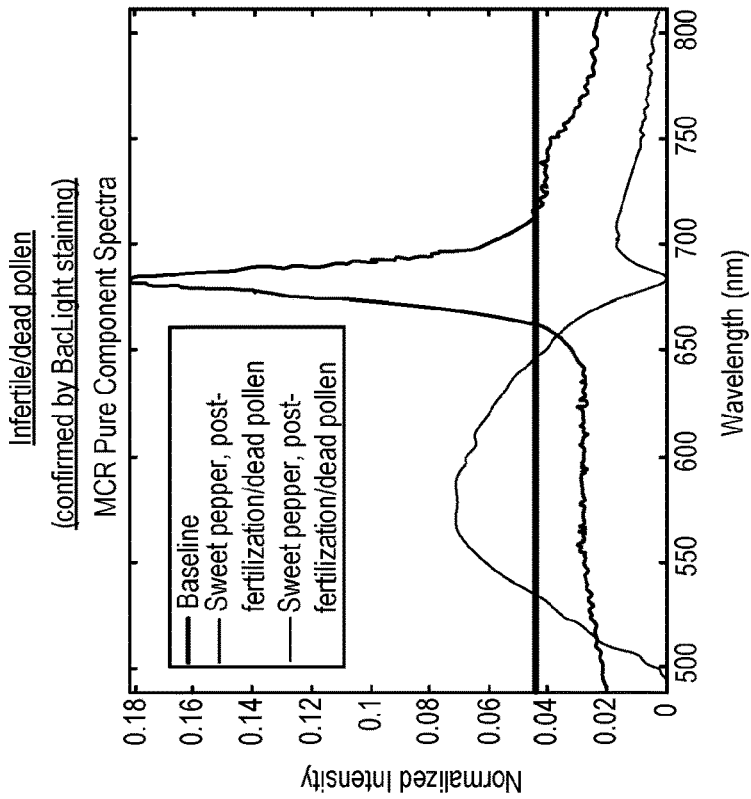
Figure 30E:
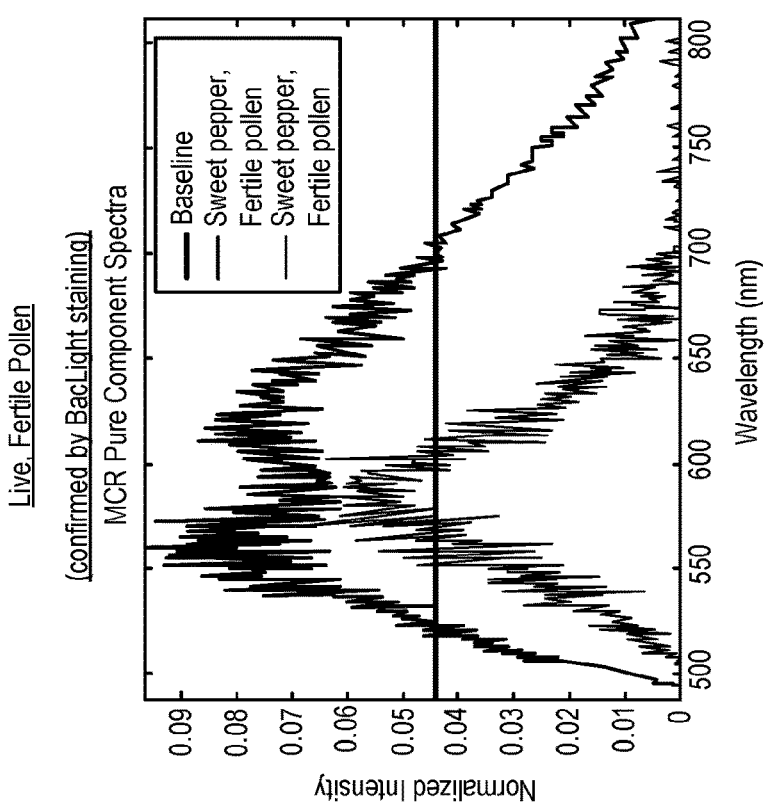
Figure 31:
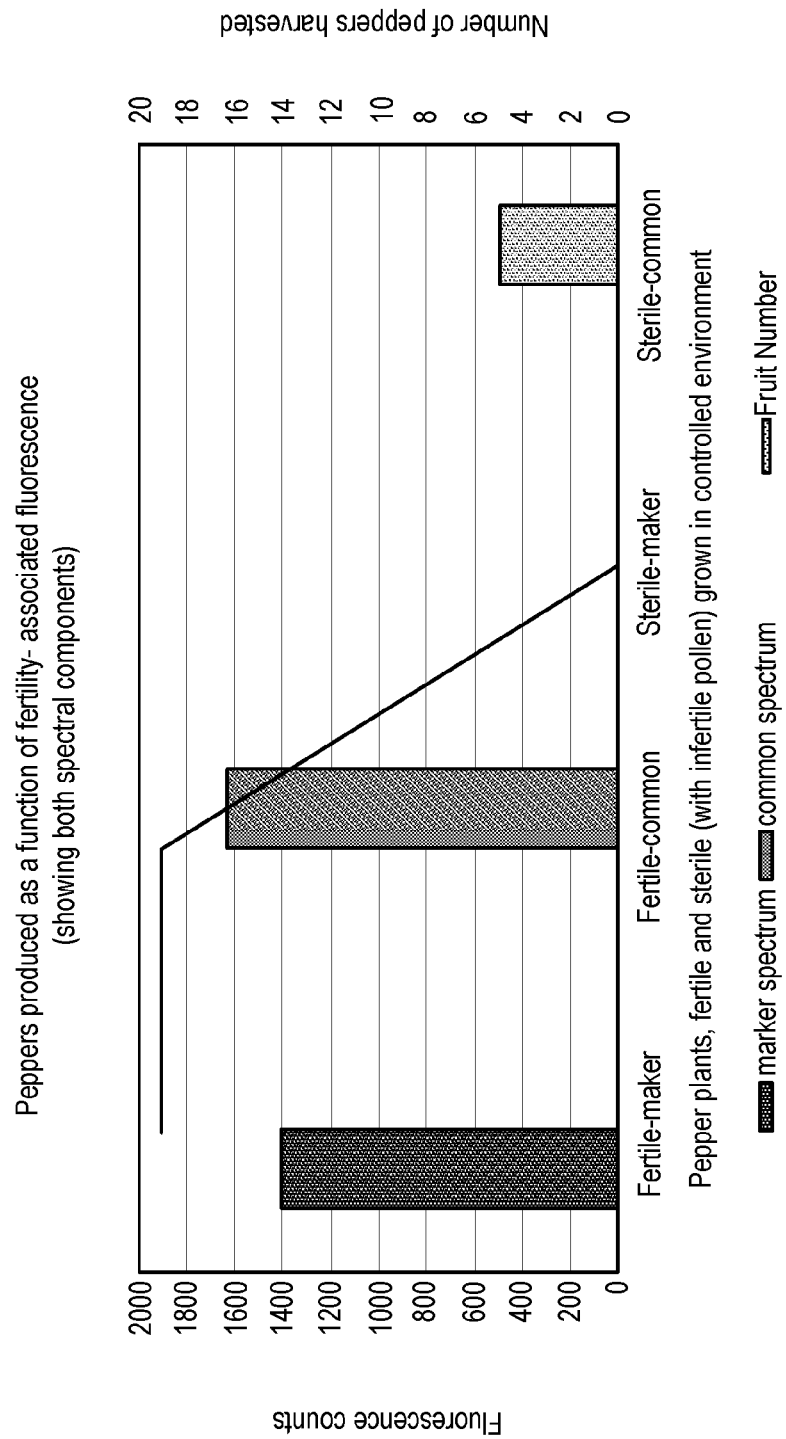
FIG. 31 illustrates a chart showing the relationship between the spectral emissions of fertile vs. sterile sweet pepper plants and the number of fruit harvested.

The shape of the weak spectral component in sterile anthers with infertile pollen suggests that other spectral components are present below the detection baseline which could probably be characterized using other acquisition parameters and/or other analytical tools. Similarly, although these results demonstrate that sterile anthers without pollen lack threshold emissions within the wavelength range between 500 nm and 650 nm, the shape of the spectral component (labeled 4 in FIG. 29) suggests that other weaker spectral components may be present in low amounts within this wavelength range as well, which could be used to distinguish those plants using alternative methods.

The results supported the pattern observed in other experiments herein where the chlorophyll emission decreased as anthers senesced. Anthers were fresh, in that they were imaged within minutes after the respective flower was harvested from the mother plant, but as flowers were harvested later and later in the flowering period of the plant, the chlorophyll-associated emissions of anthers decreased.

Next, pure spectral component data corresponding to the sterile and fertile sweet peppers anthers were uploaded into proprietary software that plotted the spectral components together in the same set of x axes. In the interest of representing the output in discernable way in grayscale, the original colored image was traced and enlarged to provide the large graph in FIG. 29. The approximate peaks of each spectral component are labeled and correspond to the labels in FIGS. 27A-B and 29.

FIGS. 30A-F provides representative examples of some of the differences in spectral signatures observed in sweet pepper in these experiments. The table below similarly summarizes the different spectral signatures observed for the different sweet pepper specimens.

| Specimen | Wavelengths (nm) | Components |
|---|---|---|
| Anther fertile + pollen | 500-650 | 2 |
| Fertile pollen | 500-650 | 2 |
| Anther fertile closed/plant | 500-750 | 3 |
| Anther infertile/or plant | 580-750 | 2 |
| Anther sterile/or plant | 650-750 | 1 |
| Dead pollen | 580-750 | 1 or 2 |

The methods described herein of distinguishing plant specimens have broad application. For example, the differences in how specimens fluoresced in the chlorophyll-associated wavelengths can be used in conjunction with these methods to identify and distinguish fertile plants from sterile plants with relatively simple equipment that is commercially and readily available. Using the teachings described herein to overcome difficulties of imaging/accessing flower parts is also anticipated, e.g. determining the fertility/sterility when plant body architectures comprise multiple inflorescences, flowers shadowed/covered by leaves (e.g. sweet pepper, soybean), tiny anthers (canola), anthers and/or stigma obscured by petals/sepals (e.g. soybean), etc. The fact that these methods produced such consistent results whether the plants were grown in a growth chamber in soil or by hydroponics in a consumer-grade, residential home set-up reveals how useful the methods disclosed herein are to a broad range of growing conditions.

As observed in the other sweet-pepper experiments, it is clear how one can use the methods described herein to predict the number of fruit a plant is likely to produce. FIG.

31 reveals the relationships observed between the spectral emissions of fertile vs. sterile sweet pepper plants compared to the number of fruit harvested. This discovery can be combined with machine learning and/or other types of algorithms to analyze data collected about plants to detect and characterize the fertility/sterility of pollen and plants, including the ability to accurately predict fruit set of a plant by assaying its spectral signatures to determine if it exhibits at least one of those described herein.

As seen in other experiments described herein, the total HSF emission of samples observed between 500 nm and 650 nm was consistently greater in fertile plants than in sterile plants with infertile pollen and/or plants without pollen. It is anticipated that one of ordinary skill in the art will realize that by adding fluorescence emissions in this way and setting a threshold level of emissions to characterize fertile vs. sterile samples, one simulates the results of using a filter-based system, which will capture both spectral emissions as a single component. Even common commercial filter-based systems can do this, and we anticipate combining this technology with the teachings herein for efficient solutions related to determining plant fertility.

The methods disclosed herein assume one of ordinary skill in the art will understand that changing certain variables related to imaging, optics, and/or microscopy and/or imaging conditions leads to changes in what might be observed. For example, the spatial resolution and/or pixel size of the optical equipment, their field of view, the lighting conditions, analytical software used, etc. are all known to affect whether a given observation is a realistic representation of the subject in question. For example, a blind test of pollen samples comprising 90% dead pollen to 10% live but infertile pollen was conducted. At 2× magnification, the sample exhibited a spectral profile with the characteristic chlorophyll-associated spike at ~685 nearly identical to FIG. 30D, but with a weak signal in the 560-630 wavelengths that did not exceed the normalized intensity threshold level of 0.45. However, zooming in on the same sample to 10× magnification produced a spectral signature wherein the weak signal appears to have resolved into a broad, above-threshold signal with a peak at approximately 560 nm, nearly identical to the spectral signature in FIG. 30C. The descriptions herein assume one of skill in the art understands how each observation represents a sample of the whole, and that multiple observations under certain conditions might be necessary to reliably characterize a sample. It is anticipated that automated imaging/optical systems will be employed to improve the accuracy and utility of these methods under different conditions. It is anticipated that these methods will be amenable to the development of algorithms capable of accurately characterizing fertility, pollen production, pollen viability, etc. to improve broadly plant science research and/or commercial crop production. Algorithms capable of rapidly sampling many image samples of a given subject (a plant, a flower, a leaf, etc.) taken under an enormous number of different conditions could be analyzed by a computer system relying on data generated using methods disclosed herein to generate a likelihood score of whether pollen was present, whether the plant was fertile/sterile, etc. Alternatively, all manner of different thresholds could be used to generate binary data, e.g. fertile vs. sterile, pollen present vs. pollen absent, etc.

Example 9: Leaf Spectral Signatures to Characterize Fertility/Sterility

Figure 32:
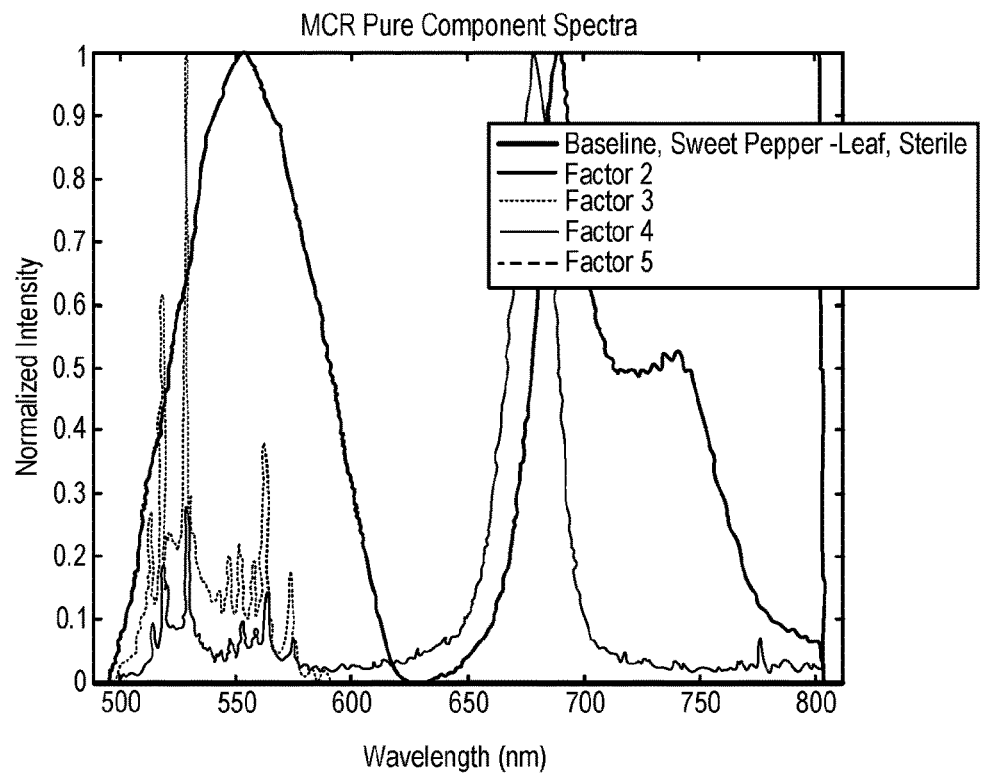
FIG. 32 illustrates spectral data comparing the leaves of sterile sweet pepper plants and the leaves of fertile sweet pepper plants.
Figure 32:
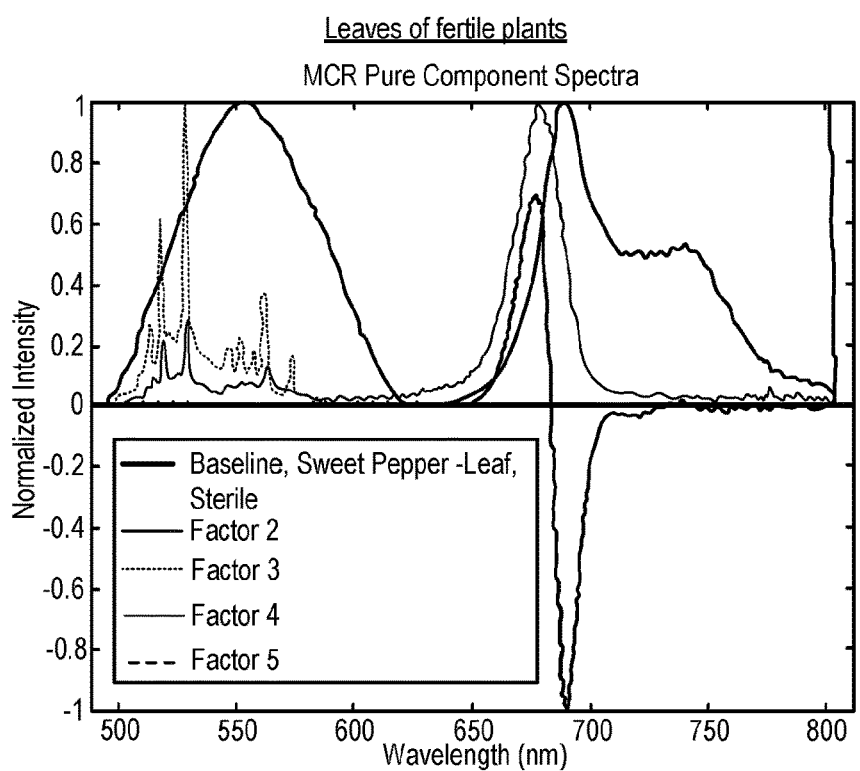

HSF microscopy of leaves from fertile sweet pepper flowers/plants using a chlorophyll blocking filter and no mask revealed differences between sterile plants and fertile plants (FIG. 32). The most obvious differences occur between about 650 nm and about 750 nm, including a dramatic chlorophyll-b shift absent in sterile leaves, which could be used in conjunction with methods disclosed herein to differentiate sterile plants from fertile plants. Spectroscopy performed in fertile and sterile sweet pepper specimens (leaves, inflorescences with open and closed flower buds, and open flowers) also showed spectral differences between plants with fertile, infertile and sterile anthers within at least the wavelength range from about 500 nm to about 800 nm.

HSF microscopy of the adaxial sides of fertile vs. sterile sweet pepper leaves were also compared. When red and green were assigned to the pure spectral components disclosed herein, RGB images at low magnification and low spectral resolution of fertile and sterile leaves were clearly distinguishable.

Example 10: Differentiating Fertile Vs. Sterile Plant Tissues with a Handheld Device (HSF Spectroscopy of Leaves, Flowers, and Inflorescences with a JAZ Spectrometer)

Figure 33:
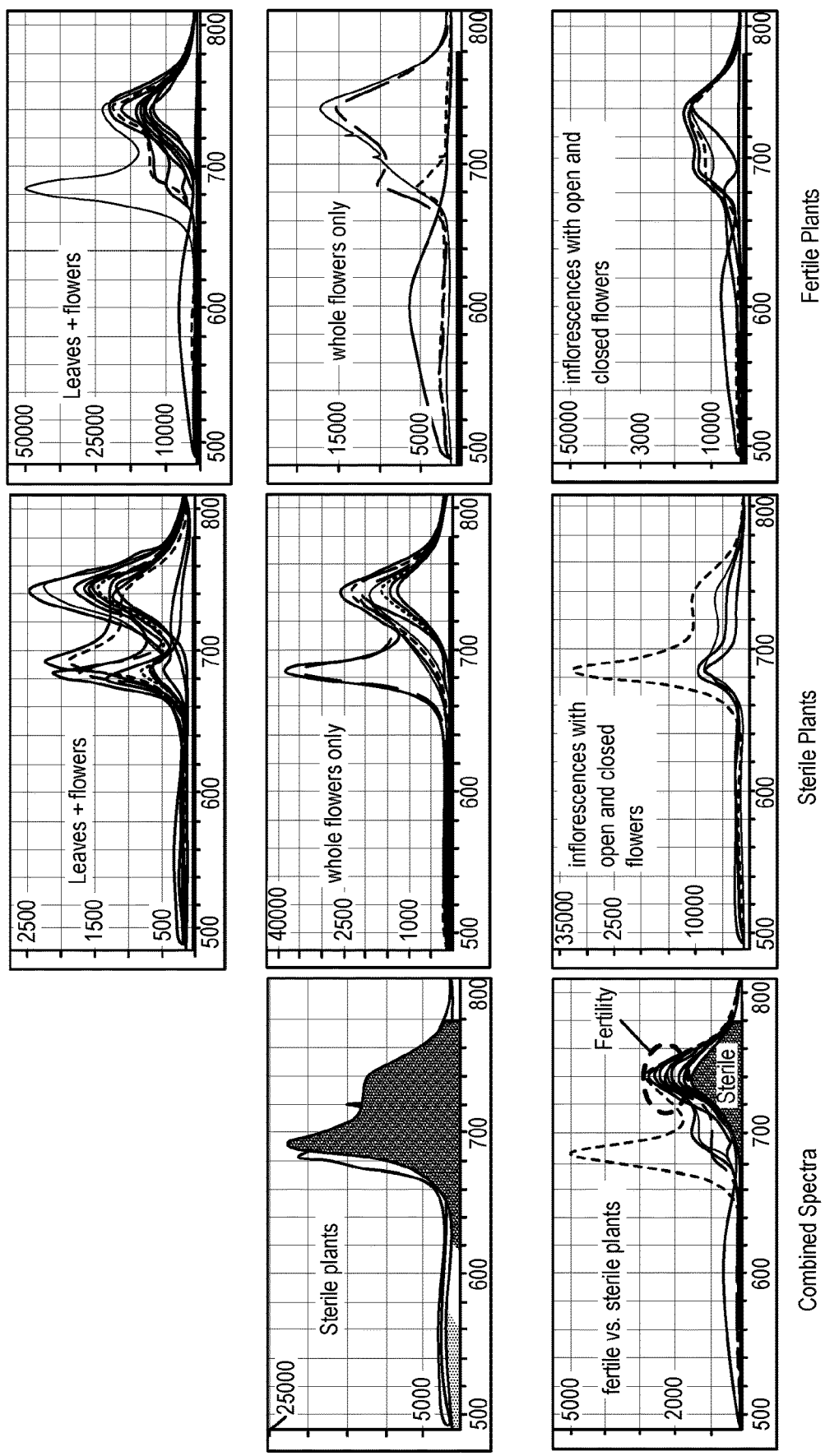
FIG. 33 illustrates spectral data for fertile and sterile sweet pepper plants separately and combined.

A JAZ spectrometer and UV/blue excitation was used to collect, compare, and contrast the HSF signatures of leaves, inflorescences, and whole flowers of fertile and sterile plants. Readings were taken in full darkness. The results (FIG. 33) reveal differences in the spectral signatures of all three organ/tissue types that can be used to differentiate sterile and fertile plants. Again, this reveals that the methods disclosed herein are not limited to microscopy and/or laboratory procedures and can be used in conjunction with a wide range of technologies that improve the efficiency of identifying sterile vs. fertile plants and plant parts. For example, the fact that it is not necessary to analyze the anthers of a plant to determine whether it is sterile or not means that the methods disclosed herein are particularly amenable to automation, which may lack the dexterity to analyze tissues on difficult to reach, hidden, or obscured parts of the plant, to nevertheless determine the fertility of a plant without discretely sampling a specific tissue. The surprising discoveries disclosed herein enable machines to grasp and/or analyze an assortment of different tissues (e.g. a single sample containing an inflorescence, closed flowers and a few leaves, or some other combination) and still reliably distinguish fertile plants from sterile plants. Portable and/or filter-based sensors mounted to ground/aerial vehicles could be used in conjunction with these methods, including manual systems comprising goggles/glasses, helmets, specialized contact lenses, etc.

Example 11: Useful Spectral Markers and/or Profiles

Useful spectral markers and/or profiles described herein appear surprisingly conserved among all angiosperms.

Methods disclosed herein were tested on a range of distantly-related crops: monocot corn (Zea) and the dictos cotton (Malvaceae), canola (Brassicaceae), and sweet pepper (Solanaceae). Spectral analysis software was used to compare the spectral profiles the pollen from each crop generated when plotted together (FIG. 42).

Figure 34A:
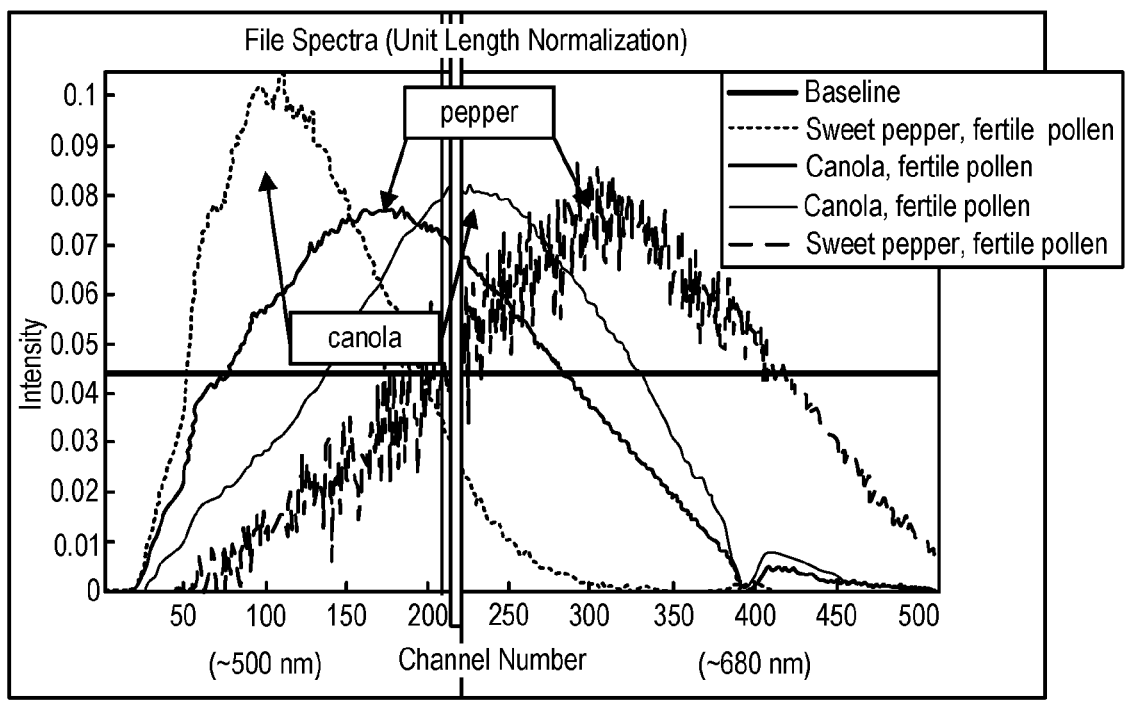
FIG. 34A illustrates spectral data for sweet pepper and canola pollen.

FIG. 34A is an example of how the methods disclosed herein can be used to differentiate pollen from two different species: canola and sweet pepper. Both species were similar in the combined comparison in that they emitted two spectral components in the 100-400 channel number (~500 nm to 680 nm wavelength). However, the two spectral components of the pepper were shifted toward the red, with one pepper spectra emitted between the two spectra of canola (cell wall compositional differences, among other factors, may account for this) with the peaks of each component clearly discernable from one another. Thus, although the spectra were detected within about the same wavelength range, they are nevertheless distinguishable between crop species.

Figure 34B:
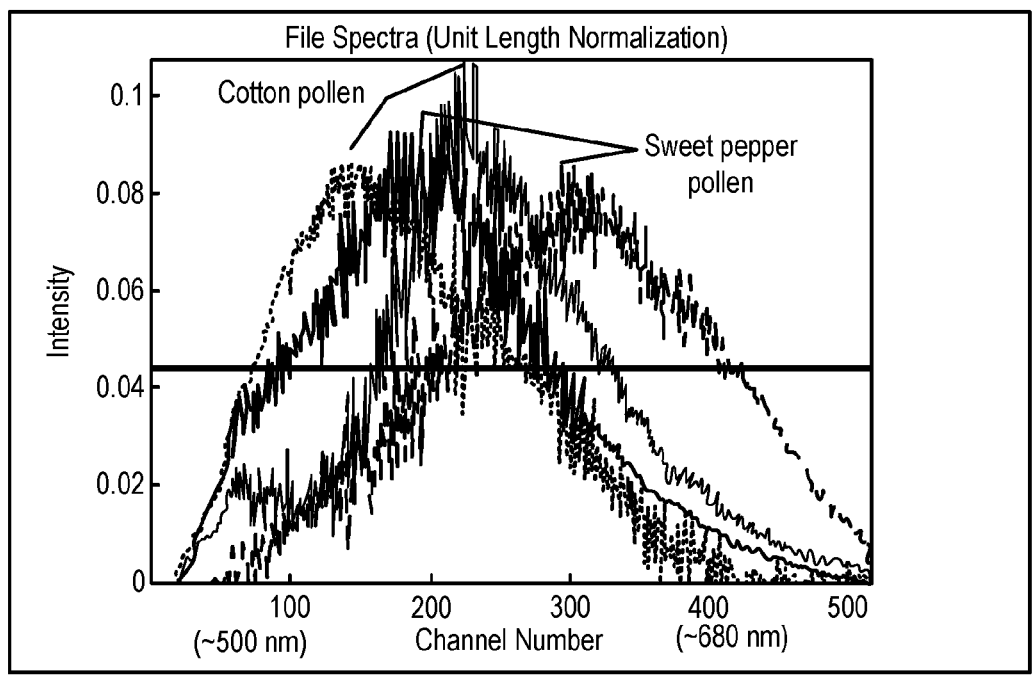
FIG. 34B illustrates spectral data for sweet pepper and cotton pollen.

FIG. 34B shows the spectral signatures of fertile cotton pollen and sweet pepper pollen plotted together, revealing again that both species emitted two clear signals in the 100-400 channel number (~500 nm to 680 nm wavelength), and again, the pepper pollen emissions appeared shifted toward the red, as compared to the cotton. The alternating peaks of the two species signals can be distinguished and leveraged by an algorithm to determine if image data contains spectral markers related to fertility.

Figures 34C, 34D:
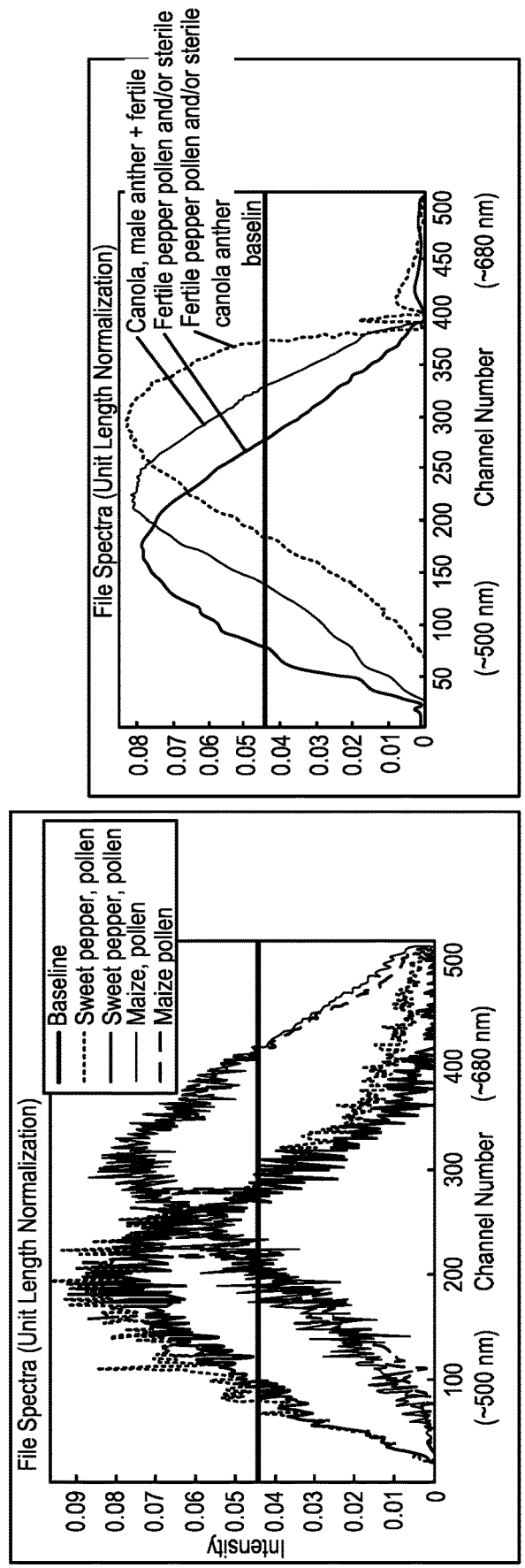
FIG. 34C illustrates spectral data for sweet pepper and maize pollen.
FIG. 34D illustrates spectral data for sweet pepper and canola pollen and/or anthers.

FIG. 34C shows that corn pollen and sweet pepper pollen are almost entirely overlapping. While it is expected that developing a reliable system for differentiating the live pollen from these two species would likely be more difficult than it would be for other species studied herein, these results do confirm that the methods disclosed herein (e.g. determining fertility/sterility of pollen/plants based on detecting certain spectral markers disclosed herein) are applicable among a vast range of distantly-related species. Furthermore, as explained elsewhere herein, anthers emit a chlorophyll-associated peak at about 688 nm, so that can be used to differentiate corn from pepper.

FIG. 34D reveals that the spectra from live, fertile sweet pepper pollen (left and right peaks) appear to overlap the spectra of sterile canola anthers (discussed elsewhere herein), and that these overlapping spectral signatures from both species are fully distinct from the spectral signatures obtained from canola anthers with fertile pollen (middle peak).

These results confirm that spectroscopy and/or hyperspectral technologies will be able to detect and/or differentiate mixtures of pollen from different species and distinguish live vs. dead pollen. Focusing on specific wavelengths, using high spectral resolution, and extending the wavelengths assayed are all anticipated ways of improving the efficiency of the methods disclosed herein. Thus, depending on the spectral emissions and agricultural applications, tools can be developed that span from low cost devices (such as but not limited to glasses, helmets, contact lenses, smart phones, and handheld imaging or analytical devices) to higher cost devices, as well as devices used as a single unit or in combination with other devices, like cameras, sensors, spectrometers and other analytical tools, for invasive and/or non-invasive applications, in the laboratory, growth room, vertical farms, and other forms of artificial environments, etc. or in the field from any sort of vehicle capable of moving the sensor into a desired position/orientation.

The table below summarizes the spectral data for canola:

| Specimen features | Wavelength range | Spectral Components |
| --- | --- | --- |
| Fertile Anther | 512 to 529 nm + 570 to 590 nm | 5 total |
| Sterile Anther | 550 nm ± 10 nm | 3 total |
| Petals, sterile plant | <550 nm and 680 nm | 2 total |
| Petals, fertile plant | 550 nm to 650 nm | 3 total |

Example 12: Generation and Preparation of Cotton Plant Specimens for Analysis

A population of cotton seeds carrying genetic male-induced sterility that was allegedly segregating at a 1:1 ratio was sowed in soil pots and grown in a growth chamber following standard methods known in the art. As the plants flowered, multiple flowers from each plant were harvested every few days over a 2-3-week period (plants were regularly trimmed throughout this period to extend the flowering period and reduce leaf density and branch weight), and separated into fertile and sterile samples, depending on which parent from which they were drawn. Sterility was confirmed in six of fifteen of the plants by visual examination, microscopy, and 0% fruit set. Imaging was performed on fresh, fixed (3.7% formaldehyde) and frozen (−80° C.) flowers, anthers and pollen, as well as fresh dead pollen and leaves/leaf discs from fertile and sterile cotton plants. Petals, anthers, pollen and other plant parts were carefully analyzed by the same HSF microscopy, digital imaging, HSF spectroscopy, and confocal and scanning electron microscopy methods described herein for other crops.

Figure 35:
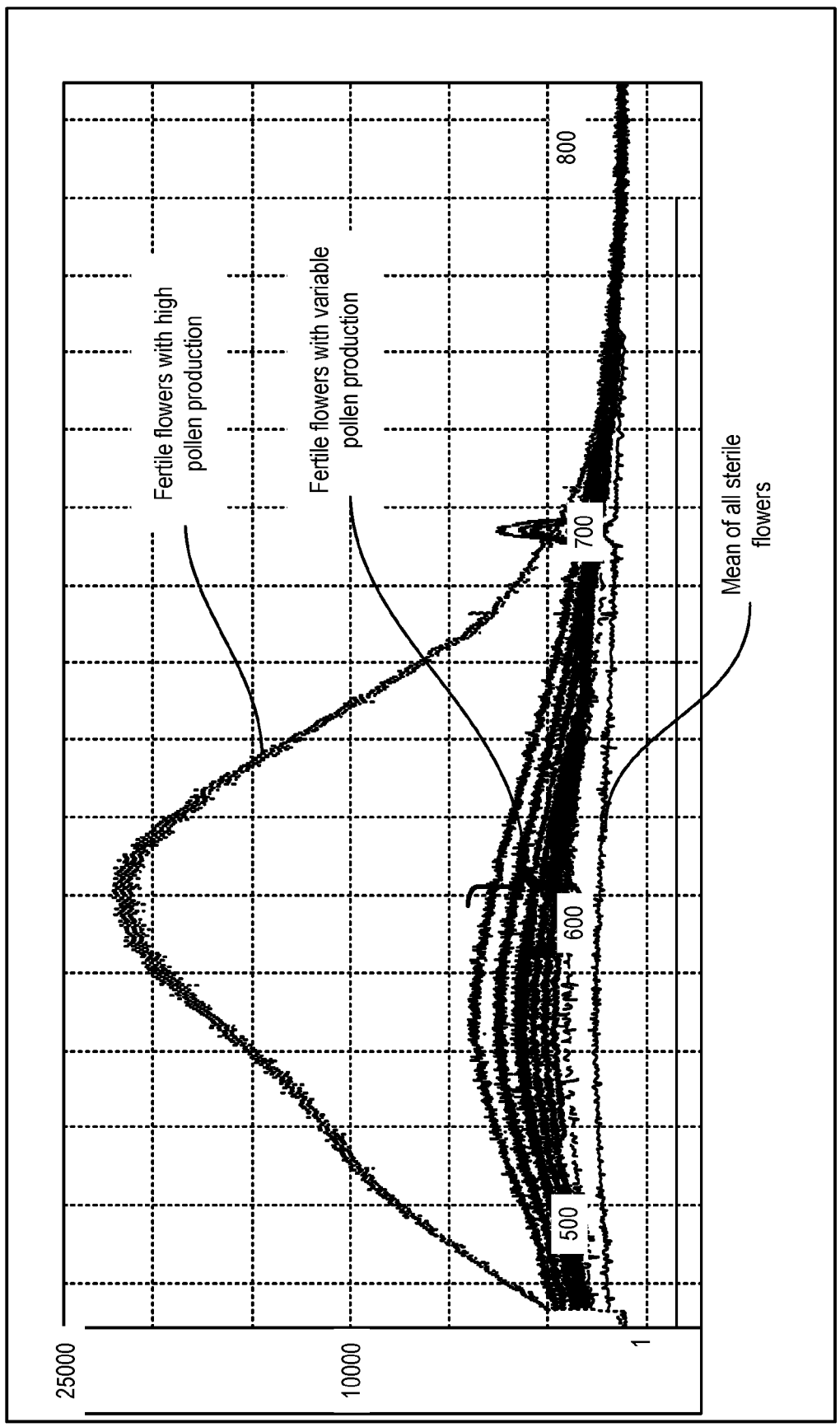
FIG. 35 illustrates microscopy data comparing fertile flowers with high pollen production, fertile flowers with variable pollen production, and sterile flowers for cotton plants.

Example 13: Results of Imaging, Spectroscopy, and Microscopy on Cotton Anthers and Pollen FIG. 35 reveals the pronounced difference that was discovered between the fluorescence of fertile cotton anthers versus sterile cotton anthers in the 500-700 nm range when the JAZ spectrometer was used with UV/blue excitation: fertile anthers exhibited pronounced pollen and chlorophyll-related emission(s) in that range while the sterile anthers did not. The discovery of this clear difference enables devices capable of making use of this newfound distinction to sort fertile plants, their organs, or their cells, from sterile plants, their organs, or their cells.

FIGS. 36A-D also shows results of HSF microscopy performed on cotton. Both the mature anthers shedding fertile pollen and the GMS-sterile anthers without pollen exhibit two HSF spectral emissions between about 500 nm and about 650 nm. This spectral signal overlaps the two prominent spectral emissions observed in the samples of fertile anthers. The spectral component data of the two classes of anthers was analyzed with software that combines the plots into a single graph. The "combined" graph in FIG. 44 shows that although the spectral signatures of two classes of anthers in the 500-650 nm bands were similar in this study, with overlapping peaks, the presence of the large spikes in the 650-700 nm range in the sterile samples make the spectral signatures of the two classes nevertheless easily distinguishable. Furthermore, certain below-threshold spectral differences between the sterile and fertile anthers were detected, e.g. those indicated by the dashed oval from about 500-650 nm of the combined graph, that suggest the methods disclosed herein could be adapted to distinguish sterile vs. fertile anthers and plants in those wavelengths as well (e.g. by improving the resolution of the imaging to better separate spectral components).

Figure 36B:
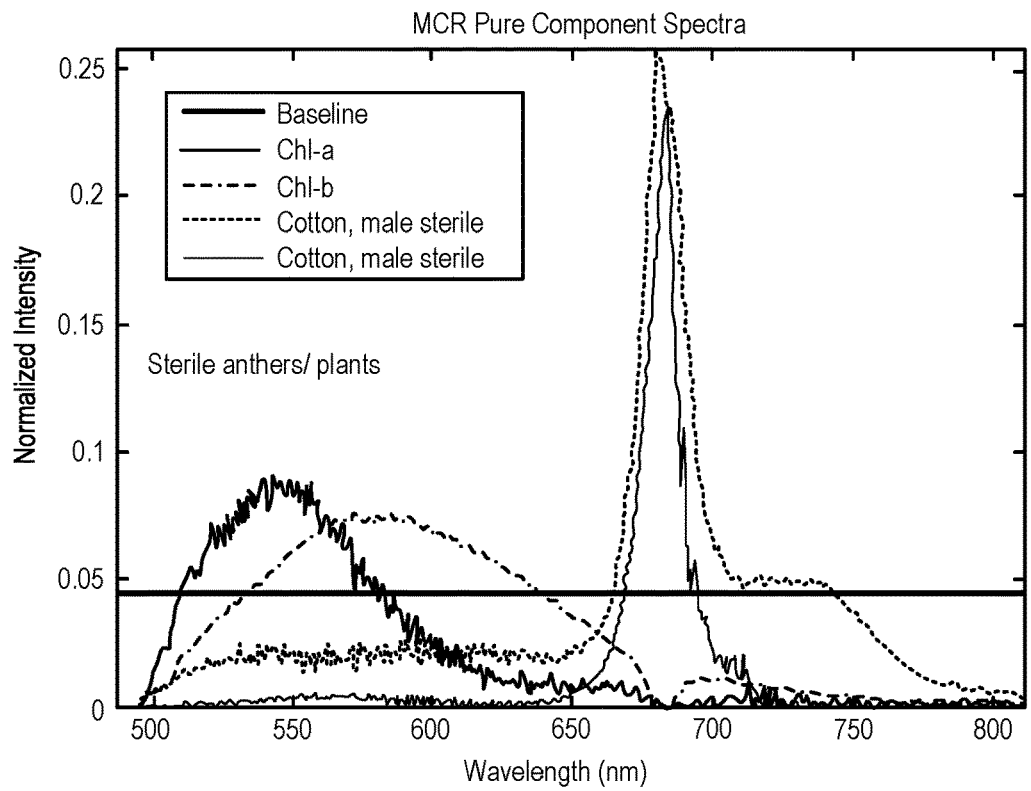
FIG. 36B illustrates spectral data of sterile anthers/cotton plants.
Figure 37B:
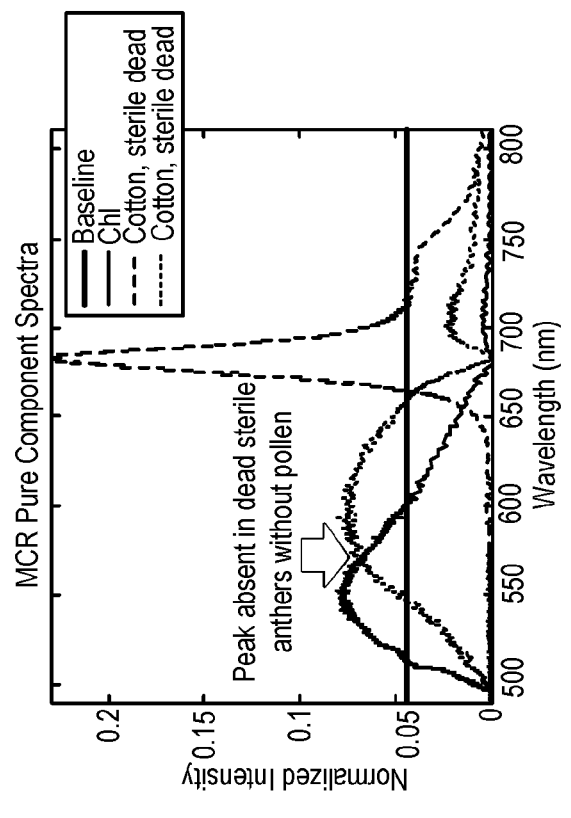
FIGS. 37A-D illustrate spectral data of fertile dead, sterile dead, and fertile cotton pollen.
Figure 37A:
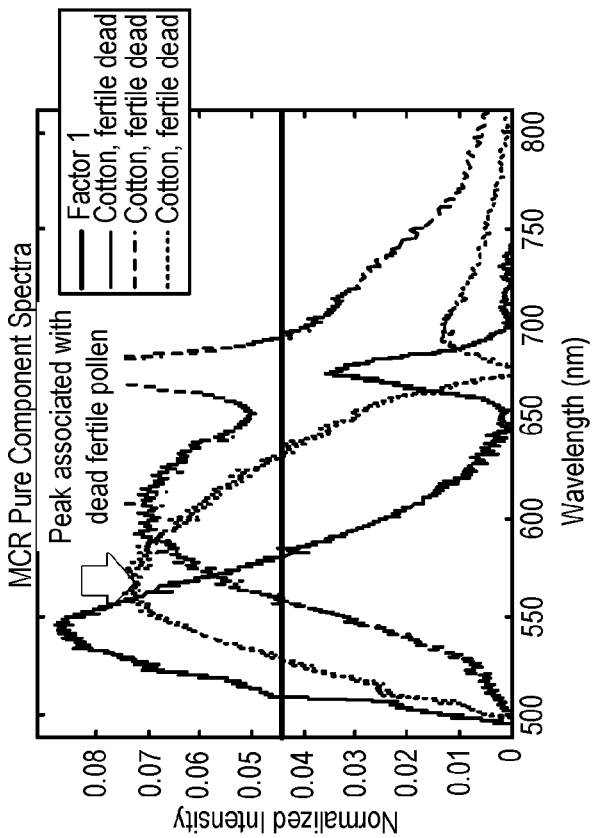
Figure 37D:
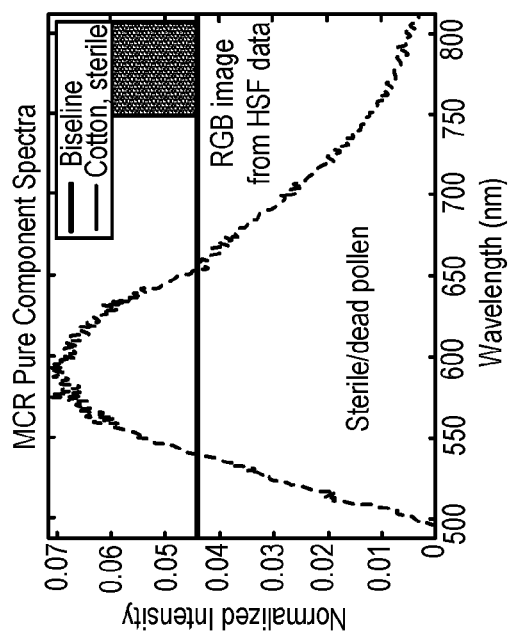
Figure 37C:
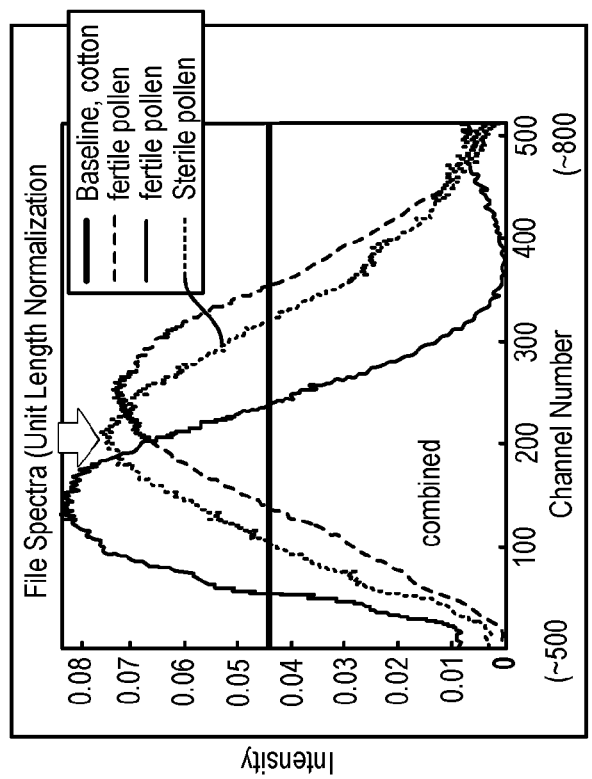

FIGS. 37A-D reveals how the methods disclosed herein enable the use of HSF profiles to distinguish between sterility related to senescence (e.g. plants that were producing fertile pollen at one point, but have since stopped) versus congenital sterility (i.e. plants that never produced fertile pollen), e.g. GMS. Thus, this third spectral component can be used in conjunction with methods disclosed herein to distinguish fertile pollen from infertile pollen, and determine whether it is viable or inviable. Anthers that at one point were producing fertile pollen (but the pollen is no longer viable) exhibit a spectral component between the two peaks between 500 and 650 nm that otherwise appear in the sterile (GMS) anthers (FIG. 36B). FIG. 37C also shows the spectral emissions of live, fertile pollen versus aborted, sterile pollen, (e.g. fertile vs. senesced) combined into a single plot using software. This confirms the presence of a new spectral component (indicated by the arrow in FIG. 37A-C) that is only present when fertile but no longer viable (i.e. dead) pollen is present and/or when living, but infertile pollen (e.g. from GMS) is present.

Figure 36A:
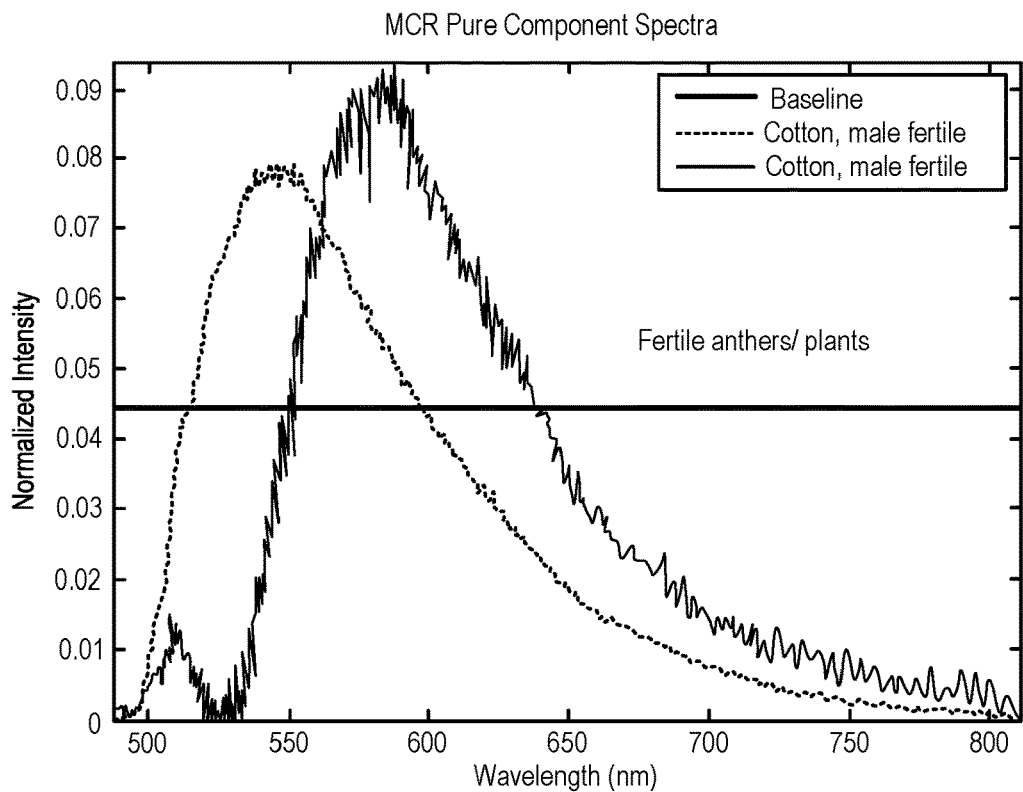
FIG. 36A illustrates spectral data of fertile anthers/cotton plants.
Figure 36C:
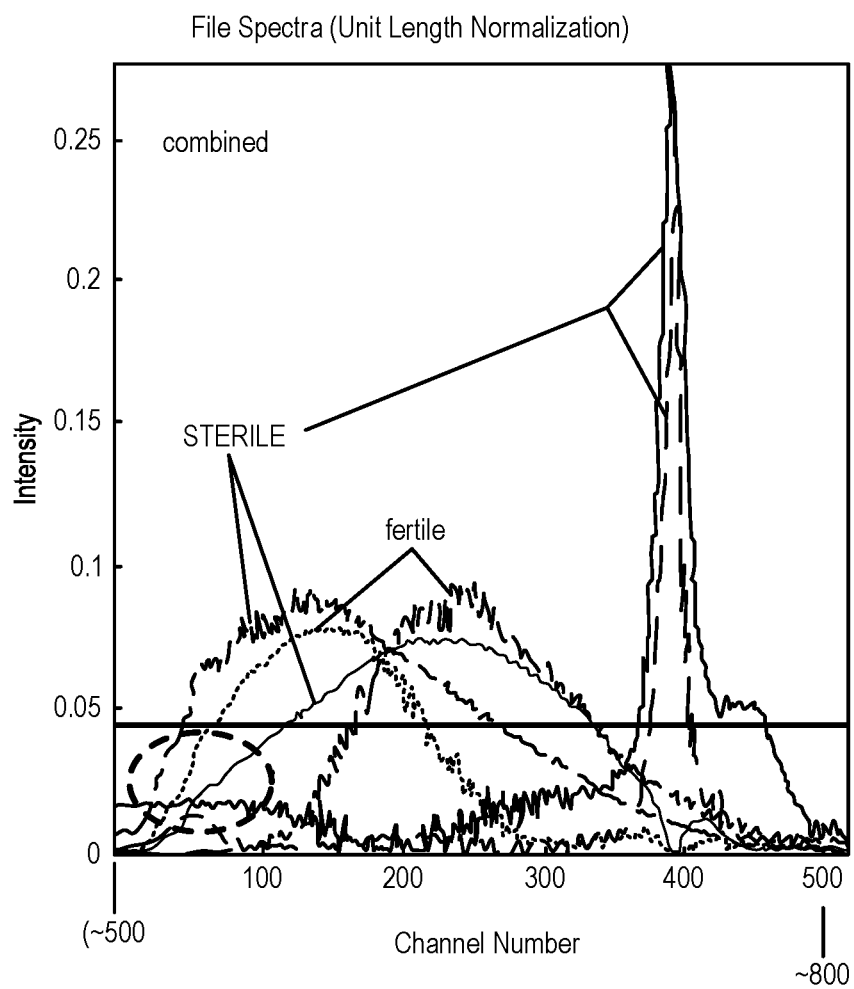
FIG. 36C illustrates combined spectral data of sterile and fertile cotton plants.

In certain embodiments, the presence of fertile cotton pollen, whether live or dead, can be detected at low spatial resolution (e.g. 2x) using methods described herein by examining HSF profiles at about 550 nm (±30 nm) associated with either live or dead fertile pollen, as depicted in FIGS. 36A-C. At this resolution, the two emissions in that range which we can see in A17 form a single component that can be used as a marker indicating the presence of fertile pollen while spectral profiles of sterile (GMS) anthers (i.e. infertile pollen) do not show spectral emissions below 650 nm. These differences could be used with methods described herein to distinguish the anthers of sterile plants versus the anthers of fertile plants. It is assumed that one of ordinary skill in the art understands how to adjust magnification, exposure times, focus, etc. in similar ways to improve imaging conditions and resolve different spectral components.

Thus, HSF imaging revealed at least one pure spectral component exhibited by viable, fertile anthers and/or pollen of cotton with an emission peak at about 600 nm±20 nm that is absent in sterile anthers that have viable but infertile pollen, or no pollen. Sterile pollen (i.e. infertile, aborted, incapable of fertilization), when present in sterile (GMS) anthers shows a distinct spectrum with an emission peak around 565 nm±10 nm. We anticipate leveraging the spectral differences in chlorophylls and carotenoids disclosed herein in conjunction with the methods disclosed herein to distinguish fertile from sterile anthers and/or to monitor anther maturity and viability, as described herein for corn tassels and other crops.

Fertility-associated wavelengths for cotton range from 500 nm to 650 nm, whereas sterility-associated wavelengths span from 500 nm to 780 nm (500 nm to 780 nm for infertile anthers; 680 nm to 780 nm for sterile anthers.

Example 14: Results of Imaging and Microscopy on Cotton Petals and Leaves

Figure 38:
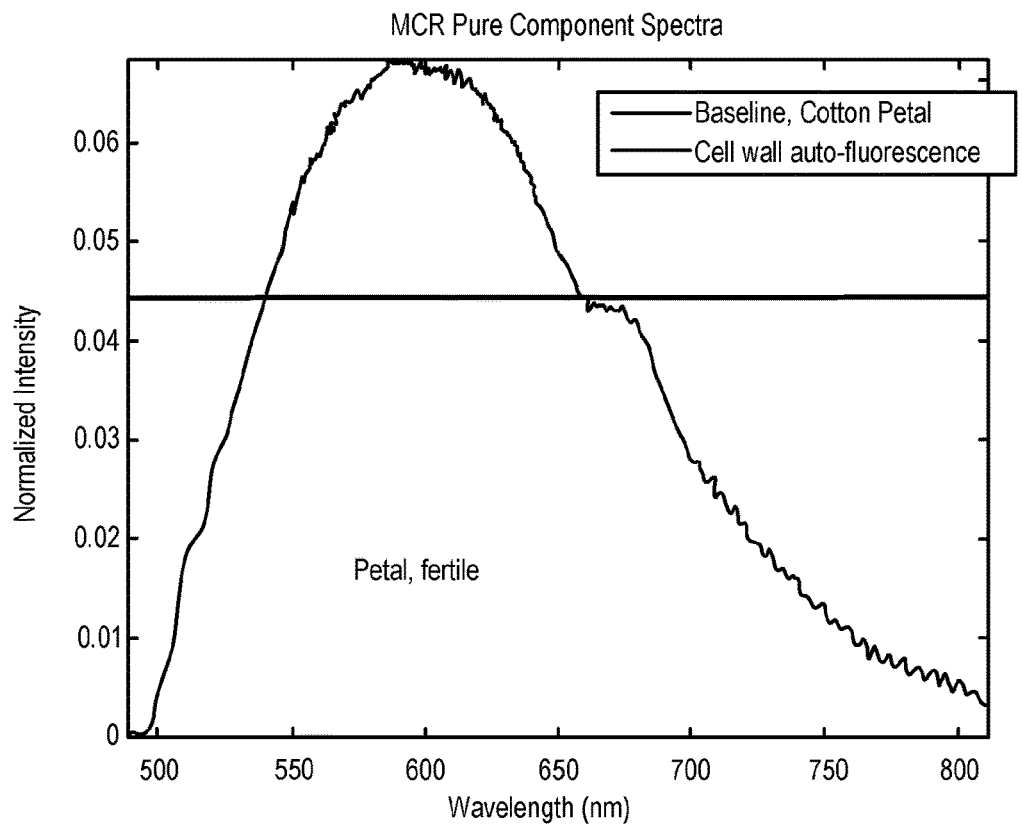
FIG. 38 illustrates spectral data of fertile and sterile cotton petals.
Figure 38:
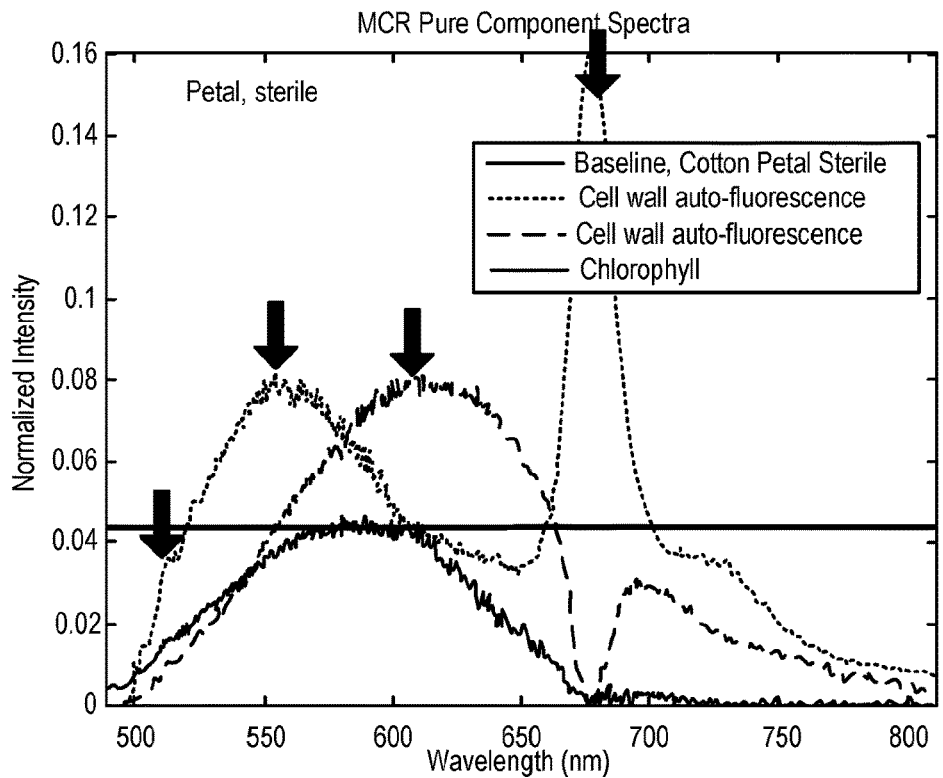

Spectral profiles of fertile and sterile (GMS) cotton flower petals reveal spectral differences that can be used with methods disclosed herein to distinguish between fertile and sterile plants (FIG. 38). The petals of fertile plants generated a spectral profile comprising a single component with a peak at approximately 600 nm. On the other hand, the petals of the sterile plants produced a spectral profile comprising at least three spectral components; one with a peak at about 550 nm, another with a peak at about 625 nm, and another large chlorophyll-associated peak at about 690 nm. Another feature was observed at about 510 nm (black arrow) that could be used to differentiate the petals of fertile versus the petals of sterile plants.

Figure 39:
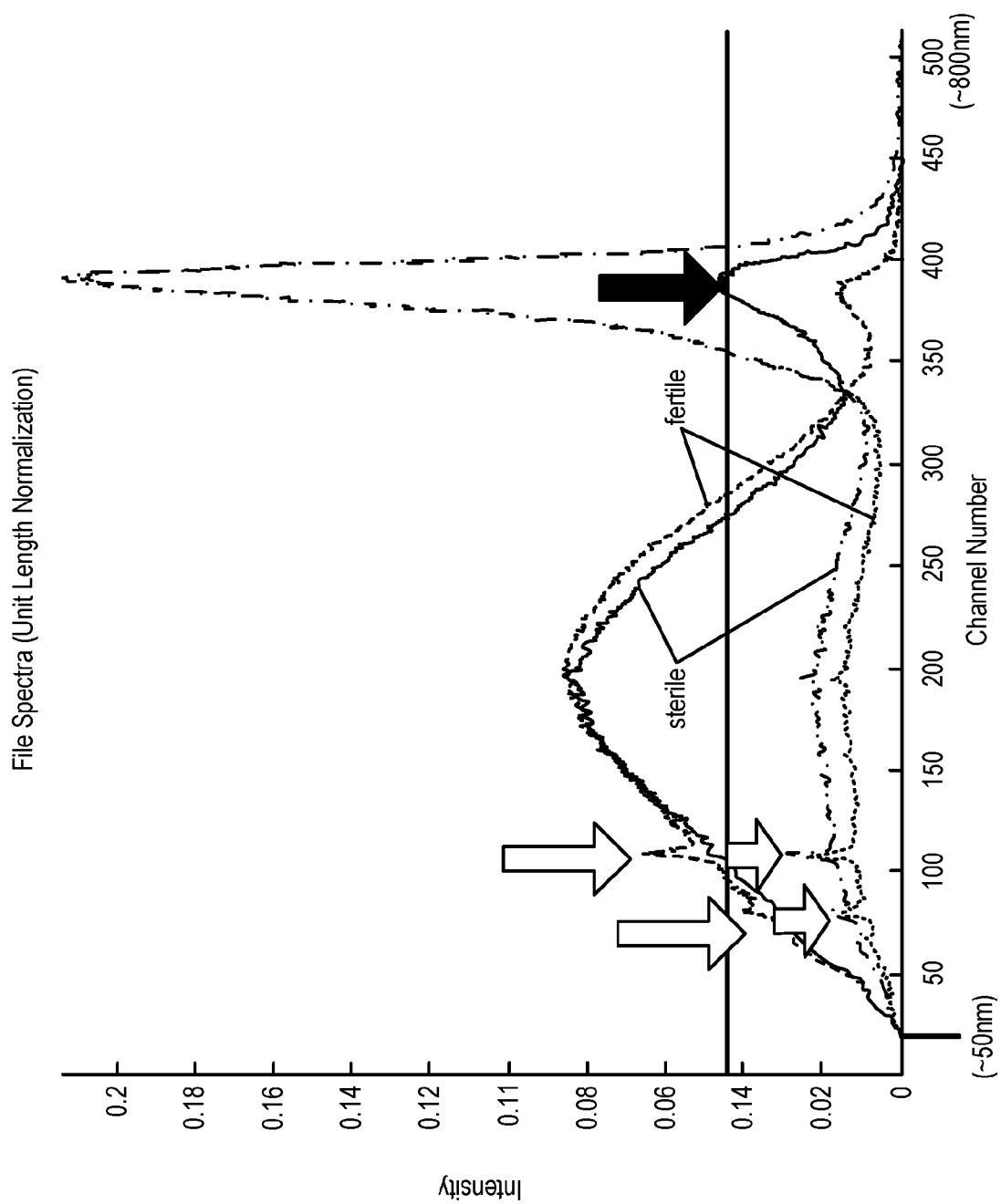
FIG. 39 illustrates spectral profiles of fertile cotton flowers with viable pollen and sterile cotton flowers.

HSF microscopy of cotton plant leaves revealed differences in spectral components that could be used in conjunction with methods disclosed herein to distinguish fertility (FIG. 39). The spectral differences observed between the leaves of fertile plants versus sterile plants were more easily seen in RGB images of whole leaves. It is anticipated that methods described herein could be combined with sensitive spectral sensors with narrow waveband filters could be adapted to differentiate the leaves of sterile cotton plants from the leaves of fertile cotton plants. Analytical tools that can detect and identify carotenoids could also be used.

Example 15: Comparing Spectral Signatures of Cotton Pollen vs. Corn Pollen

Figure 40:
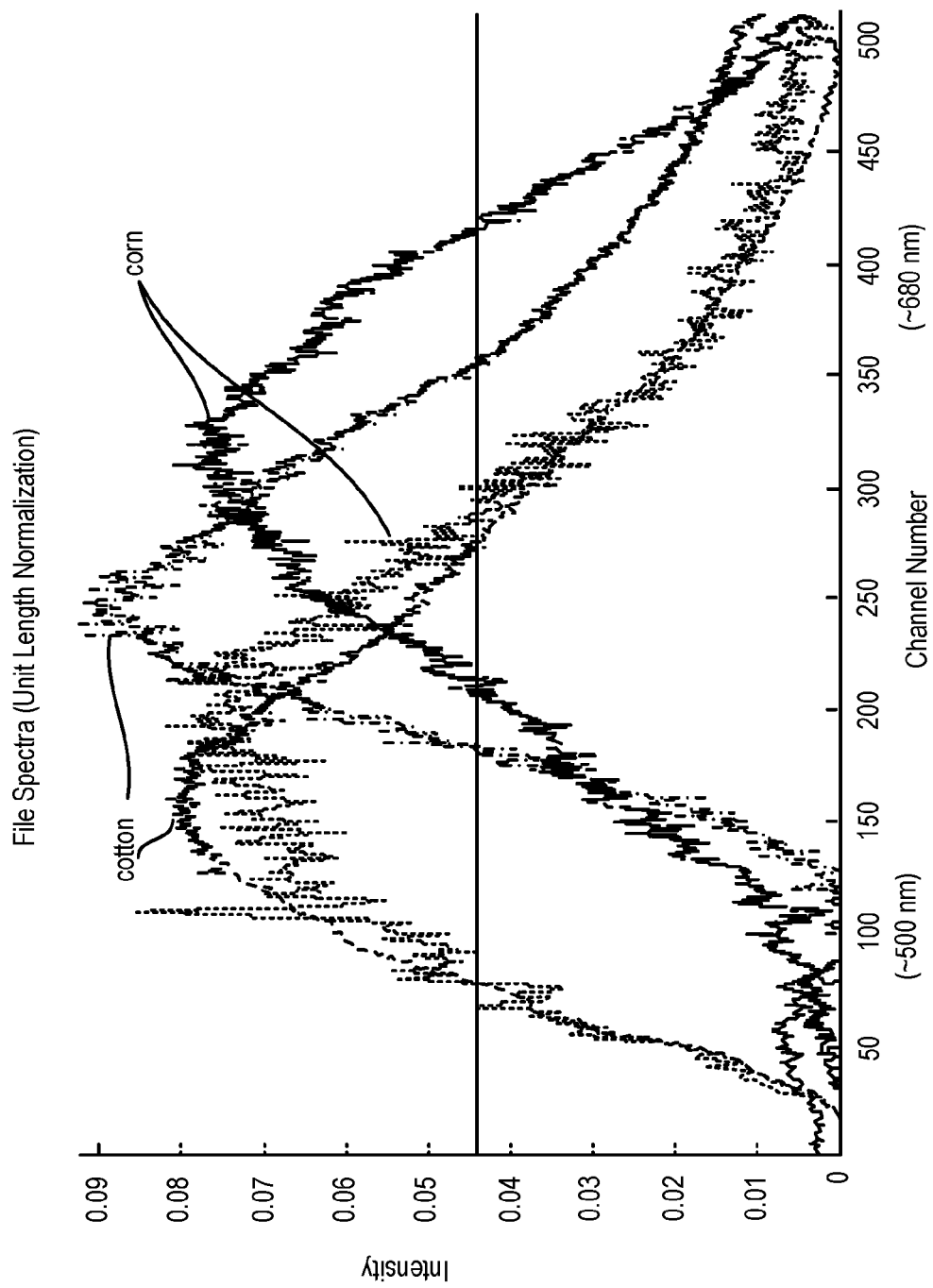
FIG. 40 illustrates spectral data of live pollen from cotton and corn.

The spectral components of live pollen from cotton and corn were analyzed by software to plot on them on the same x axis (FIG. 40). Although live pollen from the two species exhibited spectral profiles over a similar set of wavelengths (500 nm-650 nm, corresponding to channel numbers 20 to 420), both the cotton pollen and the corn pollen produced at least one component with a peak that did not overlap a component of the other species, corresponding to peaks at about channel 250 (cotton) and channel 340 (corn) in FIG. 404. The black arrow points to an emission from the sterile corn pollen, which is completely overlapped by the sterile cotton emission at those same wavelengths. It is anticipated that methods disclosed herein could be used to leverage these differences in order to be able to detect and differentiate cotton pollen from corn pollen. These results also support the conclusion that other species of crop plants exhibit spectral signatures in the wavelengths from about 500 nm to about 750 nm that can be used with methods disclosed herein to detect and distinguish fertile plants and/or anthers from sterile plants and/or anthers.

Example 16: Digital, Filter-Based Imaging with UV/Blue Excitation

Digital, filter-based imaging with UV/blue excitation revealed emission differences between fertile anthers and sterile anthers in the green and red channels. While the fertile anthers of cotton all fluoresced brightly throughout their surfaces under GFP/FITC filter, the anthers of sterile flowers only fluoresced on their edges, in semi-circular patterns. Under the Rho/TRITC filer, fertile cotton anthers fluoresced brightly, while the anthers of sterile flowers were black. The differences between cotton and sweet pepper reveal that there is no one specific method guaranteed to give great results for all species, all tissues, etc. However, it is assumed that one of ordinary skill in the art will understand the need to try different imaging conditions, magnifications, lighting environments, filters, etc. for each species they are observing in their specific set of circumstances.

Example 17: HSF Spectroscopy with UV/Blue Light Excitation

A JAZ spectrometer can be used to differentiate fertile cotton flowers from sterile cotton flowers. The spectral profiles of fertile cotton flowers with viable pollen and sterile cotton flowers appeared almost identical to that for sweet pepper in FIG. 35. A large set of spectral emissions were observed from a few flowers of fertile plants; a second set of emissions at much lower intensity were observed from flowers collected from fertile plants that nevertheless had some anthers which were not producing as much pollen, and a final, very low or no-intensity emission from all flowers of sterile plants. Fluorescence intensity variations were common for fertile flowers as a function of how much pollen was present on the anthers (dehiscent vs. non-dehiscent). These spectral results were reproducible amongst independent experiments.

As in the experiments with other species described herein, confocal and SEM were used to confirm the viability/fertility of cotton pollen and anthers.

Example 18: Field Experiments with Handheld Devices

Figure 12B:
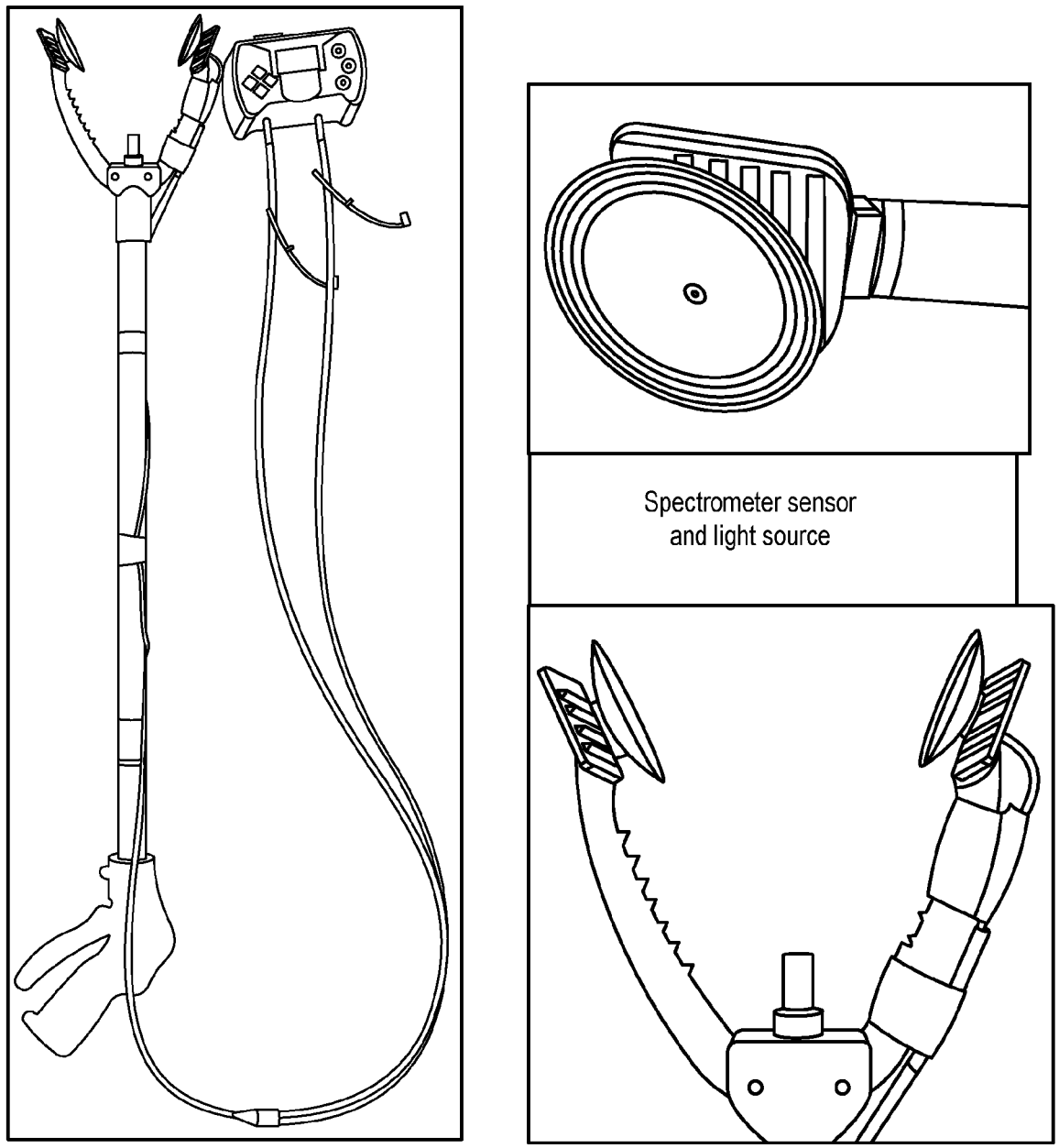

During the 2018 growing season, experiments were conducted to adapt the innovations described herein for use in field conditions. FIG. 12B shows one probe that was developed and was used to collect HSF spectroscopy data in conjunction with a JAZ spectrometer. The probe comprised two articulating arms at the end of an extended pole that clamped two suction cups together when a lever was pulled. The two suction cups were used less for their ability to make airtight seals on surfaces, but instead, used for their ability to clamp onto a sample, holding the sample between the cups with the lips of the cups fitting together to form a sort of light barrier around (part of) the subject, i.e. wherein the two halves of the cups formed a small darkened chamber between them where the sample is held when clamped together. At the center of one cup was placed the spectrometer probe and its light source. Thus, when the device was used to clasp a specimen (e.g. a corn tassel), the suction cups formed a light barrier around the specimen that reduced the spectral noise of ambient light, and the JAZ spectrometer could be activated to capture data about the specimen. Other versions of this preliminary proof of concept are envisioned and tested. In certain embodiments, the methods disclosed herein can be used to detect pollen on double haploid plants and/or the response of plants to different herbicides.

The grabber+JAZ device described above was used to collect spectroscopic data on tassels, leaves, and other plant parts of corn plants growing in research fields. Tests on plants known to be sterile because they carried the CMS trait, or sterile because they carry the RHS (Roundup Hybridization System) trait and were sprayed with Roundup. The spectral signatures of those plants were compared to fertile plants, either non-CMS or RHS plants not sprayed with Roundup. The results of the tests were plotted and compared to the level of sterility exhibited by the plants to compare the ability of these methods to differentiate between sterile, fertile, or a scale of fertility from 1-9 due to nuclear or cytoplasmic genetic breakage (recombination) of the CMS and/or RHS (Roundup Hybridization System) trait. The actual states of the plants' pollen production were confirmed by scouting and optical microscopy.

Figure 41:
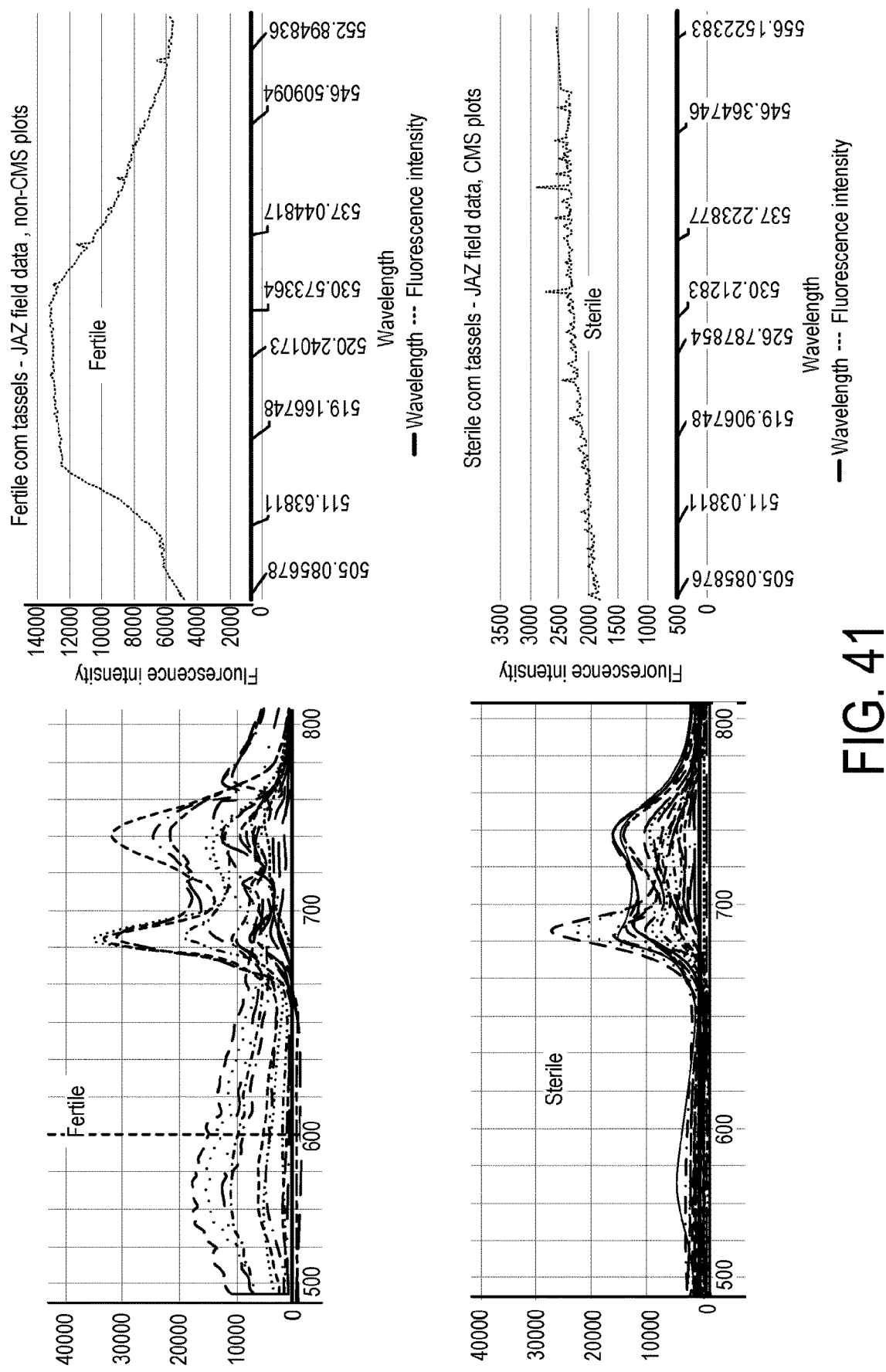
FIG. 41 illustrates combined data collected in the field for fertile and sterile corn plants.

FIG. 41 reveals the combined data collected in the field. Although clear differences could be distinguished between the fertile and sterile corn plants in the 640-800 nm range of wavelengths, the most obvious differences were found to be in the 500-560 nm range. There, clear differences were observed in the spectral profiles of the two plant types which were used in conjunction with methods disclosed herein to identify and distinguish fertile plants/anthers vs. sterile plants/anthers under live field conditions. Fertility levels detected in plants experiencing a restoration of fertility due to CMS breakage exhibited 1.5 to 2.0 times higher fluorescence intensity compared to those at CMS rating 1 (100% sterile).

Figure 42A:
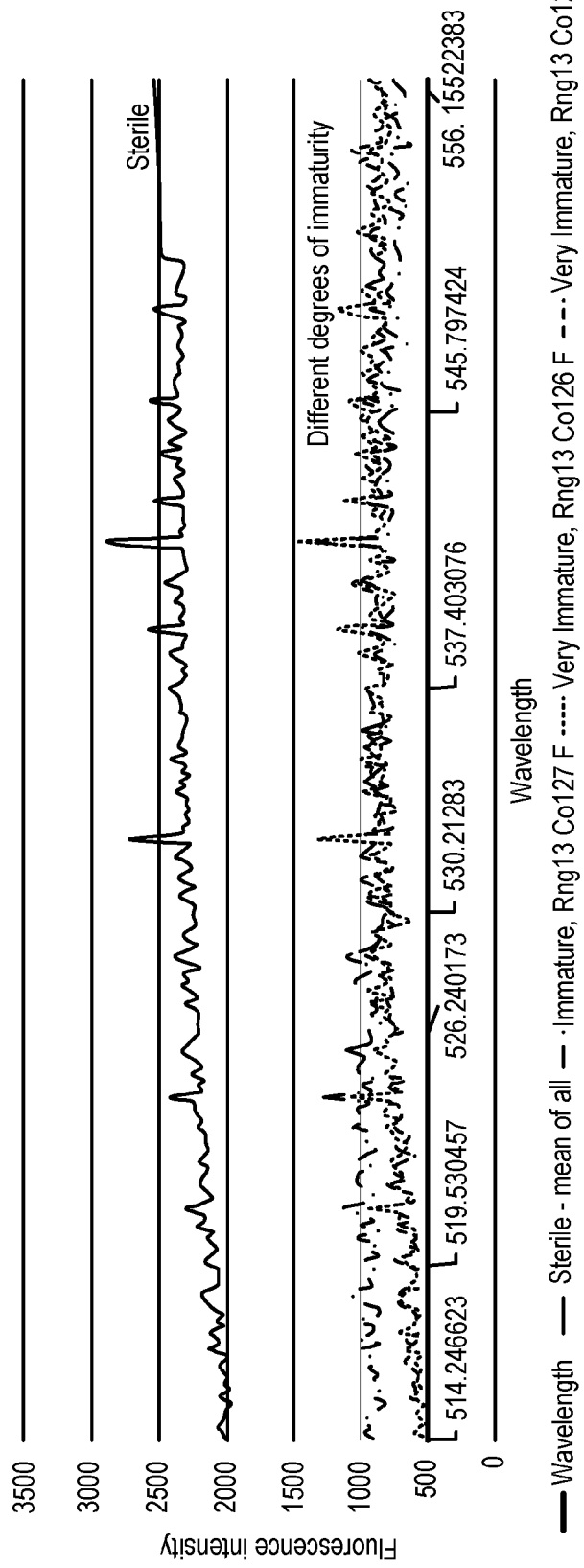
FIG. 42A illustrates spectral data collected in the field for sterile vs. immature fertile non-CMS corn tassels, confirmed by microscopy.
Figure 42B:
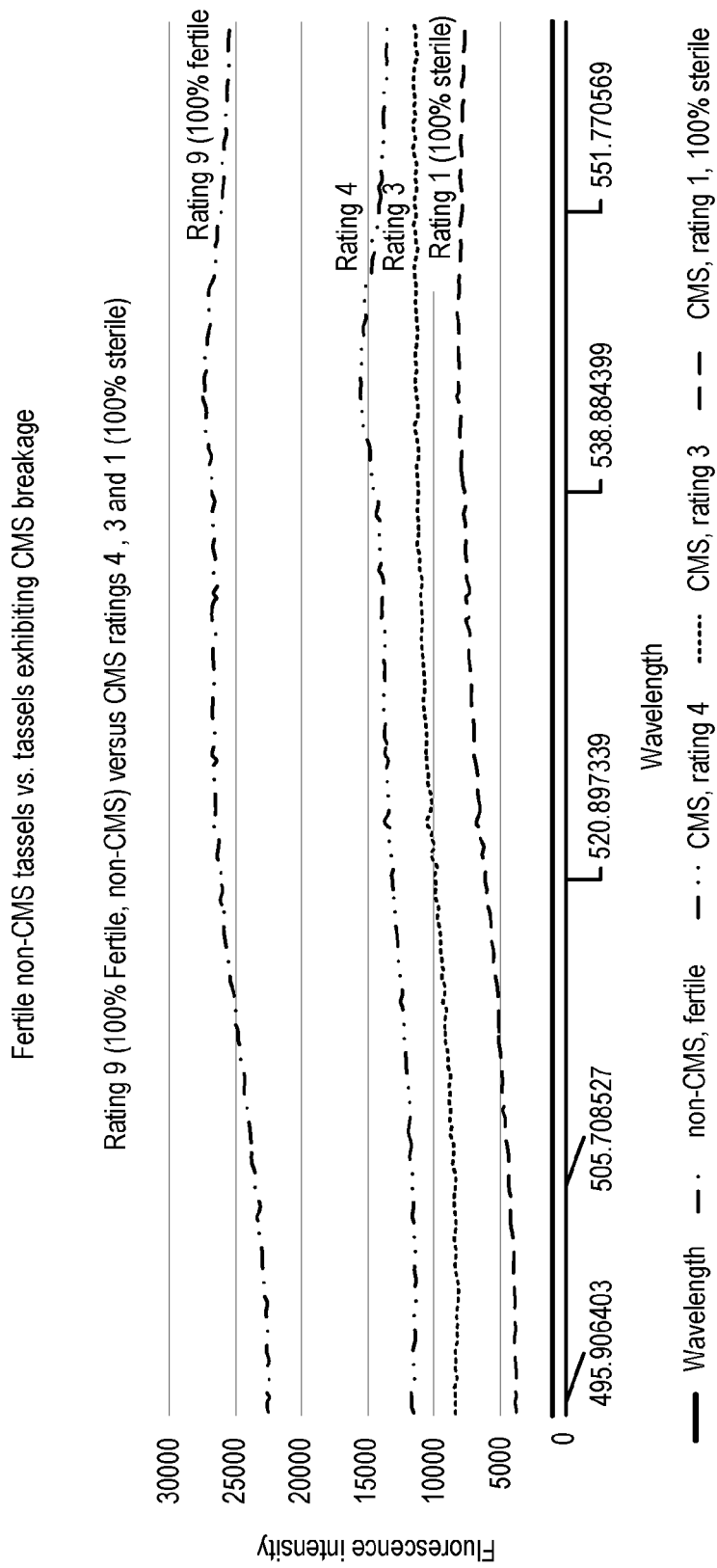
FIG. 42B illustrates spectral data collected in the field comparing fertile non-CMS corn tassels with tassels exhibiting CMS breakage.
Figure 42C:
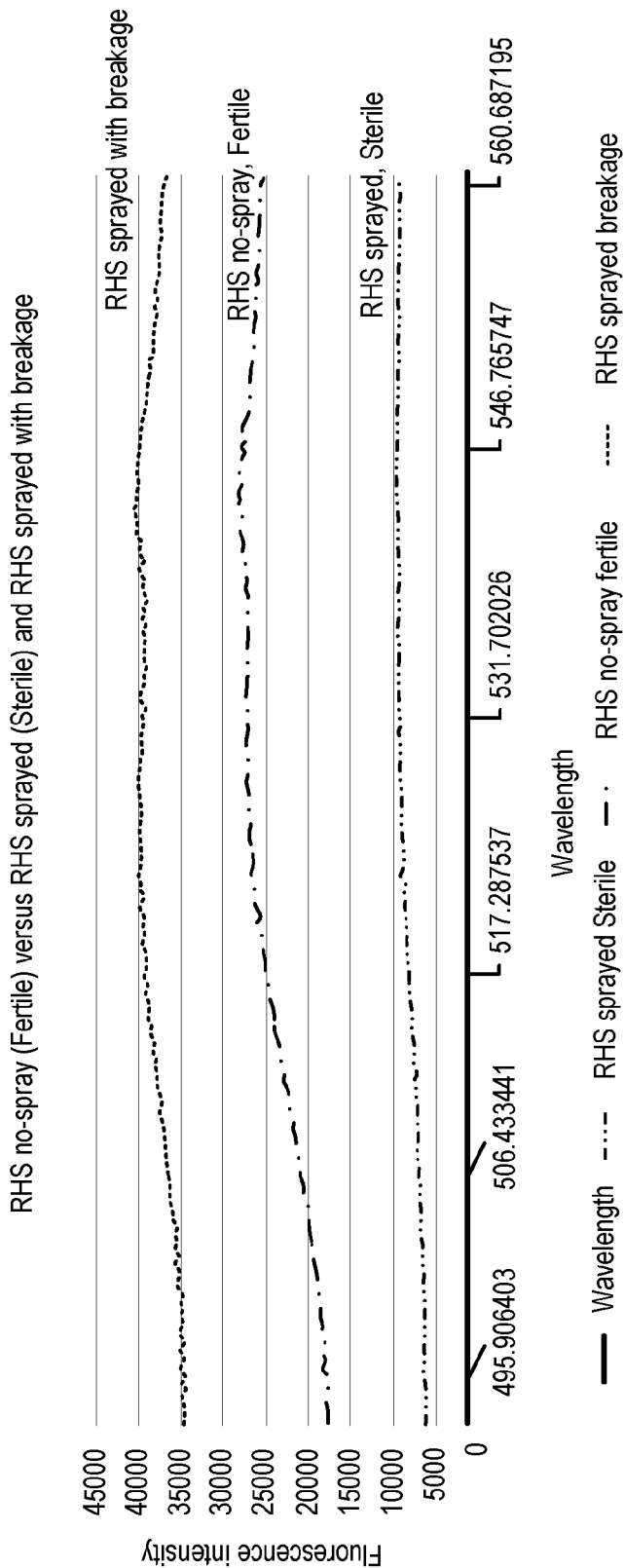
FIG. 42C illustrates spectral data collected in the field comparing fertile RHS no-spray corn with sterile RHS-sprayed corn and RHS sprayed corn with breakage.

FIGS. 42A-C reveals that this relatively simple set up was capable not only of distinguishing fertile plants from completely sterile plants, but could also differentiate different levels of sterility. When the system was used to collect spectroscopic data on immature anthers that contained only a few immature pollen grains (as confirmed by microscopy), the spectral signatures across the 500-550 nm wavelengths were even weaker than the spectral signatures of confirmed sterile anthers/plants. Furthermore, the data reveal that these methods can resolve the spectral signatures of plants with different CMS ratings, i.e. degrees of sterility, as the different spectral signatures of plants with different CMS ratings shown in A25 demonstrate.

Throughout these tests, it was clear that improvements could be made to reduce ambient light contamination from reaching the spectrometer probe while readings were taken. Alternative designs were tested that did a better job eliminating this issue.

The ability of these methods to resolve different degrees of sterility was also demonstrated by analyzing RHS plants growing in the field. Although the expected loss of fertility was observed in most RHS plants sprayed with herbicide, the methods disclosed herein were able to clearly resolve differences in the spectral signatures of the fertile (non-RHS) plants from the RHS-induced sterile plants. Interestingly, some of the RHS plants that should have been made sterile by the RHS spray were remained fertile (again, this was confirmed by microscopy and other methods). This reveals the ability of these methods to not only differentiate sterile vs. fertile plants, but also to detect and differentiate those plants whose fertility under Roundup has been partially restored to some level due to genetic breakage of the RHS trait. Due to differences in sample sizes between the groups studied, it is not unreasonable for the increased intensity exhibited by the RHS sprayed (smaller sample size) with breakage group to be greater than the "fertile" group (larger sample size).

These experiments demonstrate, at least, that the teachings disclosed herein are not limited to laboratory settings and can be applied to field settings to determine plant fertility/sterility in tangible ways. Prospects for combining these teachings with automated technologies, algorithms, artificial intelligence, machine learning, video rendering, etc. are envisioned to improve the throughput of determining fertility vs. sterility.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:
1. A system comprising:
an optical instrument;
a processor,
    wherein the processor is communicatively coupled to the optical instrument;
a computer-readable memory device,
    wherein the computer-readable memory device is communicatively coupled to the optical instrument and the processor;
and an image analysis application,
    wherein the image analysis application comprises processor-executable instructions stored on the computer-readable memory device,
    wherein the instructions, when executed by the processor, configure the image analysis application to:

receive, via the optical instrument, electromagnetic radiation reflected and emitted by a plant specimen;

analyze the received electromagnetic radiation via one or more hyperspectral imaging techniques to determine whether the plant specimen includes pollen on whether the received electromagnetic radiation includes the one or more wavelengths associated with pollen, further comprising a mobile platform configured to controllably traverse a growing area having plants growing therein, wherein the optical instrument is coupled to the mobile platform, and further comprising a robotic appendage coupled to the mobile platform, wherein the instructions, when executed by the processor, configure the processor to generate one or more control signals for manipulating the robotic appendage to remove one or more of the plants identified as having pollen present thereon from the growing area.

2. The system of claim 1, wherein the instructions, when executed by the processor, configure the image analysis application to generate an indication that the plant specimen is sterile when the analysis determines that pollen is absent from the plant specimen.

3. The system of claim 1, wherein the instructions, when executed by the processor, configure the image analysis application to generate an indication that the plant specimen is fertile when the analysis determines that pollen is present on the plant specimen.

4. The system of claim 1, wherein analyzing the received electromagnetic radiation to determine whether the plant specimen includes pollen comprises determining the plant specimen includes pollen when the received electromagnetic radiation includes one or more spectral signatures having a wavelength in at least one of a range of 512 nanometers to 590 nanometers.

5. The system of claim 4, further comprising an electromagnetic radiation source configured to generate electromagnetic radiation for irradiating the plant specimen, wherein the electromagnetic radiation includes one or more wavelengths reflected and emitted by the plant specimen.

6. The system of claim 1, further comprising an electromagnetic radiation source configured to generate electromagnetic radiation for irradiating the plant specimen, wherein the electromagnetic radiation includes one or more wavelengths reflected and emitted by the plant specimen.

7. The system of claim 1, further comprising a display device communicatively coupled to the processor.

8. The system of claim 7, wherein the instructions, when executed by the processor, configure the image analysis application to generate an indication, via the display device, that the plant specimen includes pollen based on the detecting.

9. The system of claim 7, wherein the instructions, when executed by the processor, further configure the image analysis to: generate an image of the plant specimen and the pollen based on the received electromagnetic radiation, wherein the pollen in the generated image is highlighted; and display, via the display device, the image of the plant specimen and the highlighted pollen.

10. The system of claim 1, further comprising an electromagnetic radiation source configured to generate electromagnetic radiation for irradiating the plant specimen, wherein the electromagnetic radiation includes one or more wavelengths reflected emitted by the plant specimen.

11. The system of claim 1, wherein analyzing the received electromagnetic radiation to determine whether the plant specimen includes pollen comprises determining the plant specimen includes pollen when the received electromagnetic radiation includes one or more spectral signatures having a wavelength in at least one of a range of 530 nanometers to 650 nanometers.

12. The system of claim 1, wherein the optical instrument is at least one of a digital camera, a spectrometer, and a hyperspectral fluorescence imager.

* * * * *